US005834591A

United States Patent [19]
Normark et al.

[11] Patent Number: 5,834,591
[45] Date of Patent: Nov. 10, 1998

[54] POLYPEPTIDES AND ANTIBODIES USEFUL FOR THE DIAGNOSIS AND TREATMENT OF PATHOGENIC NEISSERIA AND OTHER MICROORGANISMS HAVING TYPE 4 PILIN

[75] Inventors: Staffan Normark, Clayton, Mo.; Ann-Beth Jonsson, Umea, Sweden

[73] Assignee: Washington University, St. Louis, Mo.

[21] Appl. No.: 415,788

[22] Filed: Apr. 3, 1995

Related U.S. Application Data

[63] Continuation of Ser. No. 829,465, Jan. 31, 1992, abandoned, which is a continuation-in-part of Ser. No. 648,781, Jan. 31, 1991, abandoned.

[51] Int. Cl.⁶ .......................... C07K 14/22; G01N 33/53; G01N 33/569; G01N 33/571
[52] U.S. Cl. .......................... 530/350; 530/300; 530/324; 530/325; 530/326; 435/7.1; 435/7.3; 435/69.1; 435/69.3; 435/71.1; 424/242.1; 424/249.1; 424/250.1
[58] Field of Search ................................. 530/350, 387.1, 530/388.2, 320, 324, 325, 326; 424/242.1, 249.1, 250.1; 435/69.1, 69.3, 71.1, 7.1, 7.3

[56] References Cited

U.S. PATENT DOCUMENTS

| | | | |
|---|---|---|---|
| 4,443,431 | 4/1984 | Buchanan et al. | 424/92 |
| 4,584,195 | 4/1986 | Schoonik et al. | 424/92 |
| 4,795,803 | 1/1989 | Lindberg et al. | 530/324 |

OTHER PUBLICATIONS

Jonsson et al. (1990) Abstract B–17 of the 90th Annual Meeting of the American Society of Microbiology, p. 29.
*New England Biolabs Catalog* (1986/87), New England Biolabs Inc., Beverly, Massachusetts, p. 60.
*Sigma Chemical Company Catalog* (1990), Sigma Chemical Company, St. Louis, Missouri, pp. 859–860.
Jonsson et al EMBO Journal 10:477–488 1991.
ALA' Aldeen et al Molecular & Chemical Aspects of Bacterial Vaccine Development pp. 1–39, Chapter 1.
Jonsson et al, Neisseriae, 1990, Proc Int Paltroy Neuroseria Conf. 7th pp. 431–434.
Boslego et al, Vaccine and Immunotherapy Chapter 17, Gonorrhea Vaccines, pp. 211–223, 1991.
Swaney, L., et al., "Genetic complementation analysis of Escherichia coli type 1 somatic pilus mutants", *Journal of Bacteriology* (1977) 130(1):506–511.
Nunn D., et al., "Products of three accessory genes, pilB, pilC, and pilD, are required for biogenesis of *Pseudomonas aeruginosa pili*", *Journal of Bacteriology* (1990) 172(6):2911–2919.
Perry A., et al., "Neisseria meningitidis C114 contains silent, truncated pilin genes that are homologous to Neisseria gonorrhoeae pil sequences", *Journal of Bacteriology* (1988) 170(4):1691–1697.

Kelley W., et al., "A rapid procedure for isolation of large quantities of Escherichia coli DNA polymerase I utilizing a γpolA transducing phage", *Journal of Biological Chemistry* (1979) 254(9):3206–3210.
Haas R., et al., "Release of soluble pilin antigen coupled with gene conversion in *Neisseria gonorrhoeae*", *Proceedings of the National Academy of Sciences* (1987) 84:9079–9083.
*New England Biolabs Catalog* (1986/87), New England Biolabs Inc., Beverly, Massachusetts, p. 60.
*Sigma Chemical Company Catalog* (1990), Sigma Chemical Company, St. Louis, Missouri, pp. 859–860.
Meyer T., et al., "Pilus genes of *Neisseria gonorrhoeae*: Chromosomal organization and DNA sequence", *Proceedings of the National Academy of Sciences* (1984) 81:6110–6114.
Tinsley C., et al., "Variation in the expression of pili and outer membrane protein by *Neisseria meningitidis* during the course of meningococcal infection", *Journal of General Microbiology* (1986) 132:2483–2490.
Kellogg et al, "*Neiseria gonorrhoeae*: II. Colonial variation and pathogenicity during 35 months in vitro", *J. Bacteriology* (1968) 96:596–605.
Pearce et al., "Attachment role of gonococcal pili: Optimum conditions and quantitation of adherence of isolated pili to human cells in vitro", *J. Clinical Investigation* (1978) 61:931–943.
Swanson, "Studies on gonococcus infection: IV Pili: their role in attachment of gonococci to tissue culture cells", *J. Experimental Medicine* (1973) 137:571–589.
Jonsson A.B., "Identification and Cloning of a kD Outer Mmebrane Protein of Neisseria Gonorrhoeae Enriched in Pili Preparations", *Abstracts from the 90th Annual Meeting of the American Society of Microbiology* (1990) B–17, p. 29.
Tramont, E.C., et al., "Parenteral conococcal Pilus Vaccine" in *The Pathogenic Neisseriae: the Proceedings of the Fourth International Symposium*, (Asilomar, California, USA, 21–25 Oct. 1984); Eds. Gary K. Schoolnik et al., published by the American Society for Microbiology, Washington, D.C., 1985.
Swanson, "Studies on gonococcus infection: IV. Pili: their role in attachment of gonococci to tissure culture cells", *J. Experimental Medicine* (1973) 137:571–589.

(List continued on next page.)

*Primary Examiner*—Hazel F. Sidberry

[57] ABSTRACT

The present invention provides a novel protein of pathogenic forms of Neisseria, as well as genes which encode PilC, i.e., the pilC loci. DNA sequences of pilC genes are useful as probes to diagnose the presence of microorganisms containing type 4 pilin as well as permitting production of polypeptides which are in turn useful in diagnostic tests and/or as components of vaccines. The invention also provides antibodies directed against pilC epitopes. These antibodies are useful for diagnostic tests as well as therapy.

44 Claims, 18 Drawing Sheets

OTHER PUBLICATIONS

Pearce et al., "Attachment role of gonococcoal pili: Optimum conditions and quantitation of adherence of isolated pili to human cells in vitro", *J. Clinical Investigation* (1978) 61:931–943.

Kellogg et al, "*Neisseria gonorrhoeae*: II. Colonial variation and pathogenicity during 35 months in vitro", *J. Bacteriology* (1968) 96:596–605.

Swaney, L., et al., "Genetic complementation analysis of Escherichia coli type 1 somatic pilus mutants", *Journal of Bacteriology* (1977) 130(1):506–511.

Nunn D., et al., "Products of three accessory genes, pilB, pilC, and pilD, are requred for biogenesis of *Pseudomonas aeruginosa pili*", *Journal of Bacteriology* (1990) 172(6):2911–2919.

Perry A., et al., "*Neisseria meningitidis* C114 contains silent, truncated pilin genes that are homologous to Meisseria gonorrhoear pil sequences", *Journal of Bacteriology* (1988) 170(4):1691–1697.

Kelley W., et al., "A rapid procedure for isolation of large quantities of Escherchia coli DNA polymerase I utilizing a γpolA transducing phage", *Journal of Biological Chemistry* (1979) 254(9):3206–3210.

Haas R., et al., "Release of soluble pilin antigen coupled with gene conversion in *Neisseria gonorrhoeae*", *Proceedings of the National Academy of Sciences* (1987) 84:9079–9083.

Meyer T., et al., "Plus genes of *Neisseria gonorrheae*: Chromosomal organizatin and DNA sequences", *Proceedings of the National Academy of Sciences* (1984) 81:6110–6114.

Tinsley C., et al., "Variation in the expression of pili and outer membrane protein by *Neisseria meningitidis* during the course of meningococcal infection", *Journal of General Microbiology* (1986) 132:2483–2490.

```
                    90                    110
CGTCCCGCGAAGGCAAACTTAAGGAATAAAATATGAATAAAACT
                                frame1 MetAsnLysThr
         130            150             170               190
TTGAAACGGCAGGTTTTCCGCCATACCGGCGCTTTATGCCGCCATCTTGATGTTTTCCCATACCGGCGGGGGGGGGG
LeuLysArgGlnValPheArgHisThrAlaLeuTyrAlaAlaIleLeuMetPheSerHisThrGlyGlyGlyGlyGly
         210            230             250               270
CGATGGCGCAAACCCATCAATACGCTATTATCATGAACGAGGCGAAACCAGCCCGAGGTAAAGCAGAATGTGCCATCTT
ArgTrpArgLysProIleAsnThrLeuLeuSer
         MetAlaGlnThrHisGlnTyrAlaAlaIleIleMetAsnGluArgAsnGlnProGluValLysGlnAsnValProSerS
frame2                            | 1 | 2 | 3 | 4 | 5 | 6 | 7 | 8 | 9 | 10 |
                                  | ? | ? | ? | ? | LysTyrAlaIleIleMetAsn |
```

FIG. 2

```
GATCCGCCCG GTGCTTGGGC GCCTTAGGGA ACCGTTCCCT TTGAGCCGGG GCGGGGCAAC    60
GCGTACCGGT TTTTGTTAAT CCGCTATAAA AGGCGGGCTA TAGGGTAGGC TTCATCCTGC   120
CAATCTCACT GAATCCGTCA ATTTCCGCAA TTCAATTAAA TACCGTCAAA CCGATGCCGT   180
CATTCCGCGC AGGCGGGAAT CCGGACCGGT CGGGCATCTG CGGCGGTTTG CTAAAAAACG   240
CTTTACCGTG ATAAGTGCGC AAAGTTAAAA TGGGGAGGTA AGCTTTTCAA TCAGCAATCC   300
GGCGGGCGCG GAATCGGGCG GTTTACCGAA CCCCGGCGTT CGCGGCGCCC GTCCCGCGAA   360
GGCAAACTTA AGGAATAAAA TATGAATAAA ACTTTGAAAC GGCAGGTTTT CCGCCATACC   420
GCGCTTTATG CCGCCATCTT GATGTTTTCC CATACCGGCG GGGGGGGGGG GCGATGGCGC   480
AAACCCATCA ATACGCTATT ATCATGAACG AGCGAAACCA GCCCGAGGTA AGCAGAATG    540
TGCCATCTTC AATAAAGGAC AAAGACAGGA GGCGCGAATA TACTTATTAT ACGCACAGAA   600
CAGGAGCAGG CTCTGTCTCA TTCAACAATA ACGATACCCT TGTTTCCCAA CAAAGCGGTA   660
CTGCCGTTTT TGGCACAGCC ACCTACCTGC CGCCCTACGG CAAGGTTTCC GGTTTTGATG   720
CCGTCGCTCT GAAAGAGCGC AACAATGCCG TTGATTGGAT TCGTACCACC CGCATCGCGC   780
TGGCAGGCTA CTCCTACATC GACGTCATAT GCAGAAGCTA CACAGGCTGT CCCAAACTTG   840
TCTATAAAAC CCGATTTACC TTCGGTCAAC AAGGGTTGAA AAGAAAGGCA GGCAGCAAGC   900
TGGATATATA CGAAGACAAA AGCCGCGAAA ATTCGCCCAT TTACAAATTG TCGGATTATC   960
CTTGGTTGGG CGTATCTTTC AATTTGGGCA GCGAGAATAC CGTCCAAAAT AGCAAATTAT  1020
TCAACAAATT GATATCTTCT TTTAGAGAAG GCAATAATAA TCAAACCATC GTCTCTACGA  1080
CAGAAGGCAA CCCTATTTCC CTTGGCGACC GGCAGCGCGA ACATACCGCC GTGGCCTATT  1140
ATCTGAACGC CAAACTGCAC CTGCTGGACA AAAAAGGGAT TGAAGATATC GCCCAAGGCA  1200
AAATAGTGGA TTTGGGTATC TTGAAACCGC ACGTCGAGAC GACAGGACGA AGCTTGCTAG  1260
ATTTTTGGGC TAGGTGGGAC ATTAAAGATA CCGGGCAGAT TCCGGTCAAG CTCGGCCTGC  1320
CGCAAGTCAA AGCAGGCCGC TGCACCAACA AACCGAACCC CAATAATAAT ACCAAAGCCC  1380
CTTCGCCGGC ACTGACCGCC CCCGCGCTGT GGTTCGGACC CGGGCAAGAT GGTAAGGCGG  1440
AGATGTATTC CGCTTCGGTT TCCACCTACC CCGACAGTTC GAGCAGCCGC ATCTTCCTCC  1500
AAGAGCTGAA AACTCAAACC GAACCCGGCA AACCCGGCCG CTATTCCCTC AAATCTTTGA  1560
ATGATGGTGA GATTAAAAGT CGACAGCCGA GTTTCAACGG GCGGCAAACA ATCATCCGAT  1620
TGGATGACGG CGTACATTTG ATCAAACTGA ATGGAAGCAA GGATGAGGTC GCCGCTTTTG  1680
TCAATTTAAA TGGAAACAAC ACCGGCAAAA ACGACACTTT CGGCATTGTT AAGGAAGCGA  1740
ACGTCAATCT TGACGCCGAC GAGTGGAAAA AAGTGCTGCT GCCTTGGACG GTTCGGGGTC  1800
CCGATAATGA CAATAAATTT AAATCAATTA ACCAAAAACC AGAAAAATAC AGCCAAAGAT  1860
```

FIG. 3A

```
ACCGCATCCG CGACAACAAC GGCAATCGCG ATTTGGGCGA CATCGTCAAC AGCCCGATTG  1920
TCGCGGTCGG CGGGTATTTG GCAACCGCCG CGAACGACGG GATGGTGCAT ATCTTCAAAA  1980
AAAACGGCGG CAGTGATGAA CGCAGCTACA ATCTGAAGCT CAGCTACATC CCCGGCACGA  2040
TGCCGCGCAA GGATATTCAA AGCCAAGAAT CCACCCTTGC CAAAGAGCTG CGCGCCTTTG  2100
CCGAAAAAGG CTATGTGGGC GACCGCTACG GCGTGGACGG CGGCTTTGTC TTGCGCCAAG  2160
TCGAACTGAG CGGGCAAAAA CACGTGTTTA TGTTCGGCGC GATGGGTTTT GGCGGCAGGG  2220
GCGCGTATGC CTTGGATTTA AGCAAAATCA ACGGAAATTA TCCGGCCGCC GCCCCCCTGT  2280
TTGATGTCAA AGATGGCGAT AATAACGGCA AAAATCGCGT GAAAGTGGAA TTAGGCTACA  2340
CCGTCGGTAC GCCGCAAATC GGCAAAATCC GCAACGGCAA ATACGCCGCC TTCCTCGCCT  2400
CCGGTTATGC GGCTAAAAAA ATTGACGACT CAACAAATAA AACCGCGCTG TATGTATATG  2460
ATTTGAAAGA CACCTTAGGT ACGCCGATTG CAAAAATCGA AGTGAAGGAC GGCAAAGGCG  2520
GGCTTTCGTC CCCCACGCTG GTGGATAAAG ATTTGGACGG CACGGTCGAT ATCGCCTATG  2580
CCGGCGACCG GGGCGGCAAT ATGTACCGCT TTGATTTGAG CAATTCCGAT TCTAGTAAAT  2640
GGTCTGCAAA GGTTATTTTC GAAGGCGACA AGCCGATTAC CTCCGCGCCC GCCGTTTCCC  2700
GACTGGCAGA CAAACGCGTC GTCATCTTCG GTACGGGCAG CGATTTGACC GAAGATGATG  2760
TACTGAATAC GGGCGAACAA TATATTTACG GTATCTTTGA CGACGATAAG GGGACGGTTA  2820
AGGTAACGGT ACAAAACGGC ACGGCAGGCG GGCTGCTCGA GCAACACCTT ACTCAGGAAA  2880
ATAAAACATT ATTCCTGAAC AAGAGATCCG ACGGTTCGGG CAGCAAGGGC TGGGCGGTGA  2940
AATTGAGGGA AGGAGAACGC GTTACCGTCA AACCGACCGT GGTATTGCGT ACCGCCTTCG  3000
TAACCATCCG CAAATATAAC GACGGCGGCT GCGGCGCGGA AACCGCCATT TTGGGCATCA  3060
ATACCGCCGA CGGCGGCGCA TTGACTCCGA GAAGCGCGCG CCCGATTGTG CCGGATCACA  3120
ATTCGGTTGC GCAATATTCC GGCCATAAGA CAACCTCCAA AGGCAAATCC ATCCCTATAG  3180
GTTGTATGGA CAAAGACGGT AAAACCGTCT GCCCGAACGG ATATGTTTAC GACAAGCCGG  3240
TTAATGTGCG TTATCTGGAT GAAACGGAAA CAGACGGATT TTCAACGACG GCGGACGGCG  3300
ATGCGGGCGG CAGCGGTATA GACCCCGCCG GCAGGCGTCC CGGCAAAAAC AACCGCTGCT  3360
TCTCCAAAAA AGGGGTGCGC ACCCTGCTGA TGAACGATTT GGACAGCTTG GATATTACCG  3420
GCCCGATGTG CGGTATCAAA CGCTTAAGCT GGCGCGAAGT CTTCTTCTGA CCGGCCTGCG  3480
CGGCCGGTTT TTCCGCAAAT GCCGTCCGAA AGGCCTTCGG ACGGCATTTT TTTGCGTTTT  3540
TCGGGAGGGG GGCGGCAAAT GAAACG                                     3566
```

FIG. 3B

```
              10                    30                    50
GATCCGCCCGGTGCTTGGGCGCCTTAGGGAACCGTTCCCTTTGAGCCGGGGCGGGGCAAC
              70                    90                    110
GCGTACCGGTTTTTGTTAATCCGCTATAAAAGGCGGGCTATAGGGTAGGCTTCATCCTGC
              130                   150                   170
CAATCTCACTGAATCCGTCAATTTCCGCAATTCAATTAAATACCGTCAAACCGATGCCGT
              190                   210                   230
CATTCCGCGCAGGCGGGAATCCGGACCGGTCGGGCATCTGCGGCGGTTTGCTAAAAAACG
              250                   270                   290
CTTTACCGTGATAAGTGCGCAAAGTTAAAATGGGGAGGTAAGCTTTTCAATCAGCAATCC
              310                   330                   350
GGCGGGCGCGGAATCGGGCGGTTTACCGAACCCCGGCGTTCGCGGCGCCCGTCCCGCGAA
              370                   390                   410
GGCAAACTTAAGGAATAAAATATGAATAAAACTTTGAAACGGCAGGTTTTCCGCCATACC
                              M  N  K  T  L  K  R  Q  V  F  R  H  T
                        430                   450                   470
          GCGCTTTATGCCGCCATCTTGATGTTTTCCCATACCGGCGGGGGGGGGGGCGATGGCG
           A  L  Y  A  A  I  L  M  F  S  H  T  G  G  G  G  A  M  A
                        490                   510                   530
          CAAACCCATCAATACGCTATTATCATGAACGAGCGAAACCAGCCCGAGGTAAAGCAGAAT
           Q  T  H  Q  Y  A  I  I  M  N  E  R  N  Q  P  E  V  K  Q  N
                        550                   570                   590
          GTGCCATCTTCAATAAAGGACAAAGACAGGAGGCGCGAATATACTTATTATACGCACAGA
           V  P  S  S  I  K  D  K  D  R  R  E  Y  T  Y  Y  T  H  R
                        610                   630                   650
          ACAGGAGGAGGCTCTGTCTCATTCAACAATAACGATACCCTTGTTTCCCAACAAAGCGGT
           T  G  G  G  S  V  S  F  N  N  N  D  T  L  V  S  Q  Q  S  G
                        670                   690                   710
          ACTGCCGTTTTTGGCACAGCCACCTACCTGCCGCCCTACGGCAAGGTTTCCGGTTTTGAT
           T  A  V  F  G  T  A  T  Y  L  P  P  Y  G  K  V  S  G  F  D
                        730                   750                   770
          GCCGTCGCTCTGAAAGAGCGCAACAATGCCGTTGATTGGATTCGTACCACCCGCATCGCG
           A  V  A  L  K  E  R  N  N  A  V  D  W  I  R  T  T  R  I  A
                        790                   810                   830
          CTGGCAGGCTACTCCTACATCGACGTCATATGCAGAAGCTACACAGGCTGTCCCAAACTT
           L  A  G  Y  S  Y  I  D  V  I  C  R  S  Y  T  G  C  P  K  L
                        850                   870                   890
          GTCTATAAACCCGATTTACCTTCGGTCAACAAGGGTTGAAAAGAAAGGCAGGCAGCAAG
           V  Y  K  T  R  F  T  F  G  Q  Q  G  L  K  R  K  A  G  S  K
                        910                   930                   950
          CTGGATATATACGAAGACAAAAGCCGCGAAATTCGCCCATTTACAAATTGTCGGATTAT
           L  D  I  Y  E  D  K  S  R  E  N  S  P  I  Y  K  L  S  D  Y
                        970                   990                   1010
          CCTTGGTTGGGCGTATCTTTCAATTTGGGCAGCGAGAATACCGTCCAAATAGCAAATTA
           P  W  L  G  V  S  F  N  L  G  S  E  N  T  V  Q  N  S  K  L
```

FIG. 4A

```
                1030                  1050                  1070
TTCAACAAATTGATATCTTCTTTTAGAGAAGGCAATAATAATCAAACCATCGTCTCTACG
  F   N   K   L   I   S   S   F   R   E   G   N   N   N   Q   T   I   V   S   T
                1090                  1110                  1130
ACAGAAGGCAACCCTATTTCCCTTGGCGACCGGCAGCGCGAACATACCGCCGTGGCCTAT
  T   E   G   N   P   I   S   L   G   D   R   Q   R   E   H   T   A   V   A   Y
                1150                  1170                  1190
TATCTGAACGCCAAACTGCACCTGCTGGACAAAAAGGGATTGAAGATATCGCCCAAGGC
  Y   L   N   A   K   L   H   L   L   D   K   K   G   I   E   D   I   A   Q   G
                1210                  1230                  1250
AAAATAGTGGATTTGGGTATCTTGAAACCGCACGTCGAGACGACAGGACGAAGCTTGCTA
  K   I   V   D   L   G   I   L   K   P   H   V   E   T   T   G   R   S   L   L
                1270                  1290                  1310
GATTTTTGGGCTAGGTGGGACATTAAAGATACCGGGCAGATTCCGGTCAAGCTCGGCCTG
  D   F   W   A   R   W   D   I   K   D   T   G   Q   I   P   V   K   L   G   L
                1330                  1350                  1370
CCGCAAGTCAAAGCAGGCCGCTGCACCAACAAACCGAACCCCAATAATAATACCAAAGCC
  P   Q   V   K   A   G   R   C   T   N   K   P   N   P   N   N   N   T   K   A
                1390                  1410                  1430
CCTTCGCCGGCACTGACCGCCCCCGCGCTGTGGTTCGGACCCGGGCAAGATGGTAAGGCG
  P   S   P   A   L   T   A   P   A   L   W   F   G   P   G   Q   D   G   K   A
                1450                  1470                  1490
GAGATGTATTCCGCTTCGGTTTCCACCTACCCCGACAGTTCGAGCAGCCGCATCTTCCTC
  E   M   Y   S   A   S   V   S   T   Y   P   D   S   S   S   S   R   I   F   L
                1510                  1530                  1550
CAAGAGCTGAAAACTCAAACCGAACCCGGCAAACCCGGCCGCTATTCCCTCAAATCTTTG
  Q   E   L   K   T   Q   T   E   P   G   K   P   G   R   Y   S   L   K   S   L
                1570                  1590                  1610
AATGATGGTGAGATTAAAAGTCGACAGCCGAGTTTCAACGGGCGGCAAACAATCATCCGA
  N   D   G   E   I   K   S   R   Q   P   S   F   N   G   R   Q   T   I   I   R
                1630                  1650                  1670
TTGGATGACGGCGTACATTTGATCAAACTGAATGGAAGCAAGGATGAGGTCGCCGCTTTT
  L   D   D   G   V   H   L   I   K   L   N   G   S   K   D   E   V   A   A   F
                1690                  1710                  1730
GTCAATTTAAATGGAAACAACACCGGCAAAAACGACACTTTCGGCATTGTTAAGGAAGCG
  V   N   L   N   G   N   N   T   G   K   N   D   T   F   G   I   V   K   E   A
                1750                  1770                  1790
AACGTCAATCTTGACGCCGACGAGTGGAAAAAAGTGCTGCTGCCTTGGACGGTTCGGGGT
  N   V   N   L   D   A   D   E   W   K   K   V   L   L   P   W   T   V   R   G
                1810                  1830                  1850
CCCGATAATGACAATAAATTTAAATCAATTAACCAAAAACCAGAAAAATACAGCCAAAGA
  P   D   N   D   N   K   F   K   S   I   N   Q   K   P   E   K   Y   S   Q   R
                1870                  1890                  1910
TACCGCATCCGCGACAACAACGGCAATCGCGATTTGGGCGACATCGTCAACAGCCCGATT
  Y   R   I   R   D   N   N   G   N   R   D   L   G   D   I   V   N   S   P   I
```

FIG. 4B

```
                1930               1950                1970
GTCGCGGTCGGCGGGTATTTGGCAACCGCCGCGAACGACGGGATGGTGCATATCTTCAAA
 V  A  V  G  G  Y  L  A  T  A  A  N  D  G  M  V  H  I  F  K
                1990               2010                2030
AAAAACGGCGGCAGTGATGAACGCAGCTACAATCTGAAGCTCAGCTACATCCCCGGCACG
 K  N  G  G  S  D  E  R  S  Y  N  L  K  L  S  Y  I  P  G  T
                2050               2070                2090
ATGCCGCGCAAGGATATTCAAAGCCAAGAATCCACCCTTGCCAAAGAGCTGCGCGCCTTT
 M  P  R  K  D  I  Q  S  Q  E  S  T  L  A  K  E  L  R  A  F
                2110               2130                2150
GCCGAAAAAGGCTATGTGGGCGACCGCTACGGCGTGGACGGCGGCTTTGTCTTGCGCCAA
 A  E  K  G  Y  V  G  D  R  Y  G  V  D  G  G  F  V  L  R  Q
                2170               2190                2210
GTCGAACTGAGCGGGCAAAAACACGTGTTTATGTTCGGCGCGATGGGTTTTGGCGGCAGG
 V  E  L  S  G  Q  K  H  V  F  M  F  G  A  M  G  F  G  G  R
                2230               2250                2270
GGCGCGTATGCCTTGGATTTAAGCAAAATCAACGGAAATTATCCGGCCGCCGCCCCCCTG
 G  A  Y  A  L  D  L  S  K  I  N  G  N  Y  P  A  A  A  P  L
                2290               2310                2330
TTTGATGTCAAAGATGGCGATAATAACGGCAAAAATCGCGTGAAAGTGGAATTAGGCTAC
 F  D  V  K  D  G  D  N  N  G  K  N  R  V  K  V  E  L  G  Y
                2350               2370                2390
ACCGTCGGTACGCCGCAAATCGGCAAAATCCGCAACGGCAAATACGCCGCCTTCCTCGCC
 T  V  G  T  P  Q  I  G  K  I  R  N  G  K  Y  A  A  F  L  A
                2410               2430                2450
TCCGGTTATGCGGCTAAAAAAATTGACGACTCAACAAATAAAACCGCGCTGTATGTATAT
 S  G  Y  A  A  K  K  I  D  D  S  T  N  K  T  A  L  Y  V  Y
                2470               2490                2510
GATTTGAAAGACACCTTAGGTACGCCGATTGCAAAAATCGAAGTGAAGGACGGCAAAGGC
 D  L  K  D  T  L  G  T  P  I  A  K  I  E  V  K  D  G  K  G
                2530               2550                2570
GGGCTTTCGTCCCCCACGCTGGTGGATAAAGATTTGGACGGCACGGTCGATATCGCCTAT
 G  L  S  S  P  T  L  V  D  K  D  L  D  G  T  V  D  I  A  Y
                2590               2610                2630
GCCGGCGACCGGGGCGGCAATATGTACCGCTTTGATTTGAGCAATTCCGATTCTAGTAAA
 A  G  D  R  G  G  N  M  Y  R  F  D  L  S  N  S  D  S  S  K
                2650               2670                2690
TGGTCTGCAAAGGTTATTTTCGAAGGCGACAAGCCGATTACCTCCGCGCCCGCCGTTTCC
 W  S  A  K  V  I  F  E  G  D  K  P  I  T  S  A  P  A  V  S
                2710               2730                2750
CGACTGGCAGACAAACGCGTCGTCATCTTCGGTACGGGCAGCGATTTGACCGAAGATGAT
 R  L  A  D  K  R  V  V  I  F  G  T  G  S  D  L  T  E  D  D
                2770               2790                2810
GTACTGAATACGGGCGAACAATATATTTACGGTATCTTTGACGACGATAAGGGGACGGTT
 V  L  N  T  G  E  Q  Y  I  Y  G  I  F  D  D  D  K  G  T  V
```

FIG. 4C

```
                     2830                    2850                    2870
AAGGTAACGGTACAAAACGGCACGGCAGGCGGGCTGCTCGAGCAACACCTTACTCAGGAA
 K  V  T  V  Q  N  G  T  A  G  G  L  L  E  Q  H  L  T  Q  E
                     2890                    2910                    2930
AATAAAACATTATTCCTGAACAAGAGATCCGACGGTTCGGGCAGCAAGGGCTGGGCGGTG
 N  K  T  L  F  L  N  K  R  S  D  G  S  G  S  K  G  W  A  V
                     2950                    2970                    2990
AAATTGAGGGAAGGAGAACGCGTTACCGTCAAACCGACCGTGGTATTGCGTACCGCCTTC
 K  L  R  E  G  E  R  V  T  V  K  P  T  V  V  L  R  T  A  F
                     3010                    3030                    3050
GTAACCATCCGCAAATATAACGACGGCGGCTGCGGCGCGGAAACCGCCATTTTGGGCATC
 V  T  I  R  K  Y  N  D  G  G  C  G  A  E  T  A  I  L  G  I
                     3070                    3090                    3110
AATACCGCCGACGGCGGCGCATTGACTCCGAGAAGCGCGCGCCCGATTGTGCCGGATCAC
 N  T  A  D  G  G  A  L  T  P  R  S  A  R  P  I  V  P  D  H
                     3130                    3150                    3170
AATTCGGTTGCGCAATATTCCGGCCATAAGACAACCTCCAAAGGCAAATCCATCCCTATA
 N  S  V  A  Q  Y  S  G  H  K  T  T  S  K  G  K  S  I  P  I
                     3190                    3210                    3230
GGTTGTATGGACAAAGACGGTAAAACCGTCTGCCCGAACGGATATGTTTACGACAAGCCG
 G  C  M  D  K  D  G  K  T  V  C  P  N  G  Y  V  Y  D  K  P
                     3250                    3270                    3290
GTTAATGTGCGTTATCTGGATGAAACGGAAACAGACGGATTTTCAACGACGGCGGACGGC
 V  N  V  R  Y  L  D  E  T  E  T  D  G  F  S  T  T  A  D  G
                     3310                    3330                    3350
GATGCGGGCGGCAGCGGTATAGACCCCGCCGGCAGGCGTCCCGGCAAAAACAACCGCTGC
 D  A  G  G  S  G  I  D  P  A  G  R  R  P  G  K  N  N  R  C
                     3370                    3390                    3410
TTCTCCAAAAAAGGGGTGCGCACCCTGCTGATGAACGATTTGGACAGCTTGGATATTACC
 F  S  K  K  G  V  R  T  L  L  M  N  D  L  D  S  L  D  I  T
                     3430                    3450                    3470
GGCCCGATGTGCGGTATCAAACGCTTAAGCTGGCGCGAAGTCTTCTTCTGACCGGCCTGC
 G  P  M  C  G  I  K  R  L  S  W  R  E  V  F  F  *
                     3490                    3510                    3530
GCGGCCGGTTTTTCCGCAAATGCCGTCCGAAAGGCCTTCGGACGGCATTTTTTTGCGTTT
                     3550
TTCGGGAGGGGGGCGGCAAATGAAACG
```

FIG. 4D

```
                  10                      30                      50
         GATCCGCCCGGTGCTTGGGCGCCTTAGGGAACCGTTCCCTTTGAGCCGGGGCGGGGCAAC
                  70                      90                      110
         GCGTACCGGTTTTTGTTAATCCGCTATAAAAGGCGGGCTATAGGGTAGGCTTCATCCTGC
                  130                     150                     170
         CAATCTCACTGAATCCGTCAATTTCCGCAATTCAATTAAATACCGTCAAACCGATGCCGT
                  190                     210                     230
         CATTCCGCGCAGGCGGGAATCCGGACCGGTCGGGCATCTGCGGCGGTTTGCTAAAAAACG
                  250                     270                     290
         CTTTACCGTGATAAGTGCGCAAAGTTAAAATGGGGAGGTAAGCTTTTCAATCAGCAATCC
                  310                     330                     350
         GGCGGGCGCGGAATCGGGCGGTTTACCGAACCCCGGCGTTCGCGGCGCCCGTCCCGCGAA
                  370                     390                     410
         GGCAAACTTAAGGAATAAAATATGAATAAAACTTTGAAACGGCAGGTTTTCCGCCATACC
                         frame 1   M  N  K  T  L  K  R  Q  V  F  R  H  T
                  430                     450                     470
         GCGCTTTATGCCGCCATCTTGATGTTTTCCCATACCGGCGGGGGGGGGGCGATGGCGC
          A  L  Y  A  A  I  L  M  F  S  H  T  G  G  G  G  G  R  W  R
                                                        frame 2   M  A
                  490                     510                     530
         AAACCCATCAATACGCTATTATCATGAACGAGCGAAACCAGCCCGAGGTAAAGCAGAATG
          K  P  I  N  T  L  L  S  *
          Q  T  H  Q  Y  A  I  I  M  N  E  R  N  Q  P  E  V  K  Q  N
                  550                     570                     590
         TGCCATCTTCAATAAAGGACAAAGACAGGAGGCGCGAATATACTTATTATACGCACAGAA
          V  P  S  S  I  K  D  K  D  R  R  R  E  Y  T  Y  Y  T  H  R
                  610                     630                     650
         CAGGAGCAGGCTCTGTCTCATTCAACAATAACGATACCCTTGTTTCCCAACAAAGCGGTA
          T  G  A  G  S  V  S  F  N  N  N  D  T  L  V  S  Q  Q  S  G
                  670                     690                     710
         CTGCCGTTTTTGGCACAGCCACCTACCTGCCGCCCTACGGCAAGGTTTCCGGTTTTGATG
          T  A  V  F  G  T  A  T  Y  L  P  P  Y  G  K  V  S  G  F  D
                  730                     750                     770
         CCGTCGCTCTGAAAGAGCGCAACAATGCCGTTGATTGGATTCGTACCACCCGCATCGCGC
          A  V  A  L  K  E  R  N  N  A  V  D  W  I  R  T  T  R  I  A
                  790                     810                     830
         TGGCAGGCTACTCCTACATCGACGTCATATGCAGAAGCTACACAGGCTGTCCCAAACTTG
          L  A  G  Y  S  Y  I  D  V  I  C  R  S  Y  T  G  C  P  K  L
                  850                     870                     890
         TCTATAAAACCCGATTTACCTTCGGTCAACAAGGGTTGAAAAGAAAGGCAGGCAGCAAGC
          V  Y  K  T  R  F  T  F  G  Q  Q  G  L  K  R  K  A  G  S  K
                  910                     930                     950
         TGGATATATACGAAGACAAAAGCCGCGAAAATTCGCCCATTTACAAATTGTCGGATTATC
          L  D  I  Y  E  D  K  S  R  E  N  S  P  I  Y  K  L  S  D  Y
                  970                     990                     1010
         CTTGGTTGGGCGTATCTTTCAATTTGGGCAGCGAGAATACCGTCCAAAATAGCAAATTAT
          P  W  L  G  V  S  F  N  L  G  S  E  N  T  V  Q  N  S  K  L
```

FIG. 5A

```
            1030                1050                1070
TCAACAAATTGATATCTTCTTTTAGAGAAGGCAATAATAATCAAACCATCGTCTCTACGA
 F  N  K  L  I  S  S  F  R  E  G  N  N  N  Q  T  I  V  S  T
            1090                1110                1130
CAGAAGGCAACCCTATTTCCCTTGGCGACCGGCAGCGCGAACATACCGCCGTGGCCTATT
 T  E  G  N  P  I  S  L  G  D  R  Q  R  E  H  T  A  V  A  Y
            1150                1170                1190
ATCTGAACGCCAAACTGCACCTGCTGGACAAAAAAGGGATTGAAGATATCGCCCAAGGCA
 Y  L  N  A  K  L  H  L  L  D  K  K  G  I  E  D  I  A  Q  G
            1210                1230                1250
AAATAGTGGATTTGGGTATCTTGAAACCGCACGTCGAGACGACAGGACGAAGCTTGCTAG
 K  I  V  D  L  G  I  L  K  P  H  V  E  T  T  G  R  S  L  L
            1270                1290                1310
ATTTTTGGGCTAGGTGGGACATTAAAGATACCGGGCAGATTCCGGTCAAGCTCGGCCTGC
 D  F  W  A  R  W  D  I  K  D  T  G  Q  I  P  V  K  L  G  L
            1330                1350                1370
CGCAAGTCAAAGCAGGCCGCTGCACCAACAAACCGAACCCCAATAATAATACCAAAGCCC
 P  Q  V  K  A  G  R  C  T  N  K  P  N  P  N  N  N  T  K  A
            1390                1410                1430
CTTCGCCGGCACTGACCGCCCCCGCGCTGTGGTTCGGACCCGGGCAAGATGGTAAGGCGG
 P  S  P  A  L  T  A  P  A  L  W  F  G  P  G  Q  D  G  K  A
            1450                1470                1490
AGATGTATTCCGCTTCGGTTTCCACCTACCCCGACAGTTCGAGCAGCCGCATCTTCCTCC
 E  M  Y  S  A  S  V  S  T  Y  P  D  S  S  S  S  R  I  F  L
            1510                1530                1550
AAGAGCTGAAAACTCAAACCGAACCCGGCAAACCCGGCCGCTATTCCCTCAAATCTTTGA
 Q  E  L  K  T  Q  T  E  P  G  K  P  G  R  Y  S  L  K  S  L
            1570                1590                1610
ATGATGGTGAGATTAAAAGTCGACAGCCGAGTTTCAACGGGCGGCAAACAATCATCCGAT
 N  D  G  E  I  K  S  R  Q  P  S  F  N  G  R  Q  T  I  I  R
            1630                1650                1670
TGGATGACGGCGTACATTTGATCAAACTGAATGGAAGCAAGGATGAGGTCGCCGCTTTTG
 L  D  D  G  V  H  L  I  K  L  N  G  S  K  D  E  V  A  A  F
            1690                1710                1730
TCAATTTAAATGGAAACAACACCGGCAAAAACGACACTTTCGGCATTGTTAAGGAAGCGA
 V  N  L  N  G  N  N  T  G  K  N  D  T  F  G  I  V  K  E  A
            1750                1770                1790
ACGTCAATCTTGACGCCGACGAGTGGAAAAAAGTGCTGCTGCCTTGGACGGTTCGGGGTC
 N  V  N  L  D  A  D  E  W  K  K  V  L  L  P  W  T  V  R  G
            1810                1830                1850
CCGATAATGACAATAAATTTAAATCAATTAACCAAAAACCAGAAAAATACAGCCAAAGAT
 P  D  N  D  N  K  F  K  S  I  N  Q  K  P  E  K  Y  S  Q  R
            1870                1890                1910
ACCGCATCCGCGACAACAACGGCAATCGCGATTTGGGCGACATCGTCAACAGCCCGATTG
 Y  R  I  R  D  N  N  G  N  R  D  L  G  D  I  V  N  S  P  I
```

FIG. 5B

```
     1930                1950                1970
TCGCGGTCGGCGGGTATTTGGCAACCGCCGCGAACGACGGGATGGTGCATATCTTCAAAA
 V  A  V  G  G  Y  L  A  T  A  A  N  D  G  M  V  H  I  F  K
     1990                2010                2030
AAAACGGCGGCAGTGATGAACGCAGCTACAATCTGAAGCTCAGCTACATCCCCGGCACGA
 K  N  G  G  S  D  E  R  S  Y  N  L  K  L  S  Y  I  P  G  T
     2050                2070                2090
TGCCGCGCAAGGATATTCAAAGCCAAGAATCCACCCTTGCCAAAGAGCTGCGCGCCTTTG
 M  P  R  K  D  I  Q  S  Q  E  S  T  L  A  K  E  L  R  A  F
     2110                2130                2150
CCGAAAAAGGCTATGTGGGCGACCGCTACGGCGTGGACGGCGGCTTTGTCTTGCGCCAAG
 A  E  K  G  Y  V  G  D  R  Y  G  V  D  G  G  F  V  L  R  Q
     2170                2190                2210
TCGAACTGAGCGGGCAAAAACACGTGTTTATGTTCGGCGCGATGGGTTTTGGCGGCAGGG
 V  E  L  S  G  Q  K  H  V  F  M  F  G  A  M  G  F  G  G  R
     2230                2250                2270
GCGCGTATGCCTTGGATTTAAGCAAAATCAACGGAAATTATCCGGCCGCCGCCCCCCTGT
 G  A  Y  A  L  D  L  S  K  I  N  G  N  Y  P  A  A  A  P  L
     2290                2310                2330
TTGATGTCAAAGATGGCGATAATAACGGCAAAAATCGCGTGAAAGTGGAATTAGGCTACA
 F  D  V  K  D  G  D  N  N  G  K  N  R  V  K  V  E  L  G  Y
     2350                2370                2390
CCGTCGGTACGCCGCAAATCGGCAAAATCCGCAACGGCAAATACGCCGCCTTCCTCGCCT
 T  V  G  T  P  Q  I  G  K  I  R  N  G  K  Y  A  A  F  L  A
     2410                2430                2450
CCGGTTATGCGGCTAAAAAAATTGACGACTCAACAAATAAAACCGCGCTGTATGTATATG
 S  G  Y  A  A  K  K  I  D  D  S  T  N  K  T  A  L  Y  V  Y
     2470                2490                2510
ATTTGAAAGACACCTTAGGTACGCCGATTGCAAAAATCGAAGTGAAGGACGGCAAAGGCG
 D  L  K  D  T  L  G  T  P  I  A  K  I  E  V  K  D  G  K  G
     2530                2550                2570
GGCTTTCGTCCCCCACGCTGGTGGATAAAGATTTGGACGGCACGGTCGATATCGCCTATG
 G  L  S  S  P  T  L  V  D  K  D  L  D  G  T  V  D  I  A  Y
     2590                2610                2630
CCGGCGACCGGGGCGGCAATATGTACCGCTTTGATTTGAGCAATTCCGATTCTAGTAAAT
 A  G  D  R  G  G  N  M  Y  R  F  D  L  S  N  S  D  S  S  K
     2650                2670                2690
GGTCTGCAAAGGTTATTTTCGAAGGCGACAAGCCGATTACCTCCGCGCCCGCCGTTTCCC
 W  S  A  K  V  I  F  E  G  D  K  P  I  T  S  A  P  A  V  S
     2710                2730                2750
GACTGGCAGACAAACGCGTCGTCATCTTCGGTACGGGCAGCGATTTGACCGAAGATGATG
 R  L  A  D  K  R  V  V  I  F  G  T  G  S  D  L  T  E  D  D
     2770                2790                2810
TACTGAATACGGGCGAACAATATATTTACGGTATCTTTGACGACGATAAGGGGACGGTTA
 V  L  N  T  G  E  Q  Y  I  Y  G  I  F  D  D  D  K  G  T  V
```

FIG. 5C

```
                  2830                  2850                  2870
AGGTAACGGTACAAAACGGCACGGCAGGCGGGCTGCTCGAGCAACACCTTACTCAGGAAA
 K   V   T   V   Q   N   G   T   A   G   G   L   L   E   Q   H   L   T   Q   E
            2890                  2910                  2930
ATAAAACATTATTCCTGAACAAGAGATCCGACGGTTCGGGCAGCAAGGGCTGGGCGGTGA
 N   K   T   L   F   L   N   K   R   S   D   G   S   G   S   K   G   W   A   V
                  2950                  2970                  2990
AATTGAGGGAAGGAGAACGCGTTACCGTCAAACCGACCGTGGTATTGCGTACCGCCTTCG
 K   L   R   E   G   E   R   V   T   V   K   P   T   V   V   L   R   T   A   F
            3010                  3030                  3050
TAACCATCCGCAAATATAACGACGGCGGCTGCGGCGCGGAAACCGCCATTTTGGGCATCA
 V   T   I   R   K   Y   N   D   G   G   C   G   A   E   T   A   I   L   G   I
                  3070                  3090                  3110
ATACCGCCGACGGCGGCGCATTGACTCCGAGAAGCGCGCGCCCGATTGTGCCGGATCACA
 N   T   A   D   G   G   A   L   T   P   R   S   A   R   P   I   V   P   D   H
            3130                  3150                  3170
ATTCGGTTGCGCAATATTCCGGCCATAAGACAACCTCCAAAGGCAAATCCATCCCTATAG
 N   S   V   A   Q   Y   S   G   H   K   T   T   S   K   G   K   S   I   P   I
                  3190                  3210                  3230
GTTGTATGGACAAAGACGGTAAAACCGTCTGCCCGAACGGATATGTTTACGACAAGCCGG
 G   C   M   D   K   D   G   K   T   V   C   P   N   G   Y   V   Y   D   K   P
            3250                  3270                  3290
TTAATGTGCGTTATCTGGATGAAACGGAAACAGACGGATTTTCAACGACGGCGGACGGCG
 V   N   V   R   Y   L   D   E   T   E   T   D   G   F   S   T   T   A   D   G
                  3310                  3330                  3350
ATGCGGGCGGCAGCGGTATAGACCCCGCCGGCAGGCGTCCCGGCAAAAACAACCGCTGCT
 D   A   G   G   S   G   I   D   P   A   G   R   R   P   G   K   N   N   R   C
            3370                  3390                  3410
TCTCCAAAAAGGGGTGCGCACCCTGCTGATGAACGATTTGGACAGCTTGGATATTACCG
 F   S   K   K   G   V   R   T   L   L   M   N   D   L   D   S   L   D   I   T
                  3430                  3450                  3470
GCCCGATGTGCGGTATCAAACGCTTAAGCTGGCGCGAAGTCTTCTTCTGACCGGCCTGCG
 G   P   M   C   G   I   K   R   L   S   W   R   E   V   F   F   *
            3490                  3510                  3530
CGGCCGGTTTTCCGCAAATGCCGTCCGAAAGGCCTTCGGACGGCATTTTTTTGCGTTTT
       3550
TCGGGAGGGGGGCGGCAAATGAAACG
```

FIG. 5D

```
                                                                                          sequenced
                                                                                           clones
         136                                                      236
          ↓                                                        ↓
MS11  1a CATACCGGGCTTTATGCCGCCATCTTGATGTTTTCCCATACCGGCGGGGGGGGGG   CGATGGCGCAAACCCATCAATACGCTATTATCATGAACGAGCGA         12G  11
      1b CATACCGGGCTTTATGCCGCCATCTTGATGTTTTCCCATACCGGCGGGGGGGGGGG  CGATGGCGCAAACCCATCAATACGCTATTATCATGAACGAGCGA         11G   6
      2a CATACCGGGCTTTATGCCGCCATCTTGATGTTTTCCCATACCGGCGGGGGGGGGGGG CGCAGGGCGCAAACCCGTAAATACGCTATTATCATGAACGAGCGA        13G   3
         HisThrAlaLeuTyrAlaAlaIleLeuMetPheSerHisThrGlyGlyGlyGlyAla GlnAlaGlnThrArgLysTyrAlaIleIleMetAsnGluArg
                                                                    ↑ 1  2  3  4  5  6  7  8  9  10 11 12
      2b CATACCGGGCTTTATGCCGCCATCTTGATGTTTTCCCATACCGGCGGGGGGGGGG   CGCAGGGCGCAAACCCGTAAATACGCTATTATCATGAACGAGCGA        12G   1

UM01  1c CATACCGGGCTTTATGCCGCCATCTTGATGTTTTCCCATACCGGCGGGGGGGGGGG  CGATGGCGCAAACCCATCAATACGCTATTATCATGAACGAGCGA         13G   7
         HisThrAlaLeuTyrAlaAlaIleLeuMetPheSerHisThrGlyGlyGlyGlyAla MetAlaGlnThrHisGlnTyrAlaIleIleMetAsnGluArg
                                                                    ↑
      1a CATACCGGGCTTTATGCCGCCATCTTGATGTTTTCCCATACCGGCGGGGGGGGGG   CGATGGCGCAAACCCATCAATACGCTATTATCATGAACGAGCGA         12G   1
      1b CATACCGGGCTTTATGCCGCCATCTTGATGTTTTCCCATACCGGCGGGGGGGGGGG  CGATGGCGCAAACCCATCAATACGCTATTATCATGAACGAGCGA         11G   2

765   3a CATACCGGGCTTTATGCCGCCATCTTGATGTTTTCCCATACCGGCGGGGGGGGGGG  CGATGGCGCAAAGTATAAATACGCTATTGTGATGAACGAGCGA          13G   1
         HisThrAlaLeuTyrAlaAlaIleLeuMetPheSerHisThrGlyGlyGlyGlyAla MetAlaGlnThrTyrLysTyrAlaIleValMetAsnGluArg
                                                                    ↑
      3b CATACCGGGCTTTATGCCGCCATCTTGATGTTTTCCCATACCGGCGGGGGGGGGGGGG CGATGGCGCAAAGTATAAATACGCTATTGTGATGAACGAGCGA         14G   5
      4  CATACCGGGCTTTATGCCGCCATCTTGATGTTTTCCCATACCGGCGGGGGGGGGGG  CAGGGCGCAGGGCAAACGTATAAATACGCTATTGTGATGAACGAGCGA    11G   3

605103 1a CATACCGGGCTTTATGCCGCCATCTTGATGTTTTCCCATACCGGCGGGGGGGGGGG  CGATGGCGCAAACCCATCAATACGCTATTATCATGAACGAGCGA        12G   1
       1b CATACCGGGCTTTATGCCGCCATCTTGATGTTTTCCCATACCGGCGGGGGGGGGGGG CGATGGCGCAAACCCATCAATACGCTATTATCATGAACGAGCGA        11G   8 pABJ04 1c CATACCGGGCTTTATGCCGCCATCTTGATGTTTTCCCATACCGGCGGGGGGGGGGG  CGATGGCGCAAACCCATCAATACGCTATTATCATGAACGAGCGA        13G   2
          HisThrAlaLeuTyrAlaAlaIleLeuMetPheSerHisThrGlyGlyGlyGlyAla MetAlaGlnThrHisGlnTyrAlaIleIleMetAsnGluArg

1a CATACCGGGCTTTATGCCGCCATCTTGATGTTTTCCCATACCGGCGGGGGGGGGGG  CGATGGCGCAAACCCATCAATACGCTATTATCATGAACGAGCGA        12G   7
       1b CATACCGGGCTTTATGCCGCCATCTTGATGTTTTCCCATACCGGCGGGGGGGGGGGG CGATGGCGCAAACCCATCAATACGCTATTATCATGAACGAGCGA        11G   1
       1d CATACCGGGCTTTATGCCGCCATCTTGATGTTTTCCCATACCGGCGGGGGGGGGG   CGATGGCGCAAACCCATCAATACGCTATTATCATGAACGAGCGA        10G   2
          HisThrAlaLeuTyrAlaAlaIleLeuMetPheSerHisThrGlyGlyGlyGlyAla MetAlaGlnThrHisGlnTyrAlaIleIleMetAsnGluArg
```

FIG. 6

```
CCGCTGTATG TGTATGATTT GGAAAACACC AGTGGTAGTC TGATTAAAAA AATCGAAGCA  60
CCCGGCGGCA AAGGCGGGCT TTCGTCCCCC ACGCTGGTGG ATAAAGATTT GGACGGCACG 120
GTCGATATCG CCTATGCCGG CGACCGGGGC GGCAATATGT ACCGCTTTGA TTTGAGCAAT 180
TCCGATTCTA GTAAATGGTC TGCAAAGGTT ATTTTCGAAG GCGACAAGCC GATTACCTCC 240
GCGCCCGCCG TTTCCCGACT GGCAGACAAA CGCGTGGTTA TCTTCGGCAC GGGCAGCGAT 300
TTGAGTGAAC AGGATGTACT GGATACGGAC AAACAATATA TTTACGGTAT CTTTGACGAC 360
GATAAGTCGA CGGTTAATGT AAAGGTAACA AACGGCACGG GAGGCGGGCT GCTCGAGCAA 420
GTGCTTAAAG AGGAAAGTAA AACCTTATTC CTGAGCAATA ATAAGGCATC CGGCGGATCG 480
GCCGATAAAG GGTGGGTAGT GAAATTGAGG GAAGGAGAAC GCGTTACCGT CAAACCGACC 540
GTGGTATTGC GTACCGCCTT TGTCACCATC CGCAAATATA CGGATACGGA CAAATGTGGC 600
GCGCAAACCG CCATTTTGGG CATCAATACC GCCGACGGCG GCGCATTGAC TCCGAGAAGC 660
GCGCGCCCGA TTGTGCCGGA TCACAATTCG GTTGCGCAAT ATTCCGGCCA TCAGAAAATG 720
AACGGCAAGT CCATCCCGG                                             739
```

FIG. 7

```
P   L   Y   V   Y   D   L   E   N   T   S   G   S   L   I   K
CCG CTG TAT GTG TAT GAT TTG GAA AAC ACC AGT GGT AGT CTG ATT AAA  48
K   I   E   A   P   G   G   K   G   G   L   S   S   P   T   L
AAA ATC GAA GCA CCC GGC GGC AAA GGC GGG CTT TCG TCC CCC ACG CTG  96
V   D   K   D   L   D   G   T   V   D   I   A   Y   A   G   D
GTG GAT AAA GAT TTG GAC GGC ACG GTC GAT ATC GCC TAT GCC GGC GAC 144
R   G   G   N   M   Y   R   F   D   L   S   N   S   D   S   S
CGG GGC GGC AAT ATG TAC CGC TTT GAT TTG AGC AAT TCC GAT TCT AGT 192
K   W   S   A   K   V   I   F   E   G   D   K   P   I   T   S
AAA TGG TCT GCA AAG GTT ATT TTC GAA GGC GAC AAG CCG ATT ACC TCC 240
A   P   A   V   S   R   L   A   D   K   R   V   V   I   F   G
GCG CCC GCC GTT TCC CGA CTG GCA GAC AAA CGC GTG GTT ATC TTC GGC 288
T   G   S   D   L   S   E   Q   D   V   L   D   T   D   K   Q
ACG GGC AGC GAT TTG AGT GAA CAG GAT GTA CTG GAT ACG GAC AAA CAA 336
Y   I   Y   G   I   F   D   D   D   K   S   T   V   N   V   K
TAT ATT TAC GGT ATC TTT GAC GAC GAT AAG TCG ACG GTT AAT GTA AAG 384
V   T   N   G   T   G   G   G   L   L   E   Q   V   L   K   E
GTA ACA AAC GGC ACG GGA GGC GGG CTG CTC GAG CAA GTG CTT AAA GAG 432
E   S   K   T   L   F   L   S   N   N   K   A   S   G   G   S
GAA AGT AAA ACC TTA TTC CTG AGC AAT AAT AAG GCA TCC GGC GGA TCG 480
A   D   K   G   W   V   V   K   L   R   E   G   E   R   V   T
GCC GAT AAA GGG TGG GTA GTG AAA TTG AGG GAA GGA GAA CGC GTT ACC 528
V   K   P   T   V   V   L   R   T   A   F   V   T   I   R   K
GTC AAA CCG ACC GTG GTA TTG CGT ACC GCC TTT GTC ACC ATC CGC AAA 576
Y   T   D   T   D   K   C   G   A   Q   T   A   I   L   G   I
TAT ACG GAT ACG GAC AAA TGT GGC GCG CAA ACC GCC ATT TTG GGC ATC 624
N   T   A   D   G   G   A   L   T   P   R   S   A   R   P   I
AAT ACC GCC GAC GGC GGC GCA TTG ACT CCG AGA AGC GCG CGC CCG ATT 672
V   P   D   H   N   S   V   A   Q   Y   S   G   H   Q   K   M
GTG CCG GAT CAC AAT TCG GTT GCG CAA TAT TCC GGC CAT CAG AAA ATG 720
N   G   K   S   I   P
AAC GGC AAG TCC ATC CCG G                                       739
```

FIG. 8

```
         P  L  Y  V  Y  D  L  E  N  T  S  G  S  L  I  K  K  I  E  A
    1    CCGCTGTATGTGTATGATTTGGAAAACACCAGTGGTAGTCTGATTAAAAAAATCGAAGCA
         |||||||||| |||||||||| || ||||| ||||  | ||||  ||||||||||||
    2446 GCGCTGTATGTATATGATTTGAAAGACACCTTAGGTACGCCGATTGCAAAAATCGAAGTG
         A  L  Y  V  Y  D  L  K  D  T  L  G  T  P  I  K  K  I  E  A

P  G  G  K  G  G  L  S  S  P  T  L  V  D  K  D  L  D  G  T
         CCCGGCGGCAAAGGCGGGCTTTCGTCCCCCACGCTGGTGGATAAAGATTTGGACGGCACG
         |  |||||||||||||||||||||||||||||||||||||||||||||||||||||||
         AAGGACGGCAAAGGCGGGCTTTCGTCCCCCACGCTGGTGGATAAAGATTTGGACGGCACG
         K  D  G  K  G  G  L  S  S  P  T  L  V  D  K  D  L  D  G  T

V  D  I  A  Y  A  G  D  R  G  G  N  M  Y  R  F  D  L  S  N
         GTCGATATCGCCTATGCCGGCGACCGGGGCGGCAATATGTACCGCTTTGATTTGAGCAAT
         ||||||||||||||||||||||||||||||||||||||||||||||||||||||||||||
         GTCGATATCGCCTATGCCGGCGACCGGGGCGGCAATATGTACCGCTTTGATTTGAGCAAT
         V  D  I  A  Y  A  G  D  R  G  G  N  M  Y  R  F  D  L  S  N

S  D  S  S  K  W  S  A  K  V  I  F  E  G  D  K  P  I  T  S
         TCCGATTCTAGTAAATGGTCTGCAAAGGTTATTTTCGAAGGCGACAAGCCGATTACCTCC
         ||||||||||||||||||||||||||||||||||||||||||||||||||||||||||||
         TCCGATTCTAGTAAATGGTCTGCAAAGGTTATTTTCGAAGGCGACAAGCCGATTACCTCC
         S  D  S  S  K  W  S  A  K  V  I  F  E  G  D  K  P  I  T  S

A  P  A  V  S  R  L  A  D  K  R  V  V  I  F  G  T  G  S  D
         GCGCCCGCCGTTTCCCGACTGGCAGACAAACGCGTGGTTATCTTCGGCACGGGCAGCGAT
         |||||||||||||||||||||||||||||||||||||  |||||||||  ||||||||||
         GCGCCCGCCGTTTCCCGACTGGCAGACAAACGCGTCGTCATCTTCGGTACGGGCAGCGAT
         A  P  A  V  S  R  L  A  D  K  R  V  V  I  F  G  T  G  S  D

L  S  E  Q  D  V  L  D  T  D  K  Q  Y  I  Y  G  I  F  D  D
         TTGAGTGAACAGGATGTACTGGATACGGACAAACAATATATTTACGGTATCTTTGACGAC
         ||||  |||  | |||||||||| ||||||| | ||||||||||||||||||||||||||
         TTGACCGAAGATGATGTACTGAATACGGGCGAACAATATATTTACGGTATCTTTGACGAC
         L  T  E  D  D  V  L  N  T  G  E  Q  Y  I  Y  G  I  F  D  D

D  K  S  T  V  N  V  K  V  T  N  G  T  G  G  G  L  L  E  Q
         GATAAGTCGACGGTTAATGTAAAGGTAACAAACGGCACGGGAGGCGGGCTGCTCGAGCAA
         ||||||  |||||||||  ||||  |||| ||||||||||  ||||||||||||||||||
         GATAAGGGGACGGTTAAGGTAACGGTACAAAACGGCACGGCAGGCGGGCTGCTCGAGCAA
         D  K  G  T  V  K  V  T  V  Q  N  G  T  A  G  G  L  L  E  Q

V  L  K  E  E  S  K  T  L  F  L  S  N  N  K  A  S  G  G  S
         GTGCTTAAAGAGGAAAGTAAAACCTTATTCCTGAGCAATAATAAGGCATCCGGCGGATCG
         |||   ||||||  ||||||  |||||||| ||       ||  |||  ||||| || ||
         CACCTTACTCAGGAAAATAAAACATTATTCCTG......AACAAGAGATCCGACGGTTCG
         H  L  T  Q  E  N  K  T  L  F  L           N  K  R  S  D  G  S
```

FIG. 9A

```
A   D   K   G   W   V   V   K   L   R   E   G   E   R   V   T   V   K   P   T
GCCGATAAAGGGTGGGTAGTGAAATTGAGGGAAGGAGAACGCGTTACCGTCAAACCGACC
| |    || ||  ||||   ||||||||||||||||||||||||||||||||||||||||
GGCAGCAAGGGCTGGGCGGTGAAATTGAGGGAAGGAGAACGCGTTACCGTCAAACCGACC
G   S   K   G   W   A   V   K   L   R   E   G   E   R   V   T   V   K   P   T

V   V   L   R   T   A   F   V   T   I   R   K   Y   T   D   T   D   K   C   G
GTGGTATTGCGTACCGCCTTTGTCACCATCCGCAAATATACGGATACGGACAAATGTGGC
|||||||||||||||||||||  || ||||||||||||||| ||     | |   || |||
GTGGTATTGCGTACCGCCTTCGTAACCATCCGCAAATATAACGA...CGGCGGCTGCGGC
V   V   L   R   T   A   F   V   T   I   R   K   Y   N   D           G   G   C   G

A   Q   T   A   I   L   G   I   N   T   A   D   G   G   A   L   T   P   R   S
GCGCAAACCGCCATTTTGGGCATCAATACCGCCGACGGCGGCGCATTGACTCCGAGAAGC
|||  |||||||||||||||||||||||||||||||||||||||||||||||||||||||
GCGGAAACCGCCATTTTGGGCATCAATACCGCCGACGGCGGCGCATTGACTCCGAGAAGC
A   E   T   A   I   L   G   I   N   T   A   D   G   G   A   L   T   P   R   S

A   R   P   I   V   P   D   H   N   S   V   A   Q   Y   S   G   H   Q   K   M
GCGCGCCCGATTGTGCCGGATCACAATTCGGTTGCGCAATATTCCGGCCATCAGAAAA.
|||||||||||||||||||||||||||||||||||||||||||||||||||||| ||| ||
GCGCGCCCGATTGTGCCGGATCACAATTCGGTTGCGCAATATTCCGGCCATAAGACAAC
A   R   P   I   V   P   D   H   N   S   V   A   Q   Y   S   G   H   K   T   T

N   G   K   S   I   P
..TGAACGGCAAGTCCATCCCGG   739
   ||||  |||||| ||||||||
CTCCAAAGGCAAATCCATCCCAT   3176
  S   K   G   K   S   I   P
```

FIG. 9B

SEQUENCE LISTING ( 1 ) GENERAL INFORMATION:

( i i i ) NUMBER OF SEQUENCES: 43

( 2 ) INFORMATION FOR SEQ ID NO:1:

( i ) SEQUENCE CHARACTERISTICS:
        ( A ) LENGTH: 3566 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
GATCCGCCCG  GTGCTTGGGC  GCCTTAGGGA  ACCGTTCCCT  TTGAGCCGGG  GCGGGGCAAC       60

GCGTACCGGT  TTTTGTTAAT  CCGCTATAAA  AGGCGGGCTA  TAGGGTAGGC  TTCATCCTGC      120

CAATCTCACT  GAATCCGTCA  ATTTCCGCAA  TTCAATTAAA  TACCGTCAAA  CCGATGCCGT      180

CATTCCGCGC  AGGCGGGAAT  CCGGACCGGT  CGGGCATCTG  CGGCGGTTTG  CTAAAAAACG      240

CTTTACCGTG  ATAAGTGCGC  AAAGTTAAAA  TGGGGAGGTA  AGCTTTTCAA  TCAGCAATCC      300

GGCGGGCGCG  GAATCGGGCG  GTTTACCGAA  CCCCGGCGTT  CGCGGCGCCC  GTCCCGCGAA      360

GGCAAACTTA  AGGAATAAAA  TATGAATAAA  ACTTTGAAAC  GGCAGGTTTT  CCGCCATACC      420

GCGCTTTATG  CCGCCATCTT  GATGTTTTCC  CATACCGGCG  GGGGGGGGGG  GCGATGGCGC      480

AAACCCATCA  ATACGCTATT  ATCATGAACG  AGCGAAACCA  GCCCGAGGTA  AAGCAGAATG      540

TGCCATCTTC  AATAAAGGAC  AAAGACAGGA  GGCGCGAATA  TACTTATTAT  ACGCACAGAA      600

CAGGAGCAGG  CTCTGTCTCA  TTCAACAATA  ACGATACCCT  TGTTTCCCAA  CAAAGCGGTA      660
```

-continued

| | | | | | | |
|---|---|---|---|---|---|---|
| CTGCCGTTTT | TGGCACAGCC | ACCTACCTGC | CGCCCTACGG | CAAGGTTTCC | GGTTTTGATG | 720 |
| CCGTCGCTCT | GAAAGAGCGC | AACAATGCCG | TTGATTGGAT | TCGTACCACC | CGCATCGCGC | 780 |
| TGGCAGGCTA | CTCCTACATC | GACGTCATAT | GCAGAAGCTA | CACAGGCTGT | CCCAAACTTG | 840 |
| TCTATAAAAC | CCGATTTACC | TTCGGTCAAC | AAGGGTTGAA | AAGAAAGGCA | GGCAGCAAGC | 900 |
| TGGATATATA | CGAAGACAAA | AGCCGCGAAA | ATTCGCCCAT | TTACAAATTG | TCGGATTATC | 960 |
| CTTGGTTGGG | CGTATCTTTC | AATTTGGGCA | GCGAGAATAC | CGTCCAAAAT | AGCAAATTAT | 1020 |
| TCAACAAATT | GATATCTTCT | TTTAGAGAAG | GCAATAATAA | TCAAACCATC | GTCTCTACGA | 1080 |
| CAGAAGGCAA | CCCTATTTCC | CTTGGCGACC | GGCAGCGCGA | ACATACCGCC | GTGGCCTATT | 1140 |
| ATCTGAACGC | CAAACTGCAC | CTGCTGGACA | AAAAAGGGAT | TGAAGATATC | GCCCAAGGCA | 1200 |
| AAATAGTGGA | TTTGGGTATC | TTGAAACCGC | ACGTCGAGAC | GACAGGACGA | AGCTTGCTAG | 1260 |
| ATTTTTGGGC | TAGGTGGGAC | ATTAAAGATA | CCGGGCAGAT | TCCGGTCAAG | CTCGGCCTGC | 1320 |
| CGCAAGTCAA | AGCAGGCCGC | TGCACCAACA | AACCGAACCC | CAATAATAAT | ACCAAAGCCC | 1380 |
| CTTCGCCGGC | ACTGACCGCC | CCCGCGCTGT | GGTTCGGACC | CGGGCAAGAT | GGTAAGGCGG | 1440 |
| AGATGTATTC | CGCTTCGGTT | TCCACCTACC | CCGACAGTTC | GAGCAGCCGC | ATCTTCCTCC | 1500 |
| AAGAGCTGAA | AACTCAAACC | GAACCCGGCA | AACCCGGCCG | CTATTCCCTC | AAATCTTTGA | 1560 |
| ATGATGGTGA | GATTAAAAGT | CGACAGCCGA | GTTTCAACGG | GCGGCAAACA | ATCATCCGAT | 1620 |
| TGGATGACGG | CGTACATTTG | ATCAAACTGA | ATGGAAGCAA | GGATGAGGTC | GCCGCTTTTG | 1680 |
| TCAATTTAAA | TGGAAACAAC | ACCGGCAAAA | ACGACACTTT | CGGCATTGTT | AAGGAAGCGA | 1740 |
| ACGTCAATCT | TGACGCCGAC | GAGTGGAAAA | AAGTGCTGCT | GCCTTGGACG | GTTCGGGGTC | 1800 |
| CCGATAATGA | CAATAAATTT | AAATCAATTA | ACCAAAAACC | AGAAAAATAC | AGCCAAAGAT | 1860 |
| ACCGCATCCG | CGACAACAAC | GGCAATCGCG | ATTTGGGCGA | CATCGTCAAC | AGCCCGATTG | 1920 |
| TCGCGGTCGG | CGGGTATTTG | GCAACCGCCG | CGAACGACGG | GATGGTGCAT | ATCTTCAAAA | 1980 |
| AAAACGGCGG | CAGTGATGAA | CGCAGCTACA | ATCTGAAGCT | CAGCTACATC | CCCGGCACGA | 2040 |
| TGCCGCGCAA | GGATATTCAA | AGCCAAGAAT | CCACCCTTGC | CAAAGAGCTG | CGCGCCTTTG | 2100 |
| CCGAAAAAGG | CTATGTGGGC | GACCGCTACG | GCGTGGACGG | CGGCTTTGTC | TTGCGCCAAG | 2160 |
| TCGAACTGAG | CGGGCAAAAA | CACGTGTTTA | TGTTCGGCGC | GATGGGTTTT | GGCGGCAGGG | 2220 |
| GCGCGTATGC | CTTGGATTTA | AGCAAAATCA | ACGGAAATTA | TCCGGCCGCC | GCCCCCCTGT | 2280 |
| TTGATGTCAA | AGATGGCGAT | AATAACGGCA | AAAATCGCGT | GAAAGTGGAA | TTAGGCTACA | 2340 |
| CCGTCGGTAC | GCCGCAAATC | GGCAAAATCC | GCAACGGCAA | ATACGCCGCC | TTCCTCGCCT | 2400 |
| CCGGTTATGC | GGCTAAAAAA | ATTGACGACT | CAACAAATAA | AACCGCGCTG | TATGTATATG | 2460 |
| ATTTGAAAGA | CACCTTAGGT | ACGCCGATTG | CAAAAATCGA | AGTGAAGGAC | GGCAAAGGCG | 2520 |
| GGCTTTCGTC | CCCCACGCTG | GTGGATAAAG | ATTTGGACGG | CACGGTCGAT | ATCGCCTATG | 2580 |
| CCGGCGACCG | GGGCGGCAAT | ATGTACCGCT | TGATTTGAG | CAATTCCGAT | TCTAGTAAAT | 2640 |
| GGTCTGCAAA | GGTTATTTTC | GAAGGCGACA | AGCCGATTAC | CTCCGCGCCC | GCCGTTTCCC | 2700 |
| GACTGGCAGA | CAAACGCGTC | GTCATCTTCG | GTACGGGCAG | CGATTTGACC | GAAGATGATG | 2760 |
| TACTGAATAC | GGGCGAACAA | TATATTTACG | GTATCTTTGA | CGACGATAAG | GGGACGGTTA | 2820 |
| AGGTAACGGT | ACAAAACGGC | ACGGCAGGCG | GGCTGCTCGA | GCAACACCTT | ACTCAGGAAA | 2880 |
| ATAAAACATT | ATTCCTGAAC | AAGAGATCCG | ACGGTTCGGG | CAGCAAGGGC | TGGGCGGTGA | 2940 |
| AATTGAGGGA | AGGAGAACGC | GTTACCGTCA | AACCGACCGT | GGTATTGCGT | ACCGCCTTCG | 3000 |
| TAACCATCCG | CAAATATAAC | GACGGCGGCT | GCGGCGCGGA | AACCGCCATT | TTGGGCATCA | 3060 |

| | | | | | |
|---|---|---|---|---|---|
| ATACCGCCGA | CGGCGGCGCA | TTGACTCCGA | GAAGCGCGCG | CCCGATTGTG | CCGGATCACA | 3120
| ATTCGGTTGC | GCAATATTCC | GGCCATAAGA | CAACCTCCAA | AGGCAAATCC | ATCCCTATAG | 3180
| GTTGTATGGA | CAAAGACGGT | AAAACCGTCT | GCCCGAACGG | ATATGTTTAC | GACAAGCCGG | 3240
| TTAATGTGCG | TTATCTGGAT | GAAACGGAAA | CAGACGGATT | TTCAACGACG | GCGGACGGCG | 3300
| ATGCGGGCGG | CAGCGGTATA | GACCCCGCCG | GCAGGCGTCC | CGGCAAAAAC | AACCGCTGCT | 3360
| TCTCCAAAAA | AGGGGTGCGC | ACCCTGCTGA | TGAACGATTT | GGACAGCTTG | GATATTACCG | 3420
| GCCCGATGTG | CGGTATCAAA | CGCTTAAGCT | GGCGCGAAGT | CTTCTTCTGA | CCGGCCTGCG | 3480
| CGGCCGGTTT | TTCCGCAAAT | GCCGTCCGAA | AGGCCTTCGG | ACGGCATTTT | TTTGCGTTTT | 3540
| TCGGGAGGGG | GGCGGCAAAT | GAAACG | | | | 3566

( 2 ) INFORMATION FOR SEQ ID NO:2:

( i ) SEQUENCE CHARACTERISTICS:
        ( A ) LENGTH: 3567 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 382..3470

( x i ) SEQUENCE DESCRIPTION: SEQ ID NO:2:

| | | | | | |
|---|---|---|---|---|---|
| GATCCGCCCG | GTGCTTGGGC | GCCTTAGGGA | ACCGTTCCCT | TTGAGCCGGG | GCGGGGCAAC | 60
| GCGTACCGGT | TTTTGTTAAT | CCGCTATAAA | AGGCGGGCTA | TAGGGTAGGC | TTCATCCTGC | 120
| CAATCTCACT | GAATCCGTCA | ATTTCCGCAA | TTCAATTAAA | TACCGTCAAA | CCGATGCCGT | 180
| CATTCCGCGC | AGGCGGGAAT | CCGGACCGGT | CGGGCATCTG | CGGCGGTTTG | CTAAAAAACG | 240
| CTTTACCGTG | ATAAGTGCGC | AAAGTTAAAA | TGGGGAGGTA | AGCTTTTCAA | TCAGCAATCC | 300
| GGCGGGCGCG | GAATCGGGCG | GTTACCGAAA | CCCCGGCGTT | CGCGGCGCCC | GTCCCGCGAA | 360

```
GGCAAACTTA  AGGAATAAAA T ATG AAT AAA ACT TTG AAA CGG CAG GTT TTC                411
                          Met Asn Lys Thr Leu Lys Arg Gln Val Phe
                           1               5                  10

CGC CAT ACC GCG CTT TAT GCC GCC ATC TTG ATG TTT TCC CAT ACC GGC                459
Arg His Thr Ala Leu Tyr Ala Ala Ile Leu Met Phe Ser His Thr Gly
             15                  20                  25

GGG GGG GGG GGG GCG ATG GCG CAA ACC CAT CAA TAC GCT ATT ATC ATG                507
Gly Gly Gly Gly Ala Met Ala Gln Thr His Gln Tyr Ala Ile Ile Met
         30                  35                  40

AAC GAG CGA AAC CAG CCC GAG GTA AAG CAG AAT GTG CCA TCT TCA ATA                555
Asn Glu Arg Asn Gln Pro Glu Val Lys Gln Asn Val Pro Ser Ser Ile
     45                  50                  55

AAG GAC AAA GAC AGG AGG CGC GAA TAT ACT TAT TAT ACG CAC AGA ACA                603
Lys Asp Lys Asp Arg Arg Arg Glu Tyr Thr Tyr Tyr Thr His Arg Thr
 60                  65                  70

GGA GGA GGC TCT GTC TCA TTC AAC AAT AAC GAT ACC CTT GTT TCC CAA                651
Gly Gly Gly Ser Val Ser Phe Asn Asn Asn Asp Thr Leu Val Ser Gln
 75                  80                  85                  90

CAA AGC GGT ACT GCC GTT TTT GGC ACA GCC ACC TAC CTG CCG CCC TAC                699
Gln Ser Gly Thr Ala Val Phe Gly Thr Ala Thr Tyr Leu Pro Pro Tyr
             95                 100                 105

GGC AAG GTT TCC GGT TTT GAT GCC GTC GCT CTG AAA GAG CGC AAC AAT                747
Gly Lys Val Ser Gly Phe Asp Ala Val Ala Leu Lys Glu Arg Asn Asn
        110                 115                 120

GCC GTT GAT TGG ATT CGT ACC ACC CGC ATC GCG CTG GCA GGC TAC TCC                795
```

```
Ala Val Asp Trp Ile Arg Thr Thr Arg Ile Ala Leu Ala Gly Tyr Ser
        125             130             135

TAC ATC GAC GTC ATA TGC AGA AGC TAC ACA GGC TGT CCC AAA CTT GTC      843
Tyr Ile Asp Val Ile Cys Arg Ser Tyr Thr Gly Cys Pro Lys Leu Val
        140             145             150

TAT AAA ACC CGA TTT ACC TTC GGT CAA CAA GGG TTG AAA AGA AAG GCA      891
Tyr Lys Thr Arg Phe Thr Phe Gly Gln Gln Gly Leu Lys Arg Lys Ala
155             160             165                         170

GGC AGC AAG CTG GAT ATA TAC GAA GAC AAA AGC CGC GAA AAT TCG CCC      939
Gly Ser Lys Leu Asp Ile Tyr Glu Asp Lys Ser Arg Glu Asn Ser Pro
                    175             180             185

ATT TAC AAA TTG TCG GAT TAT CCT TGG TTG GGC GTA TCT TTC AAT TTG      987
Ile Tyr Lys Leu Ser Asp Tyr Pro Trp Leu Gly Val Ser Phe Asn Leu
                190             195             200

GGC AGC GAG AAT ACC GTC CAA AAT AGC AAA TTA TTC AAC AAA TTG ATA     1035
Gly Ser Glu Asn Thr Val Gln Asn Ser Lys Leu Phe Asn Lys Leu Ile
            205             210             215

TCT TCT TTT AGA GAA GGC AAT AAT AAT CAA ACC ATC GTC TCT ACG ACA     1083
Ser Ser Phe Arg Glu Gly Asn Asn Asn Gln Thr Ile Val Ser Thr Thr
        220             225             230

GAA GGC AAC CCT ATT TCC CTT GGC GAC CGG CAG CGC GAA CAT ACC GCC     1131
Glu Gly Asn Pro Ile Ser Leu Gly Asp Arg Gln Arg Glu His Thr Ala
235             240             245             250

GTG GCC TAT TAT CTG AAC GCC AAA CTG CAC CTG CTG GAC AAA AAA GGG     1179
Val Ala Tyr Tyr Leu Asn Ala Lys Leu His Leu Leu Asp Lys Lys Gly
                255             260             265

ATT GAA GAT ATC GCC CAA GGC AAA ATA GTG GAT TTG GGT ATC TTG AAA     1227
Ile Glu Asp Ile Ala Gln Gly Lys Ile Val Asp Leu Gly Ile Leu Lys
                270             275             280

CCG CAC GTC GAG ACG ACA GGA CGA AGC TTG CTA GAT TTT TGG GCT AGG     1275
Pro His Val Glu Thr Thr Gly Arg Ser Leu Leu Asp Phe Trp Ala Arg
            285             290             295

TGG GAC ATT AAA GAT ACC GGG CAG ATT CCG GTC AAG CTC GGC CTG CCG     1323
Trp Asp Ile Lys Asp Thr Gly Gln Ile Pro Val Lys Leu Gly Leu Pro
        300             305             310

CAA GTC AAA GCA GGC CGC TGC ACC AAC AAA CCG AAC CCC AAT AAT AAT     1371
Gln Val Lys Ala Gly Arg Cys Thr Asn Lys Pro Asn Pro Asn Asn Asn
315             320             325             330

ACC AAA GCC CCT TCG CCG GCA CTG ACC GCC CCG GCG CTG TGG TTC GGA     1419
Thr Lys Ala Pro Ser Pro Ala Leu Thr Ala Pro Ala Leu Trp Phe Gly
                335             340             345

CCC GGG CAA GAT GGT AAG GCG GAG ATG TAT TCC GCT TCG GTT TCC ACC     1467
Pro Gly Gln Asp Gly Lys Ala Glu Met Tyr Ser Ala Ser Val Ser Thr
                350             355             360

TAC CCC GAC AGT TCG AGC AGC CGC ATC TTC CTC CAA GAG CTG AAA ACT     1515
Tyr Pro Asp Ser Ser Ser Ser Arg Ile Phe Leu Gln Glu Leu Lys Thr
            365             370             375

CAA ACC GAA CCC GGC AAA CCC GGC CGC TAT TCC CTC AAA TCT TTG AAT     1563
Gln Thr Glu Pro Gly Lys Pro Gly Arg Tyr Ser Leu Lys Ser Leu Asn
        380             385             390

GAT GGT GAG ATT AAA AGT CGA CAG CCG AGT TTC AAC GGG CGG CAA ACA     1611
Asp Gly Glu Ile Lys Ser Arg Gln Pro Ser Phe Asn Gly Arg Gln Thr
395             400             405             410

ATC ATC CGA TTG GAT GAC GGC GTA CAT TTG ATC AAA CTG AAT GGA AGC     1659
Ile Ile Arg Leu Asp Asp Gly Val His Leu Ile Lys Leu Asn Gly Ser
                415             420             425

AAG GAT GAG GTC GCC GCT TTT GTC AAT TTA AAT GGA AAC AAC ACC GGC     1707
Lys Asp Glu Val Ala Ala Phe Val Asn Leu Asn Gly Asn Asn Thr Gly
            430             435             440

AAA AAC GAC ACT TTC GGC ATT GTT AAG GAA GCG AAC GTC AAT CTT GAC     1755
```

```
Lys  Asn  Asp  Thr  Phe  Gly  Ile  Val  Lys  Glu  Ala  Asn  Val  Asn  Leu  Asp
          445                      450                     455

GCC  GAC  GAG  TGG  AAA  AAA  GTG  CTG  CTG  CCT  TGG  ACG  GTT  CGG  GGT  CCC      1803
Ala  Asp  Glu  Trp  Lys  Lys  Val  Leu  Leu  Pro  Trp  Thr  Val  Arg  Gly  Pro
460                      465                      470

GAT  AAT  GAC  AAT  AAA  TTT  AAA  TCA  ATT  AAC  CAA  AAA  CCA  GAA  AAA  TAC      1851
Asp  Asn  Asp  Asn  Lys  Phe  Lys  Ser  Ile  Asn  Gln  Lys  Pro  Glu  Lys  Tyr
475                      480                      485                      490

AGC  CAA  AGA  TAC  CGC  ATC  CGC  GAC  AAC  AAC  GGC  AAT  CGC  GAT  TTG  GGC      1899
Ser  Gln  Arg  Tyr  Arg  Ile  Arg  Asp  Asn  Asn  Gly  Asn  Arg  Asp  Leu  Gly
                    495                      500                      505

GAC  ATC  GTC  AAC  AGC  CCG  ATT  GTC  GCG  GTC  GGG  TAT  TTG  GCA  ACC           1947
Asp  Ile  Val  Asn  Ser  Pro  Ile  Val  Ala  Val  Gly  Gly  Tyr  Leu  Ala  Thr
               510                      515                      520

GCC  GCG  AAC  GAC  GGG  ATG  GTG  CAT  ATC  TTC  AAA  AAA  AAC  GGC  GGC  AGT      1995
Ala  Ala  Asn  Asp  Gly  Met  Val  His  Ile  Phe  Lys  Lys  Asn  Gly  Gly  Ser
          525                      530                      535

GAT  GAA  CGC  AGC  TAC  AAT  CTG  AAG  CTC  AGC  TAC  ATC  CCC  GGC  ACG  ATG      2043
Asp  Glu  Arg  Ser  Tyr  Asn  Leu  Lys  Leu  Ser  Tyr  Ile  Pro  Gly  Thr  Met
540                      545                      550

CCG  CGC  AAG  GAT  ATT  CAA  AGC  CAA  GAA  TCC  ACC  CTT  GCC  AAA  GAG  CTG      2091
Pro  Arg  Lys  Asp  Ile  Gln  Ser  Gln  Glu  Ser  Thr  Leu  Ala  Lys  Glu  Leu
555                      560                      565                      570

CGC  GCC  TTT  GCC  GAA  AAA  GGC  TAT  GTG  GGC  GAC  CGC  TAC  GGC  GTG  GAC      2139
Arg  Ala  Phe  Ala  Glu  Lys  Gly  Tyr  Val  Gly  Asp  Arg  Tyr  Gly  Val  Asp
                    575                      580                      585

GGC  GGC  TTT  GTC  TTG  CGC  CAA  GTC  GAA  CTG  AGC  GGG  CAA  AAA  CAC  GTG      2187
Gly  Gly  Phe  Val  Leu  Arg  Gln  Val  Glu  Leu  Ser  Gly  Gln  Lys  His  Val
               590                      595                      600

TTT  ATG  TTC  GGC  GCG  ATG  GGT  TTT  GGC  GGC  AGG  GGC  GCG  TAT  GCC  TTG      2235
Phe  Met  Phe  Gly  Ala  Met  Gly  Phe  Gly  Gly  Arg  Gly  Ala  Tyr  Ala  Leu
          605                      610                      615

GAT  TTA  AGC  AAA  ATC  AAC  GGA  AAT  TAT  CCG  GCC  GCC  GCC  CCC  CTG  TTT      2283
Asp  Leu  Ser  Lys  Ile  Asn  Gly  Asn  Tyr  Pro  Ala  Ala  Ala  Pro  Leu  Phe
620                      625                      630

GAT  GTC  AAA  GAT  GGC  GAT  AAT  AAC  GGC  AAA  AAT  CGC  GTG  AAA  GTG  GAA      2331
Asp  Val  Lys  Asp  Gly  Asp  Asn  Asn  Gly  Lys  Asn  Arg  Val  Lys  Val  Glu
635                      640                      645                      650

TTA  GGC  TAC  ACC  GTC  GGT  ACG  CCG  CAA  ATC  GGC  AAA  ATC  CGC  AAC  GGC      2379
Leu  Gly  Tyr  Thr  Val  Gly  Thr  Pro  Gln  Ile  Gly  Lys  Ile  Arg  Asn  Gly
                    655                      660                      665

AAA  TAC  GCC  GCC  TTC  CTC  GCC  TCC  GGT  TAT  GCG  GCT  AAA  AAA  ATT  GAC      2427
Lys  Tyr  Ala  Ala  Phe  Leu  Ala  Ser  Gly  Tyr  Ala  Ala  Lys  Lys  Ile  Asp
               670                      675                      680

GAC  TCA  ACA  AAT  AAA  ACC  GCG  CTG  TAT  GTA  TAT  GAT  TTG  AAA  GAC  ACC      2475
Asp  Ser  Thr  Asn  Lys  Thr  Ala  Leu  Tyr  Val  Tyr  Asp  Leu  Lys  Asp  Thr
          685                      690                      695

TTA  GGT  ACG  CCG  ATT  GCA  AAA  ATC  GAA  GTG  AAG  GAC  GGC  AAA  GGC  GGG      2523
Leu  Gly  Thr  Pro  Ile  Ala  Lys  Ile  Glu  Val  Lys  Asp  Gly  Lys  Gly  Gly
          700                      705                      710

CTT  TCG  TCC  CCC  ACG  CTG  GTG  GAT  AAA  GAT  TTG  GAC  GGC  ACG  GTC  GAT      2571
Leu  Ser  Ser  Pro  Thr  Leu  Val  Asp  Lys  Asp  Leu  Asp  Gly  Thr  Val  Asp
715                      720                      725                      730

ATC  GCC  TAT  GCC  GGC  GAC  CGG  GGC  GGC  AAT  ATG  TAC  CGC  TTT  GAT  TTG      2619
Ile  Ala  Tyr  Ala  Gly  Asp  Arg  Gly  Gly  Asn  Met  Tyr  Arg  Phe  Asp  Leu
                    735                      740                      745

AGC  AAT  TCC  GAT  TCT  AGT  AAA  TGG  TCT  GCA  AAG  GTT  ATT  TTC  GAA  GGC      2667
Ser  Asn  Ser  Asp  Ser  Ser  Lys  Trp  Ser  Ala  Lys  Val  Ile  Phe  Glu  Gly
          750                      755                      760

GAC  AAG  CCG  ATT  ACC  TCC  GCG  CCC  GCC  GTT  TCC  CGA  CTG  GCA  GAC  AAA      2715
```

|     |     |     |     |     |     |     |     |     |     |     |     |     |     |     |      |
|-----|-----|-----|-----|-----|-----|-----|-----|-----|-----|-----|-----|-----|-----|-----|------|
| Asp | Lys | Pro | Ile | Thr | Ser | Ala | Pro | Ala | Val | Ser | Arg | Leu | Ala | Asp | Lys  |
|     | 765 |     |     |     |     | 770 |     |     |     |     | 775 |     |     |     |      |

| CGC | GTC | GTC | ATC | TTC | GGT | ACG | GGC | AGC | GAT | TTG | ACC | GAA | GAT | GAT | GTA | 2763 |
|-----|-----|-----|-----|-----|-----|-----|-----|-----|-----|-----|-----|-----|-----|-----|-----|------|
| Arg | Val | Val | Ile | Phe | Gly | Thr | Gly | Ser | Asp | Leu | Thr | Glu | Asp | Asp | Val |      |
|     | 780 |     |     |     |     | 785 |     |     |     |     | 790 |     |     |     |     |      |

| CTG | AAT | ACG | GGC | GAA | CAA | TAT | ATT | TAC | GGT | ATC | TTT | GAC | GAC | GAT | AAG | 2811 |
|-----|-----|-----|-----|-----|-----|-----|-----|-----|-----|-----|-----|-----|-----|-----|-----|------|
| Leu | Asn | Thr | Gly | Glu | Gln | Tyr | Ile | Tyr | Gly | Ile | Phe | Asp | Asp | Asp | Lys |      |
| 795 |     |     |     |     | 800 |     |     |     |     | 805 |     |     |     |     | 810 |      |

| GGG | ACG | GTT | AAG | GTA | ACG | GTA | CAA | AAC | GGC | ACG | GCA | GGC | GGG | CTG | CTC | 2859 |
|-----|-----|-----|-----|-----|-----|-----|-----|-----|-----|-----|-----|-----|-----|-----|-----|------|
| Gly | Thr | Val | Lys | Val | Thr | Val | Gln | Asn | Gly | Thr | Ala | Gly | Gly | Leu | Leu |      |
|     |     |     |     | 815 |     |     |     |     | 820 |     |     |     |     | 825 |     |      |

| GAG | CAA | CAC | CTT | ACT | CAG | GAA | AAT | AAA | ACA | TTA | TTC | CTG | AAC | AAG | AGA | 2907 |
|-----|-----|-----|-----|-----|-----|-----|-----|-----|-----|-----|-----|-----|-----|-----|-----|------|
| Glu | Gln | His | Leu | Thr | Gln | Glu | Asn | Lys | Thr | Leu | Phe | Leu | Asn | Lys | Arg |      |
|     |     |     | 830 |     |     |     |     | 835 |     |     |     |     | 840 |     |     |      |

| TCC | GAC | GGT | TCG | GGC | AGC | AAG | GGC | TGG | GCG | GTG | AAA | TTG | AGG | GAA | GGA | 2955 |
|-----|-----|-----|-----|-----|-----|-----|-----|-----|-----|-----|-----|-----|-----|-----|-----|------|
| Ser | Asp | Gly | Ser | Gly | Ser | Lys | Gly | Trp | Ala | Val | Lys | Leu | Arg | Glu | Gly |      |
|     |     | 845 |     |     |     |     | 850 |     |     |     |     | 855 |     |     |     |      |

| GAA | CGC | GTT | ACC | GTC | AAA | CCG | ACC | GTG | GTA | TTG | CGT | ACC | GCC | TTC | GTA | 3003 |
|-----|-----|-----|-----|-----|-----|-----|-----|-----|-----|-----|-----|-----|-----|-----|-----|------|
| Glu | Arg | Val | Thr | Val | Lys | Pro | Thr | Val | Val | Leu | Arg | Thr | Ala | Phe | Val |      |
|     | 860 |     |     |     |     | 865 |     |     |     |     | 870 |     |     |     |     |      |

| ACC | ATC | CGC | AAA | TAT | AAC | GAC | GGC | GGC | TGC | GGC | GCG | GAA | ACC | GCC | ATT | 3051 |
|-----|-----|-----|-----|-----|-----|-----|-----|-----|-----|-----|-----|-----|-----|-----|-----|------|
| Thr | Ile | Arg | Lys | Tyr | Asn | Asp | Gly | Gly | Cys | Gly | Ala | Glu | Thr | Ala | Ile |      |
| 875 |     |     |     |     | 880 |     |     |     |     | 885 |     |     |     |     | 890 |      |

| TTG | GGC | ATC | AAT | ACC | GCC | GAC | GGC | GGC | GCA | TTG | ACT | CCG | AGA | AGC | GCG | 3099 |
|-----|-----|-----|-----|-----|-----|-----|-----|-----|-----|-----|-----|-----|-----|-----|-----|------|
| Leu | Gly | Ile | Asn | Thr | Ala | Asp | Gly | Gly | Ala | Leu | Thr | Pro | Arg | Ser | Ala |      |
|     |     |     |     | 895 |     |     |     |     | 900 |     |     |     |     | 905 |     |      |

| CGC | CCG | ATT | GTG | CCG | GAT | CAC | AAT | TCG | GTT | GCG | CAA | TAT | TCC | GGC | CAT | 3147 |
|-----|-----|-----|-----|-----|-----|-----|-----|-----|-----|-----|-----|-----|-----|-----|-----|------|
| Arg | Pro | Ile | Val | Pro | Asp | His | Asn | Ser | Val | Ala | Gln | Tyr | Ser | Gly | His |      |
|     |     |     | 910 |     |     |     |     | 915 |     |     |     |     | 920 |     |     |      |

| AAG | ACA | ACC | TCC | AAA | GGC | AAA | TCC | ATC | CCT | ATA | GGT | TGT | ATG | GAC | AAA | 3195 |
|-----|-----|-----|-----|-----|-----|-----|-----|-----|-----|-----|-----|-----|-----|-----|-----|------|
| Lys | Thr | Thr | Ser | Lys | Gly | Lys | Ser | Ile | Pro | Ile | Gly | Cys | Met | Asp | Lys |      |
|     |     | 925 |     |     |     |     | 930 |     |     |     |     | 935 |     |     |     |      |

| GAC | GGT | AAA | ACC | GTC | TGC | CCG | AAC | GGA | TAT | GTT | TAC | GAC | AAG | CCG | GTT | 3243 |
|-----|-----|-----|-----|-----|-----|-----|-----|-----|-----|-----|-----|-----|-----|-----|-----|------|
| Asp | Gly | Lys | Thr | Val | Cys | Pro | Asn | Gly | Tyr | Val | Tyr | Asp | Lys | Pro | Val |      |
|     | 940 |     |     |     |     | 945 |     |     |     |     | 950 |     |     |     |     |      |

| AAT | GTG | CGT | TAT | CTG | GAT | GAA | ACG | GAA | ACA | GAC | GGA | TTT | TCA | ACG | ACG | 3291 |
|-----|-----|-----|-----|-----|-----|-----|-----|-----|-----|-----|-----|-----|-----|-----|-----|------|
| Asn | Val | Arg | Tyr | Leu | Asp | Glu | Thr | Glu | Thr | Asp | Gly | Phe | Ser | Thr | Thr |      |
| 955 |     |     |     |     | 960 |     |     |     |     | 965 |     |     |     |     | 970 |      |

| GCG | GAC | GGC | GAT | GCG | GGC | GGC | AGC | GGT | ATA | GAC | CCC | GCC | GGC | AGG | CGT | 3339 |
|-----|-----|-----|-----|-----|-----|-----|-----|-----|-----|-----|-----|-----|-----|-----|-----|------|
| Ala | Asp | Gly | Asp | Ala | Gly | Gly | Ser | Gly | Ile | Asp | Pro | Ala | Gly | Arg | Arg |      |
|     |     |     |     | 975 |     |     |     |     | 980 |     |     |     |     | 985 |     |      |

| CCC | GGC | AAA | AAC | AAC | CGC | TGC | TTC | TCC | AAA | AAA | GGG | GTG | CGC | ACC | CTG | 3387 |
|-----|-----|-----|-----|-----|-----|-----|-----|-----|-----|-----|-----|-----|-----|-----|-----|------|
| Pro | Gly | Lys | Asn | Asn | Arg | Cys | Phe | Ser | Lys | Lys | Gly | Val | Arg | Thr | Leu |      |
|     |     |     | 990 |     |     |     |     | 995 |     |     |     |     | 1000|     |     |      |

| CTG | ATG | AAC | GAT | TTG | GAC | AGC | TTG | GAT | ATT | ACC | GGC | CCG | ATG | TGC | GGT | 3435 |
|-----|-----|-----|-----|-----|-----|-----|-----|-----|-----|-----|-----|-----|-----|-----|-----|------|
| Leu | Met | Asn | Asp | Leu | Asp | Ser | Leu | Asp | Ile | Thr | Gly | Pro | Met | Cys | Gly |      |
|     |     | 1005|     |     |     |     | 1010|     |     |     |     | 1015|     |     |     |      |

| ATC | AAA | CGC | TTA | AGC | TGG | CGC | GAA | GTC | TTC | TTC | TG ACCGGCTGC | 3480 |
|-----|-----|-----|-----|-----|-----|-----|-----|-----|-----|-----|--------------|------|
| Ile | Lys | Arg | Leu | Ser | Trp | Arg | Glu | Val | Phe | Phe |              |      |
|     | 1020|     |     |     |     | 1025|     |     |     |     |              |      |

| GCGGCCGGTT | TTTCCGCAAA | TGCCGTCCGA | AAGGCCTTCG | GACGGCATTT | TTTTGCGTTT | 3540 |
|------------|------------|------------|------------|------------|------------|------|

| TTCGGGAGGG | GGGCGGCAAA | TGAAACG | 3567 |
|------------|------------|---------|------|

( 2 ) INFORMATION FOR SEQ ID NO:3:

( i ) SEQUENCE CHARACTERISTICS:
        ( A ) LENGTH: 1029 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| Met | Asn | Lys | Thr | Leu | Lys | Arg | Gln | Val | Phe | Arg | His | Thr | Ala | Leu | Tyr |
|---|---|---|---|---|---|---|---|---|---|---|---|---|---|---|---|
| 1 | | | | 5 | | | | | 10 | | | | | 15 | |

| Ala | Ala | Ile | Leu | Met | Phe | Ser | His | Thr | Gly | Gly | Gly | Gly | Gly | Ala | Met |
| | | | 20 | | | | | 25 | | | | | 30 | | |

| Ala | Gln | Thr | His | Gln | Tyr | Ala | Ile | Ile | Met | Asn | Glu | Arg | Asn | Gln | Pro |
| | | 35 | | | | | | 40 | | | | 45 | | | |

| Glu | Val | Lys | Gln | Asn | Val | Pro | Ser | Ser | Ile | Lys | Asp | Lys | Asp | Arg | Arg |
| | 50 | | | | | 55 | | | | | 60 | | | | |

| Arg | Glu | Tyr | Thr | Tyr | Tyr | Thr | His | Arg | Thr | Gly | Gly | Gly | Ser | Val | Ser |
| 65 | | | | | 70 | | | | 75 | | | | | | 80 |

| Phe | Asn | Asn | Asn | Asp | Thr | Leu | Val | Ser | Gln | Ser | Gly | Thr | Ala | Val |
| | | | | 85 | | | | | 90 | | | | | 95 |

| Phe | Gly | Thr | Ala | Thr | Tyr | Leu | Pro | Pro | Tyr | Gly | Lys | Val | Ser | Gly | Phe |
| | | | | 100 | | | | | 105 | | | | | 110 | |

| Asp | Ala | Val | Ala | Leu | Lys | Glu | Arg | Asn | Asn | Ala | Val | Asp | Trp | Ile | Arg |
| | | | 115 | | | | | 120 | | | | | 125 | | |

| Thr | Thr | Arg | Ile | Ala | Leu | Ala | Gly | Tyr | Ser | Tyr | Ile | Asp | Val | Ile | Cys |
| | 130 | | | | | 135 | | | | | 140 | | | | |

| Arg | Ser | Tyr | Thr | Gly | Cys | Pro | Lys | Leu | Val | Tyr | Lys | Thr | Arg | Phe | Thr |
| 145 | | | | | 150 | | | | | 155 | | | | | 160 |

| Phe | Gly | Gln | Gln | Gly | Leu | Lys | Arg | Lys | Ala | Gly | Ser | Lys | Leu | Asp | Ile |
| | | | | 165 | | | | | 170 | | | | | 175 | |

| Tyr | Glu | Asp | Lys | Ser | Arg | Glu | Asn | Ser | Pro | Ile | Tyr | Lys | Leu | Ser | Asp |
| | | | 180 | | | | | 185 | | | | | 190 | | |

| Tyr | Pro | Trp | Leu | Gly | Val | Ser | Phe | Asn | Leu | Gly | Ser | Glu | Asn | Thr | Val |
| | | 195 | | | | | 200 | | | | | 205 | | | |

| Gln | Asn | Ser | Lys | Leu | Phe | Asn | Lys | Leu | Ile | Ser | Ser | Phe | Arg | Glu | Gly |
| | 210 | | | | | 215 | | | | | 220 | | | | |

| Asn | Asn | Asn | Gln | Thr | Ile | Val | Ser | Thr | Thr | Glu | Gly | Asn | Pro | Ile | Ser |
| 225 | | | | | 230 | | | | | 235 | | | | | 240 |

| Leu | Gly | Asp | Arg | Gln | Arg | Glu | His | Thr | Ala | Val | Ala | Tyr | Tyr | Leu | Asn |
| | | | | 245 | | | | | 250 | | | | | 255 | |

| Ala | Lys | Leu | His | Leu | Leu | Asp | Lys | Lys | Gly | Ile | Glu | Asp | Ile | Ala | Gln |
| | | | 260 | | | | | 265 | | | | | 270 | | |

| Gly | Lys | Ile | Val | Asp | Leu | Gly | Ile | Leu | Lys | Pro | His | Val | Glu | Thr | Thr |
| | | 275 | | | | | 280 | | | | | 285 | | | |

| Gly | Arg | Ser | Leu | Leu | Asp | Phe | Trp | Ala | Arg | Trp | Asp | Ile | Lys | Asp | Thr |
| | 290 | | | | | 295 | | | | | 300 | | | | |

| Gly | Gln | Ile | Pro | Val | Lys | Leu | Gly | Leu | Pro | Gln | Val | Lys | Ala | Gly | Arg |
| 305 | | | | | 310 | | | | | 315 | | | | | 320 |

| Cys | Thr | Asn | Lys | Pro | Asn | Pro | Asn | Asn | Thr | Lys | Ala | Pro | Ser | Pro |
| | | | | 325 | | | | | 330 | | | | | 335 |

| Ala | Leu | Thr | Ala | Pro | Ala | Leu | Trp | Phe | Gly | Pro | Gly | Gln | Asp | Gly | Lys |
| | | | 340 | | | | | 345 | | | | | 350 | | |

| Ala | Glu | Met | Tyr | Ser | Ala | Ser | Val | Ser | Thr | Tyr | Pro | Asp | Ser | Ser | Ser |
| | | 355 | | | | | 360 | | | | | 365 | | | |

| Ser | Arg | Ile | Phe | Leu | Gln | Glu | Leu | Lys | Thr | Gln | Thr | Glu | Pro | Gly | Lys |
| | 370 | | | | | 375 | | | | | 380 | | | | |

| Pro | Gly | Arg | Tyr | Ser | Leu | Lys | Ser | Leu | Asn | Asp | Gly | Glu | Ile | Lys | Ser |
| 385 | | | | | 390 | | | | | 395 | | | | | 400 |

| Arg | Gln | Pro | Ser | Phe | Asn | Gly | Arg | Gln | Thr | Ile | Ile | Arg | Leu | Asp | Asp |
| | | | | 405 | | | | | 410 | | | | | 415 | |

```
Gly Val His Leu Ile Lys Leu Asn Gly Ser Lys Asp Glu Val Ala Ala
        420                 425                 430

Phe Val Asn Leu Asn Gly Asn Asn Thr Gly Lys Asn Asp Thr Phe Gly
        435                 440                 445

Ile Val Lys Glu Ala Asn Val Asn Leu Asp Ala Asp Glu Trp Lys Lys
    450                 455                 460

Val Leu Leu Pro Trp Thr Val Arg Gly Pro Asp Asn Asp Asn Lys Phe
465                 470                 475                 480

Lys Ser Ile Asn Gln Lys Pro Glu Lys Tyr Ser Gln Arg Tyr Arg Ile
                485                 490                 495

Arg Asp Asn Asn Gly Asn Arg Asp Leu Gly Asp Ile Val Asn Ser Pro
            500                 505                 510

Ile Val Ala Val Gly Gly Tyr Leu Ala Thr Ala Ala Asn Asp Gly Met
        515                 520                 525

Val His Ile Phe Lys Lys Asn Gly Ser Asp Glu Arg Ser Tyr Asn
    530                 535                 540

Leu Lys Leu Ser Tyr Ile Pro Gly Thr Met Pro Arg Lys Asp Ile Gln
545                 550                 555                 560

Ser Gln Glu Ser Thr Leu Ala Lys Glu Leu Arg Ala Phe Ala Glu Lys
                565                 570                 575

Gly Tyr Val Gly Asp Arg Tyr Gly Asp Gly Phe Val Leu Arg
            580                 585                 590

Gln Val Glu Leu Ser Gly Gln Lys His Val Phe Met Phe Gly Ala Met
        595                 600                 605

Gly Phe Gly Gly Arg Gly Ala Tyr Ala Leu Asp Leu Ser Lys Ile Asn
    610                 615                 620

Gly Asn Tyr Pro Ala Ala Ala Pro Leu Phe Asp Val Lys Asp Gly Asp
625                 630                 635                 640

Asn Asn Gly Lys Asn Arg Val Lys Val Glu Leu Gly Tyr Thr Val Gly
            645                 650                 655

Thr Pro Gln Ile Gly Lys Ile Arg Asn Gly Lys Tyr Ala Ala Phe Leu
        660                 665                 670

Ala Ser Gly Tyr Ala Ala Lys Lys Ile Asp Asp Ser Thr Asn Lys Thr
        675                 680                 685

Ala Leu Tyr Val Tyr Asp Leu Lys Asp Thr Leu Gly Thr Pro Ile Ala
    690                 695                 700

Lys Ile Glu Val Lys Asp Gly Lys Gly Gly Leu Ser Ser Pro Thr Leu
705                 710                 715                 720

Val Asp Lys Asp Leu Asp Gly Thr Val Asp Ile Ala Tyr Ala Gly Asp
                725                 730                 735

Arg Gly Gly Asn Met Tyr Arg Phe Asp Leu Ser Asn Ser Asp Ser Ser
            740                 745                 750

Lys Trp Ser Ala Lys Val Ile Phe Glu Gly Asp Lys Pro Ile Thr Ser
        755                 760                 765

Ala Pro Ala Val Ser Arg Leu Ala Asp Lys Arg Val Val Ile Phe Gly
    770                 775                 780

Thr Gly Ser Asp Leu Thr Glu Asp Asp Val Leu Asn Thr Gly Glu Gln
785                 790                 795                 800

Tyr Ile Tyr Gly Ile Phe Asp Asp Asp Lys Gly Thr Val Lys Val Thr
                805                 810                 815

Val Gln Asn Gly Thr Ala Gly Gly Leu Leu Glu Gln His Leu Thr Gln
            820                 825                 830

Glu Asn Lys Thr Leu Phe Leu Asn Lys Arg Ser Asp Gly Ser Gly Ser
```

|  |  |  | 835 |  |  |  |  | 840 |  |  |  |  | 845 |  |
|---|---|---|---|---|---|---|---|---|---|---|---|---|---|---|
| Lys | Gly | Trp | Ala | Val | Lys | Leu | Arg | Glu | Gly | Glu | Arg | Val | Thr | Val | Lys |
|  | 850 |  |  |  |  | 855 |  |  |  |  | 860 |  |  |  |
| Pro | Thr | Val | Val | Leu | Arg | Thr | Ala | Phe | Val | Thr | Ile | Arg | Lys | Tyr | Asn |
| 865 |  |  |  |  | 870 |  |  |  |  | 875 |  |  |  |  | 880 |
| Asp | Gly | Gly | Cys | Gly | Ala | Glu | Thr | Ala | Ile | Leu | Gly | Ile | Asn | Thr | Ala |
|  |  |  |  | 885 |  |  |  |  | 890 |  |  |  |  | 895 |  |
| Asp | Gly | Gly | Ala | Leu | Thr | Pro | Arg | Ser | Ala | Arg | Pro | Ile | Val | Pro | Asp |
|  |  |  | 900 |  |  |  |  | 905 |  |  |  |  | 910 |  |  |
| His | Asn | Ser | Val | Ala | Gln | Tyr | Ser | Gly | His | Lys | Thr | Thr | Ser | Lys | Gly |
|  |  | 915 |  |  |  |  | 920 |  |  |  |  | 925 |  |  |  |
| Lys | Ser | Ile | Pro | Ile | Gly | Cys | Met | Asp | Lys | Asp | Gly | Lys | Thr | Val | Cys |
|  | 930 |  |  |  |  | 935 |  |  |  |  | 940 |  |  |  |  |
| Pro | Asn | Gly | Tyr | Val | Tyr | Asp | Lys | Pro | Val | Asn | Val | Arg | Tyr | Leu | Asp |
| 945 |  |  |  |  | 950 |  |  |  |  | 955 |  |  |  |  | 960 |
| Glu | Thr | Glu | Thr | Asp | Gly | Phe | Ser | Thr | Thr | Ala | Asp | Gly | Asp | Ala | Gly |
|  |  |  |  | 965 |  |  |  |  | 970 |  |  |  |  | 975 |  |
| Gly | Ser | Gly | Ile | Asp | Pro | Ala | Gly | Arg | Arg | Pro | Gly | Lys | Asn | Asn | Arg |
|  |  |  | 980 |  |  |  |  | 985 |  |  |  |  | 990 |  |  |
| Cys | Phe | Ser | Lys | Lys | Gly | Val | Arg | Thr | Leu | Leu | Met | Asn | Asp | Leu | Asp |
|  |  | 995 |  |  |  |  | 1000 |  |  |  |  | 1005 |  |  |  |
| Ser | Leu | Asp | Ile | Thr | Gly | Pro | Met | Cys | Gly | Ile | Lys | Arg | Leu | Ser | Trp |
|  | 1010 |  |  |  |  | 1015 |  |  |  |  | 1020 |  |  |  |  |
| Arg | Glu | Val | Phe | Phe |
| 1025 |  |  |  |  |

( 2 ) INFORMATION FOR SEQ ID NO:4:

( i ) SEQUENCE CHARACTERISTICS:
        ( A ) LENGTH: 3566 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 382..504

( x i ) SEQUENCE DESCRIPTION: SEQ ID NO:4:

```
GATCCGCCCG  GTGCTTGGGC  GCCTTAGGGA  ACCGTTCCCT  TTGAGCCGGG  GCGGGGCAAC      60

GCGTACCGGT  TTTTGTTAAT  CCGCTATAAA  AGGCGGGCTA  TAGGGTAGGC  TTCATCCTGC     120

CAATCTCACT  GAATCCGTCA  ATTTCCGCAA  TTCAATTAAA  TACCGTCAAA  CCGATGCCGT     180

CATTCCGCGC  AGGCGGGAAT  CCGGACCGGT  CGGGCATCTG  CGGCGGTTTG  CTAAAAAACG     240

CTTTACCGTG  ATAAGTGCGC  AAAGTAAAA   TGGGGAGGTA  AGCTTTTCAA  TCAGCAATCC     300

GGCGGGCGCG  GAATCGGGCG  GTTTACCGAA  CCCCGGCGTT  CGCGGCGCCC  GTCCCGCGAA     360

GGCAAACTTA  AGGAATAAAA  T  ATG  AAT  AAA  ACT  TTG  AAA  CGG  CAG  GTT  TTC     411
                           Met  Asn  Lys  Thr  Leu  Lys  Arg  Gln  Val  Phe
                             1                   5                        10

CGC  CAT  ACC  GCG  CTT  TAT  GCC  GCC  ATC  TTG  ATG  TTT  TCC  CAT  ACC  GGC     459
Arg  His  Thr  Ala  Leu  Tyr  Ala  Ala  Ile  Leu  Met  Phe  Ser  His  Thr  Gly
                   15                   20                        25

GGG  GGG  GGG  GGG  CGA  TGG  CGC  AAA  CCC  ATC  AAT  ACG  CTA  TTA  TCA           504
Gly  Gly  Gly  Gly  Arg  Trp  Arg  Lys  Pro  Ile  Asn  Thr  Leu  Leu  Ser
              30                   35                        40

TGAACGAGCG  AAACCAGCCC  GAGGTAAAGC  AGAATGTGCC  ATCTTCAATA  AAGGACAAAG     564
```

```
ACAGGAGGCG CGAATATACT TATTATACGC ACAGAACAGG AGCAGGCTCT GTCTCATTCA    624
ACAATAACGA TACCCTTGTT TCCCAACAAA GCGGTACTGC CGTTTTTGGC ACAGCCACCT    684
ACCTGCCGCC CTACGGCAAG GTTTCCGGTT TTGATGCCGT CGCTCTGAAA GAGCGCAACA    744
ATGCCGTTGA TTGGATTCGT ACCACCCGCA TCGCGCTGGC AGGCTACTCC TACATCGACG    804
TCATATGCAG AAGCTACACA GGCTGTCCCA AACTTGTCTA TAAAACCCGA TTTACCTTCG    864
GTCAACAAGG GTTGAAAAGA AAGGCAGGCA GCAAGCTGGA TATATACGAA GACAAAGCC     924
GCGAAAATTC GCCCATTTAC AAATTGTCGG ATTATCCTTG GTTGGGCGTA TCTTTCAATT    984
TGGGCAGCGA GAATACCGTC CAAAATAGCA AATTATTCAA CAAATTGATA TCTTCTTTTA   1044
GAGAAGGCAA TAATAATCAA ACCATCGTCT CTACGACAGA AGGCAACCCT ATTTCCCTTG   1104
GCGACCGGCA GCGCGAACAT ACCGCCGTGG CCTATTATCT GAACGCCAAA CTGCACCTGC   1164
TGGACAAAAA AGGGATTGAA GATATCGCCC AAGGCAAAAT AGTGGATTTG GTATCTTGA    1224
AACCGCACGT CGAGACGACA GGACGAAGCT TGCTAGATTT TTGGGCTAGG TGGGACATTA   1284
AAGATACCGG GCAGATTCCG GTCAAGCTCG GCCTGCCGCA AGTCAAAGCA GGCCGCTGCA   1344
CCAACAAACC GAACCCCAAT AATAATACCA AAGCCCCTTC GCCGGCACTG ACCGCCCCCG   1404
CGCTGTGGTT CGGACCCGGG CAAGATGGTA AGGCGGAGAT GTATTCCGCT TCGGTTTCCA   1464
CCTACCCCGA CAGTTCGAGC AGCCGCATCT TCCTCCAAGA GCTGAAAACT CAAACCGAAC   1524
CCGGCAAACC CGGCCGCTAT TCCCTCAAAT CTTTGAATGA TGGTGAGATT AAAAGTCGAC   1584
AGCCGAGTTT CAACGGGCGG CAAACAATCA TCCGATTGGA TGACGGCGTA CATTTGATCA   1644
AACTGAATGG AAGCAAGGAT GAGGTCGCCG CTTTTGTCAA TTTAAATGGA ACAACACCG    1704
GCAAAAACGA CACTTTCGGC ATTGTTAAGG AAGCGAACGT CAATCTTGAC GCCGACGAGT   1764
GGAAAAAAGT GCTGCTGCCT TGGACGGTTC GGGGTCCCGA TAATGACAAT AAATTTAAAT   1824
CAATTAACCA AAAACCAGAA AAATACAGCC AAAGATACCG CATCCGCGAC AACAACGGCA   1884
ATCGCGATTT GGGCGACATC GTCAACAGCC CGATTGTCGC GGTCGGCGGG TATTTGGCAA   1944
CCGCCGCGAA CGACGGGATG GTGCATATCT TCAAAAAAA CGGCGGCAGT GATGAACGCA    2004
GCTACAATCT GAAGCTCAGC TACATCCCCG GCACGATGCC GCGCAAGGAT ATTCAAAGCC   2064
AAGAATCCAC CCTTGCCAAA GAGCTGCGCG CCTTTGCCGA AAAAGGCTAT GTGGGCGACC   2124
GCTACGGCGT GGACGGCGGC TTTGTCTTGC GCCAAGTCGA ACTGAGCGGG CAAAAACACG   2184
TGTTTATGTT CGGCGCGATG GGTTTTGGCG GCAGGGGCGC GTATGCCTTG GATTAAGCA    2244
AAATCAACGG AAATTATCCG GCCGCCGCCC CCTGTTTGA TGTCAAAGAT GGCGATAATA    2304
ACGGCAAAAA TCGCGTGAAA GTGGAATTAG GCTACACCGT CGGTACGCCG CAAATCGGCA   2364
AAATCCGCAA CGGCAAATAC GCCGCCTTCC TCGCCTCCGG TTATGCGGCT AAAAAAATTG   2424
ACGACTCAAC AAATAAAACC GCGCTGTATG TATATGATTT GAAAGACACC TTAGGTACGC   2484
CGATTGCAAA AATCGAAGTG AAGGACGGCA AAGGCGGGCT TTCGTCCCCC ACGCTGGTGG   2544
ATAAAGATTT GGACGGCACG GTCGATATCG CCTATGCCGG CGACCGGGGC GGCAATATGT   2604
ACCGCTTTGA TTTGAGCAAT TCCGATTCTA GTAAATGGTC TGCAAAGGTT ATTTTCGAAG   2664
GCGACAAGCC GATTACCTCC GCGCCCGCCG TTTCCCGACT GGCAGACAAA CGCGTCGTCA   2724
TCTTCGGTAC GGGCAGCGAT TTGACCGAAG ATGATGTACT GAATACGGGC GAACAATATA   2784
TTTACGGTAT CTTTGACGAC GATAAGGGGA CGGTTAAGGT AACGGTACAA AACGGCACGG   2844
CAGGCGGGCT GCTCGAGCAA CACCTTACTC AGGAAAATAA AACATTATTC CTGAACAAGA   2904
GATCCGACGG TTCGGGCAGC AAGGGCTGGG CGGTGAAATT GAGGGAAGGA GAACGCGTTA   2964
```

| | | | | | |
|---|---|---|---|---|---|
| CCGTCAAACC | GACCGTGGTA | TTGCGTACCG | CCTTCGTAAC | CATCCGCAAA | TATAACGACG | 3024
| GCGGCTGCGG | CGCGGAAACC | GCCATTTTGG | GCATCAATAC | CGCCGACGGC | GGCGCATTGA | 3084
| CTCCGAGAAG | CGCGCGCCCG | ATTGTGCCGG | ATCACAATTC | GGTTGCGCAA | TATTCCGGCC | 3144
| ATAAGACAAC | CTCCAAAGGC | AAATCCATCC | CTATAGGTTG | TATGGACAAA | GACGGTAAAA | 3204
| CCGTCTGCCC | GAACGGATAT | GTTACGACA | AGCCGGTTAA | TGTGCGTTAT | CTGGATGAAA | 3264
| CGGAAACAGA | CGGATTTTCA | ACGACGGCGG | ACGGCGATGC | GGGCGGCAGC | GGTATAGACC | 3324
| CCGCCGGCAG | GCGTCCCGGC | AAAAACAACC | GCTGCTTCTC | CAAAAAAGGG | GTGCGCACCC | 3384
| TGCTGATGAA | CGATTTGGAC | AGCTTGGATA | TTACCGGCCC | GATGTGCGGT | ATCAAACGCT | 3444
| TAAGCTGGCG | CGAAGTCTTC | TTCTGACCGG | CCTGCGCGGC | CGGTTTTTCC | GCAAATGCCG | 3504
| TCCGAAAGGC | CTTCGGACGG | CATTTTTTG | CGTTTTTCGG | GAGGGGGGCG | GCAAATGAAA | 3564
| CG | | | | | | 3566

(2) INFORMATION FOR SEQ ID NO:5:

(i) SEQUENCE CHARACTERISTICS:
        (A) LENGTH: 41 amino acids
        (B) TYPE: amino acid
        (D) TOPOLOGY: linear (ii) MOLECULE TYPE: protein (xi) SEQUENCE DESCRIPTION: SEQ ID NO:5:

```
Met Asn Lys Thr Leu Lys Arg Gln Val Phe Arg His Thr Ala Leu Tyr
  1               5                  10                  15
Ala Ala Ile Leu Met Phe Ser His Thr Gly Gly Gly Gly Gly Arg Trp
             20                  25                  30
Arg Lys Pro Ile Asn Thr Leu Leu Ser
             35                  40
```

(2) INFORMATION FOR SEQ ID NO:6:

(i) SEQUENCE CHARACTERISTICS:
        (A) LENGTH: 3566 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 474..3467

(xi) SEQUENCE DESCRIPTION: SEQ ID NO:6:

| | | | | | |
|---|---|---|---|---|---|
| GATCCGCCCG | GTGCTTGGGC | GCCTTAGGGA | ACCGTTCCCT | TTGAGCCGGG | GCGGGGCAAC | 60
| GCGTACCGGT | TTTTGTTAAT | CCGCTATAAA | AGGCGGGCTA | TAGGGTAGGC | TTCATCCTGC | 120
| CAATCTCACT | GAATCCGTCA | ATTTCCGCAA | TTCAATTAAA | TACCGTCAAA | CCGATGCCGT | 180
| CATTCCGCGC | AGGCGGGAAT | CCGGACCGGT | CGGGCATCTG | CGGCGGTTTG | CTAAAAAACG | 240
| CTTTACCGTG | ATAAGTGCGC | AAAGTTAAAA | TGGGGAGGTA | AGCTTTTCAA | TCAGCAATCC | 300
| GGCGGGCGCG | GAATCGGGCG | GTTTACCGAA | CCCCGGCGTT | CGCGGCGCCC | GTCCGCGAA | 360
| GGCAAACTTA | AGGAATAAAA | TATGAATAAA | ACTTTGAAAC | GGCAGGTTTT | CCGCCATACC | 420
| GCGCTTTATG | CCGCCATCTT | GATGTTTCC | CATACCGGCG | GGGGGGGGG | GCG ATG | 476 |
| | | | | | Met |
| | | | | | 1 |
| GCG CAA ACC CAT CAA TAC GCT ATT ATC ATG AAC GAG CGA AAC CAG CCC | | | | | | 524 |

| | | | | | | | | | | | | | | | | |
|---|---|---|---|---|---|---|---|---|---|---|---|---|---|---|---|---|
| | Ala | Gln | Thr | His | Gln | Tyr | Ala | Ile | Ile | Met | Asn | Glu | Arg | Asn | Gln | Pro |
| | | | | 5 | | | | | 10 | | | | | 15 | | |

| GAG | GTA | AAG | CAG | AAT | GTG | CCA | TCT | TCA | ATA | AAG | GAC | AAA | GAC | AGG | AGG | 572 |
|---|---|---|---|---|---|---|---|---|---|---|---|---|---|---|---|---|
| Glu | Val | Lys | Gln | Asn | Val | Pro | Ser | Ser | Ile | Lys | Asp | Lys | Asp | Arg | Arg | |
| | | 20 | | | | 25 | | | | | 30 | | | | | |

| CGC | GAA | TAT | ACT | TAT | TAT | ACG | CAC | AGA | ACA | GGA | GCA | GGC | TCT | GTC | TCA | 620 |
|---|---|---|---|---|---|---|---|---|---|---|---|---|---|---|---|---|
| Arg | Glu | Tyr | Thr | Tyr | Tyr | Thr | His | Arg | Thr | Gly | Ala | Gly | Ser | Val | Ser | |
| | 35 | | | | | 40 | | | | | 45 | | | | | |

| TTC | AAC | AAT | AAC | GAT | ACC | CTT | GTT | TCC | CAA | CAA | AGC | GGT | ACT | GCC | GTT | 668 |
|---|---|---|---|---|---|---|---|---|---|---|---|---|---|---|---|---|
| Phe | Asn | Asn | Asn | Asp | Thr | Leu | Val | Ser | Gln | Gln | Ser | Gly | Thr | Ala | Val | |
| 50 | | | | | 55 | | | | | 60 | | | | | 65 | |

| TTT | GGC | ACA | GCC | ACC | TAC | CTG | CCG | CCC | TAC | GGC | AAG | GTT | TCC | GGT | TTT | 716 |
|---|---|---|---|---|---|---|---|---|---|---|---|---|---|---|---|---|
| Phe | Gly | Thr | Ala | Thr | Tyr | Leu | Pro | Pro | Tyr | Gly | Lys | Val | Ser | Gly | Phe | |
| | | | | 70 | | | | | 75 | | | | | 80 | | |

| GAT | GCC | GTC | GCT | CTG | AAA | GAG | CGC | AAC | AAT | GCC | GTT | GAT | TGG | ATT | CGT | 764 |
|---|---|---|---|---|---|---|---|---|---|---|---|---|---|---|---|---|
| Asp | Ala | Val | Ala | Leu | Lys | Glu | Arg | Asn | Asn | Ala | Val | Asp | Trp | Ile | Arg | |
| | | | 85 | | | | | 90 | | | | | 95 | | | |

| ACC | ACC | CGC | ATC | GCG | CTG | GCA | GGC | TAC | TCC | TAC | ATC | GAC | GTC | ATA | TGC | 812 |
|---|---|---|---|---|---|---|---|---|---|---|---|---|---|---|---|---|
| Thr | Thr | Arg | Ile | Ala | Leu | Ala | Gly | Tyr | Ser | Tyr | Ile | Asp | Val | Ile | Cys | |
| | | 100 | | | | | 105 | | | | | 110 | | | | |

| AGA | AGC | TAC | ACA | GGC | TGT | CCC | AAA | CTT | GTC | TAT | AAA | ACC | CGA | TTT | ACC | 860 |
|---|---|---|---|---|---|---|---|---|---|---|---|---|---|---|---|---|
| Arg | Ser | Tyr | Thr | Gly | Cys | Pro | Lys | Leu | Val | Tyr | Lys | Thr | Arg | Phe | Thr | |
| | 115 | | | | | 120 | | | | | 125 | | | | | |

| TTC | GGT | CAA | CAA | GGG | TTG | AAA | AGA | AAG | GCA | GGC | AGC | AAG | CTG | GAT | ATA | 908 |
|---|---|---|---|---|---|---|---|---|---|---|---|---|---|---|---|---|
| Phe | Gly | Gln | Gln | Gly | Leu | Lys | Arg | Lys | Ala | Gly | Ser | Lys | Leu | Asp | Ile | |
| 130 | | | | | 135 | | | | | 140 | | | | | 145 | |

| TAC | GAA | GAC | AAA | AGC | CGC | GAA | AAT | TCG | CCC | ATT | TAC | AAA | TTG | TCG | GAT | 956 |
|---|---|---|---|---|---|---|---|---|---|---|---|---|---|---|---|---|
| Tyr | Glu | Asp | Lys | Ser | Arg | Glu | Asn | Ser | Pro | Ile | Tyr | Lys | Leu | Ser | Asp | |
| | | | | 150 | | | | | 155 | | | | | 160 | | |

| TAT | CCT | TGG | TTG | GGC | GTA | TCT | TTC | AAT | TTG | GGC | AGC | GAG | AAT | ACC | GTC | 1004 |
|---|---|---|---|---|---|---|---|---|---|---|---|---|---|---|---|---|
| Tyr | Pro | Trp | Leu | Gly | Val | Ser | Phe | Asn | Leu | Gly | Ser | Glu | Asn | Thr | Val | |
| | | | 165 | | | | | 170 | | | | | 175 | | | |

| CAA | AAT | AGC | AAA | TTA | TTC | AAC | AAA | TTG | ATA | TCT | TCT | TTT | AGA | GAA | GGC | 1052 |
|---|---|---|---|---|---|---|---|---|---|---|---|---|---|---|---|---|
| Gln | Asn | Ser | Lys | Leu | Phe | Asn | Lys | Leu | Ile | Ser | Ser | Phe | Arg | Glu | Gly | |
| | | 180 | | | | | 185 | | | | | 190 | | | | |

| AAT | AAT | AAT | CAA | ACC | ATC | GTC | TCT | ACG | ACA | GAA | GGC | AAC | CCT | ATT | TCC | 1100 |
|---|---|---|---|---|---|---|---|---|---|---|---|---|---|---|---|---|
| Asn | Asn | Asn | Gln | Thr | Ile | Val | Ser | Thr | Thr | Glu | Gly | Asn | Pro | Ile | Ser | |
| 195 | | | | | 200 | | | | | 205 | | | | | | |

| CTT | GGC | GAC | CGG | CAG | CGC | GAA | CAT | ACC | GCC | GTG | GCC | TAT | TAT | CTG | AAC | 1148 |
|---|---|---|---|---|---|---|---|---|---|---|---|---|---|---|---|---|
| Leu | Gly | Asp | Arg | Gln | Arg | Glu | His | Thr | Ala | Val | Ala | Tyr | Tyr | Leu | Asn | |
| 210 | | | | | 215 | | | | | 220 | | | | | 225 | |

| GCC | AAA | CTG | CAC | CTG | CTG | GAC | AAA | AAA | GGG | ATT | GAA | GAT | ATC | GCC | CAA | 1196 |
|---|---|---|---|---|---|---|---|---|---|---|---|---|---|---|---|---|
| Ala | Lys | Leu | His | Leu | Leu | Asp | Lys | Lys | Gly | Ile | Glu | Asp | Ile | Ala | Gln | |
| | | | | 230 | | | | | 235 | | | | | 240 | | |

| GGC | AAA | ATA | GTG | GAT | TTG | GGT | ATC | TTG | AAA | CCG | CAC | GTC | GAG | ACG | ACA | 1244 |
|---|---|---|---|---|---|---|---|---|---|---|---|---|---|---|---|---|
| Gly | Lys | Ile | Val | Asp | Leu | Gly | Ile | Leu | Lys | Pro | His | Val | Glu | Thr | Thr | |
| | | | 245 | | | | | 250 | | | | | 255 | | | |

| GGA | CGA | AGC | TTG | CTA | GAT | TTT | TGG | GCT | AGG | TGG | GAC | ATT | AAA | GAT | ACC | 1292 |
|---|---|---|---|---|---|---|---|---|---|---|---|---|---|---|---|---|
| Gly | Arg | Ser | Leu | Leu | Asp | Phe | Trp | Ala | Arg | Trp | Asp | Ile | Lys | Asp | Thr | |
| | | 260 | | | | | 265 | | | | | 270 | | | | |

| GGG | CAG | ATT | CCG | GTC | AAG | CTC | GGC | CTG | CCG | CAA | GTC | AAA | GCA | GGC | CGC | 1340 |
|---|---|---|---|---|---|---|---|---|---|---|---|---|---|---|---|---|
| Gly | Gln | Ile | Pro | Val | Lys | Leu | Gly | Leu | Pro | Gln | Val | Lys | Ala | Gly | Arg | |
| | 275 | | | | | 280 | | | | | 285 | | | | | |

| TGC | ACC | AAC | AAA | CCG | AAC | CCC | AAT | AAT | AAT | ACC | AAA | GCC | CCT | TCG | CCG | 1388 |
|---|---|---|---|---|---|---|---|---|---|---|---|---|---|---|---|---|
| Cys | Thr | Asn | Lys | Pro | Asn | Pro | Asn | Asn | Asn | Thr | Lys | Ala | Pro | Ser | Pro | |
| 290 | | | | | 295 | | | | | 300 | | | | | 305 | |

| GCA | CTG | ACC | GCC | CCC | GCG | CTG | TGG | TTC | GGA | CCC | GGG | CAA | GAT | GGT | AAG | 1436 |
|---|---|---|---|---|---|---|---|---|---|---|---|---|---|---|---|---|
| Ala | Leu | Thr | Ala | Pro | Ala | Leu | Trp | Phe | Gly | Pro | Gly | Gln | Asp | Gly | Lys | |
| | | | | 310 | | | | | 315 | | | | | 320 | | |

| GCG | GAG | ATG | TAT | TCC | GCT | TCG | GTT | TCC | ACC | TAC | CCC | GAC | AGT | TCG | AGC | 1484 |
|---|---|---|---|---|---|---|---|---|---|---|---|---|---|---|---|---|

-continued

| | | | | | | | | | | | | | | | |
|---|---|---|---|---|---|---|---|---|---|---|---|---|---|---|---|
| Ala | Glu | Met | Tyr<br>325 | Ser | Ala | Ser | Val | Ser<br>330 | Thr | Tyr | Pro | Asp | Ser<br>335 | Ser | Ser |

| AGC | CGC | ATC | TTC | CTC | CAA | GAG | CTG | AAA | ACT | CAA | ACC | GAA | CCC | GGC | AAA | 1532 |
|---|---|---|---|---|---|---|---|---|---|---|---|---|---|---|---|---|
| Ser | Arg<br>340 | Ile | Phe | Leu | Gln | Glu | Leu<br>345 | Lys | Thr | Gln | Thr | Glu<br>350 | Pro | Gly | Lys | |

| CCC | GGC | CGC | TAT | TCC | CTC | AAA | TCT | TTG | AAT | GAT | GGT | GAG | ATT | AAA | AGT | 1580 |
|---|---|---|---|---|---|---|---|---|---|---|---|---|---|---|---|---|
| Pro | Gly<br>355 | Arg | Tyr | Ser | Leu | Lys<br>360 | Ser | Leu | Asn | Asp | Gly<br>365 | Glu | Ile | Lys | Ser | |

| CGA | CAG | CCG | AGT | TTC | AAC | GGG | CGG | CAA | ACA | ATC | ATC | CGA | TTG | GAT | GAC | 1628 |
|---|---|---|---|---|---|---|---|---|---|---|---|---|---|---|---|---|
| Arg<br>370 | Gln | Pro | Ser | Phe | Asn<br>375 | Gly | Arg | Gln | Thr | Ile<br>380 | Ile | Arg | Leu | Asp | Asp<br>385 | |

| GGC | GTA | CAT | TTG | ATC | AAA | CTG | AAT | GGA | AGC | AAG | GAT | GAG | GTC | GCC | GCT | 1676 |
|---|---|---|---|---|---|---|---|---|---|---|---|---|---|---|---|---|
| Gly | Val | His | Leu | Ile<br>390 | Lys | Leu | Asn | Gly | Ser<br>395 | Lys | Asp | Glu | Val | Ala<br>400 | Ala | |

| TTT | GTC | AAT | TTA | AAT | GGA | AAC | AAC | ACC | GGC | AAA | AAC | GAC | ACT | TTC | GGC | 1724 |
|---|---|---|---|---|---|---|---|---|---|---|---|---|---|---|---|---|
| Phe | Val | Asn | Leu<br>405 | Asn | Gly | Asn | Asn | Thr<br>410 | Gly | Lys | Asn | Asp | Thr<br>415 | Phe | Gly | |

| ATT | GTT | AAG | GAA | GCG | AAC | GTC | AAT | CTT | GAC | GCC | GAC | GAG | TGG | AAA | AAA | 1772 |
|---|---|---|---|---|---|---|---|---|---|---|---|---|---|---|---|---|
| Ile | Val | Lys<br>420 | Glu | Ala | Asn | Val | Asn<br>425 | Leu | Asp | Ala | Asp | Glu<br>430 | Trp | Lys | Lys | |

| GTG | CTG | CTG | CCT | TGG | ACG | GTT | CGG | GGT | CCC | GAT | AAT | GAC | AAT | AAA | TTT | 1820 |
|---|---|---|---|---|---|---|---|---|---|---|---|---|---|---|---|---|
| Val | Leu<br>435 | Leu | Pro | Trp | Thr | Val<br>440 | Arg | Gly | Pro | Asp | Asn<br>445 | Asp | Asn | Lys | Phe | |

| AAA | TCA | ATT | AAC | CAA | AAA | CCA | GAA | AAA | TAC | AGC | CAA | AGA | TAC | CGC | ATC | 1868 |
|---|---|---|---|---|---|---|---|---|---|---|---|---|---|---|---|---|
| Lys<br>450 | Ser | Ile | Asn | Gln | Lys<br>455 | Pro | Glu | Lys | Tyr | Ser<br>460 | Gln | Arg | Tyr | Arg | Ile<br>465 | |

| CGC | GAC | AAC | AAC | GGC | AAT | CGC | GAT | TTG | GGC | GAC | ATC | GTC | AAC | AGC | CCG | 1916 |
|---|---|---|---|---|---|---|---|---|---|---|---|---|---|---|---|---|
| Arg | Asp | Asn | Asn | Gly<br>470 | Asn | Arg | Asp | Leu | Gly<br>475 | Asp | Ile | Val | Asn | Ser<br>480 | Pro | |

| ATT | GTC | GCG | GTC | GGC | GGG | TAT | TTG | GCA | ACC | GCC | GCG | AAC | GAC | GGG | ATG | 1964 |
|---|---|---|---|---|---|---|---|---|---|---|---|---|---|---|---|---|
| Ile | Val | Ala | Val<br>485 | Gly | Gly | Tyr | Leu | Ala<br>490 | Thr | Ala | Ala | Asn | Asp<br>495 | Gly | Met | |

| GTG | CAT | ATC | TTC | AAA | AAA | AAC | GGC | GGC | AGT | GAT | GAA | CGC | AGC | TAC | AAT | 2012 |
|---|---|---|---|---|---|---|---|---|---|---|---|---|---|---|---|---|
| Val | His | Ile<br>500 | Phe | Lys | Lys | Asn | Gly<br>505 | Gly | Ser | Asp | Glu | Arg<br>510 | Ser | Tyr | Asn | |

| CTG | AAG | CTC | AGC | TAC | ATC | CCC | GGC | ACG | ATG | CCG | CGC | AAG | GAT | ATT | CAA | 2060 |
|---|---|---|---|---|---|---|---|---|---|---|---|---|---|---|---|---|
| Leu | Lys<br>515 | Leu | Ser | Tyr | Ile | Pro<br>520 | Gly | Thr | Met | Pro | Arg<br>525 | Lys | Asp | Ile | Gln | |

| AGC | CAA | GAA | TCC | ACC | CTT | GCC | AAA | GAG | CTG | CGC | GCC | TTT | GCC | GAA | AAA | 2108 |
|---|---|---|---|---|---|---|---|---|---|---|---|---|---|---|---|---|
| Ser<br>530 | Gln | Glu | Ser | Thr | Leu<br>535 | Ala | Lys | Glu | Leu | Arg<br>540 | Ala | Phe | Ala | Glu | Lys<br>545 | |

| GGC | TAT | GTG | GGC | GAC | CGC | TAC | GGC | GTG | GAC | GGC | GGC | TTT | GTC | TTG | CGC | 2156 |
|---|---|---|---|---|---|---|---|---|---|---|---|---|---|---|---|---|
| Gly | Tyr | Val | Gly | Asp<br>550 | Arg | Tyr | Gly | Val | Asp<br>555 | Gly | Gly | Phe | Val | Leu<br>560 | Arg | |

| CAA | GTC | GAA | CTG | AGC | GGG | CAA | AAA | CAC | GTG | TTT | ATG | TTC | GGC | GCG | ATG | 2204 |
|---|---|---|---|---|---|---|---|---|---|---|---|---|---|---|---|---|
| Gln | Val | Glu | Leu | Ser<br>565 | Gly | Gln | Lys | His | Val<br>570 | Phe | Met | Phe | Gly | Ala<br>575 | Met | |

| GGT | TTT | GGC | GGC | AGG | GGC | GCG | TAT | GCC | TTG | GAT | TTA | AGC | AAA | ATC | AAC | 2252 |
|---|---|---|---|---|---|---|---|---|---|---|---|---|---|---|---|---|
| Gly | Phe | Gly<br>580 | Gly | Arg | Gly | Ala | Tyr<br>585 | Ala | Leu | Asp | Leu | Ser<br>590 | Lys | Ile | Asn | |

| GGA | AAT | TAT | CCG | GCC | GCC | GCC | CCC | CTG | TTT | GAT | GTC | AAA | GAT | GGC | GAT | 2300 |
|---|---|---|---|---|---|---|---|---|---|---|---|---|---|---|---|---|
| Gly | Asn<br>595 | Tyr | Pro | Ala | Ala | Ala<br>600 | Pro | Leu | Phe | Asp | Val<br>605 | Lys | Asp | Gly | Asp | |

| AAT | AAC | GGC | AAA | AAT | CGC | GTG | AAA | GTG | GAA | TTA | GGC | TAC | ACC | GTC | GGT | 2348 |
|---|---|---|---|---|---|---|---|---|---|---|---|---|---|---|---|---|
| Asn<br>610 | Asn | Gly | Lys | Asn | Arg<br>615 | Val | Lys | Val | Glu | Leu<br>620 | Gly | Tyr | Thr | Val | Gly<br>625 | |

| ACG | CCG | CAA | ATC | GGC | AAA | ATC | CGC | AAC | GGA | AAA | TAC | GCC | GCC | TTC | CTC | 2396 |
|---|---|---|---|---|---|---|---|---|---|---|---|---|---|---|---|---|
| Thr | Pro | Gln | Ile<br>630 | Gly | Lys | Ile | Arg | Asn<br>635 | Gly | Lys | Tyr | Ala | Ala<br>640 | Phe | Leu | |

| GCC | TCC | GGT | TAT | GCG | GCT | AAA | AAA | ATT | GAC | GAC | TCA | ACA | AAT | AAA | ACC | 2444 |
|---|---|---|---|---|---|---|---|---|---|---|---|---|---|---|---|---|

-continued

| | | | | | | | | | | | | | | | |
|---|---|---|---|---|---|---|---|---|---|---|---|---|---|---|---|
| Ala | Ser | Gly | Tyr | Ala | Ala | Lys | Lys | Ile | Asp | Asp | Ser | Thr | Asn | Lys | Thr |
| | | | 645 | | | | 650 | | | | | 655 | | | |

| GCG | CTG | TAT | GTA | TAT | GAT | TTG | AAA | GAC | ACC | TTA | GGT | ACG | CCG | ATT | GCA | 2492 |
|---|---|---|---|---|---|---|---|---|---|---|---|---|---|---|---|---|
| Ala | Leu | Tyr | Val | Tyr | Asp | Leu | Lys | Asp | Thr | Leu | Gly | Thr | Pro | Ile | Ala | |
| | | 660 | | | | | 665 | | | | | 670 | | | | |

| AAA | ATC | GAA | GTG | AAG | GAC | GGC | AAA | GGC | GGG | CTT | TCG | TCC | CCC | ACG | CTG | 2540 |
|---|---|---|---|---|---|---|---|---|---|---|---|---|---|---|---|---|
| Lys | Ile | Glu | Val | Lys | Asp | Gly | Lys | Gly | Gly | Leu | Ser | Ser | Pro | Thr | Leu | |
| | 675 | | | | | 680 | | | | | 685 | | | | | |

| GTG | GAT | AAA | GAT | TTG | GAC | GGC | ACG | GTC | GAT | ATC | GCC | TAT | GCC | GGC | GAC | 2588 |
|---|---|---|---|---|---|---|---|---|---|---|---|---|---|---|---|---|
| Val | Asp | Lys | Asp | Leu | Asp | Gly | Thr | Val | Asp | Ile | Ala | Tyr | Ala | Gly | Asp | |
| 690 | | | | | 695 | | | | | 700 | | | | | 705 | |

| CGG | GGC | GGC | AAT | ATG | TAC | CGC | TTT | GAT | TTG | AGC | AAT | TCC | GAT | TCT | AGT | 2636 |
|---|---|---|---|---|---|---|---|---|---|---|---|---|---|---|---|---|
| Arg | Gly | Gly | Asn | Met | Tyr | Arg | Phe | Asp | Leu | Ser | Asn | Ser | Asp | Ser | Ser | |
| | | | | 710 | | | | | 715 | | | | | 720 | | |

| AAA | TGG | TCT | GCA | AAG | GTT | ATT | TTC | GAA | GGC | GAC | AAG | CCG | ATT | ACC | TCC | 2684 |
|---|---|---|---|---|---|---|---|---|---|---|---|---|---|---|---|---|
| Lys | Trp | Ser | Ala | Lys | Val | Ile | Phe | Glu | Gly | Asp | Lys | Pro | Ile | Thr | Ser | |
| | | | 725 | | | | | 730 | | | | | 735 | | | |

| GCG | CCC | GCC | GTT | TCC | CGA | CTG | GCA | GAC | AAA | CGC | GTC | GTC | ATC | TTC | GGT | 2732 |
|---|---|---|---|---|---|---|---|---|---|---|---|---|---|---|---|---|
| Ala | Pro | Ala | Val | Ser | Arg | Leu | Ala | Asp | Lys | Arg | Val | Val | Ile | Phe | Gly | |
| | | 740 | | | | | 745 | | | | | 750 | | | | |

| ACG | GGC | AGC | GAT | TTG | ACC | GAA | GAT | GAT | GTA | CTG | AAT | ACG | GGC | GAA | CAA | 2780 |
|---|---|---|---|---|---|---|---|---|---|---|---|---|---|---|---|---|
| Thr | Gly | Ser | Asp | Leu | Thr | Glu | Asp | Asp | Val | Leu | Asn | Thr | Gly | Glu | Gln | |
| | 755 | | | | | 760 | | | | | 765 | | | | | |

| TAT | ATT | TAC | GGT | ATC | TTT | GAC | GAC | GAT | AAG | GGG | ACG | GTT | AAG | GTA | ACG | 2828 |
|---|---|---|---|---|---|---|---|---|---|---|---|---|---|---|---|---|
| Tyr | Ile | Tyr | Gly | Ile | Phe | Asp | Asp | Asp | Lys | Gly | Thr | Val | Lys | Val | Thr | |
| 770 | | | | | 775 | | | | | 780 | | | | | 785 | |

| GTA | CAA | AAC | GGC | ACG | GCA | GGC | GGG | CTG | CTC | GAG | CAA | CAC | CTT | ACT | CAG | 2876 |
|---|---|---|---|---|---|---|---|---|---|---|---|---|---|---|---|---|
| Val | Gln | Asn | Gly | Thr | Ala | Gly | Gly | Leu | Leu | Glu | Gln | His | Leu | Thr | Gln | |
| | | | | 790 | | | | | 795 | | | | | 800 | | |

| GAA | AAT | AAA | ACA | TTA | TTC | CTG | AAC | AAG | AGA | TCC | GAC | GGT | TCG | GGC | AGC | 2924 |
|---|---|---|---|---|---|---|---|---|---|---|---|---|---|---|---|---|
| Glu | Asn | Lys | Thr | Leu | Phe | Leu | Asn | Lys | Arg | Ser | Asp | Gly | Ser | Gly | Ser | |
| | | | 805 | | | | | 810 | | | | | 815 | | | |

| AAG | GGC | TGG | GCG | GTG | AAA | TTG | AGG | GAA | GGA | GAA | CGC | GTT | ACC | GTC | AAA | 2972 |
|---|---|---|---|---|---|---|---|---|---|---|---|---|---|---|---|---|
| Lys | Gly | Trp | Ala | Val | Lys | Leu | Arg | Glu | Gly | Glu | Arg | Val | Thr | Val | Lys | |
| | | 820 | | | | | 825 | | | | | 830 | | | | |

| CCG | ACC | GTG | GTA | TTG | CGT | ACC | GCC | TTC | GTA | ACC | ATC | CGC | AAA | TAT | AAC | 3020 |
|---|---|---|---|---|---|---|---|---|---|---|---|---|---|---|---|---|
| Pro | Thr | Val | Val | Leu | Arg | Thr | Ala | Phe | Val | Thr | Ile | Arg | Lys | Tyr | Asn | |
| | 835 | | | | | 840 | | | | | 845 | | | | | |

| GAC | GGC | GGC | TGC | GGC | GCG | GAA | ACC | GCC | ATT | TTG | GGC | ATC | AAT | ACC | GCC | 3068 |
|---|---|---|---|---|---|---|---|---|---|---|---|---|---|---|---|---|
| Asp | Gly | Gly | Cys | Gly | Ala | Glu | Thr | Ala | Ile | Leu | Gly | Ile | Asn | Thr | Ala | |
| 850 | | | | | 855 | | | | | 860 | | | | | 865 | |

| GAC | GGC | GGC | GCA | TTG | ACT | CCG | AGA | AGC | GCG | CGC | CCG | ATT | GTG | CCG | GAT | 3116 |
|---|---|---|---|---|---|---|---|---|---|---|---|---|---|---|---|---|
| Asp | Gly | Gly | Ala | Leu | Thr | Pro | Arg | Ser | Ala | Arg | Pro | Ile | Val | Pro | Asp | |
| | | | | 870 | | | | | 875 | | | | | 880 | | |

| CAC | AAT | TCG | GTT | GCG | CAA | TAT | TCC | GGC | CAT | AAG | ACA | ACC | TCC | AAA | GGC | 3164 |
|---|---|---|---|---|---|---|---|---|---|---|---|---|---|---|---|---|
| His | Asn | Ser | Val | Ala | Gln | Tyr | Ser | Gly | His | Lys | Thr | Thr | Ser | Lys | Gly | |
| | | | 885 | | | | | 890 | | | | | 895 | | | |

| AAA | TCC | ATC | CCT | ATA | GGT | TGT | ATG | GAC | AAA | GAC | GGT | AAA | ACC | GTC | TGC | 3212 |
|---|---|---|---|---|---|---|---|---|---|---|---|---|---|---|---|---|
| Lys | Ser | Ile | Pro | Ile | Gly | Cys | Met | Asp | Lys | Asp | Gly | Lys | Thr | Val | Cys | |
| | | 900 | | | | | 905 | | | | | 910 | | | | |

| CCG | AAC | GGA | TAT | GTT | TAC | GAC | AAG | CCG | GTT | AAT | GTG | CGT | TAT | CTG | GAT | 3260 |
|---|---|---|---|---|---|---|---|---|---|---|---|---|---|---|---|---|
| Pro | Asn | Gly | Tyr | Val | Tyr | Asp | Lys | Pro | Val | Asn | Val | Arg | Tyr | Leu | Asp | |
| | 915 | | | | | 920 | | | | | 925 | | | | | |

| GAA | ACG | GAA | ACA | GAC | GGA | TTT | TCA | ACG | ACG | GCG | GAC | GGC | GAT | GCG | GGC | 3308 |
|---|---|---|---|---|---|---|---|---|---|---|---|---|---|---|---|---|
| Glu | Thr | Glu | Thr | Asp | Gly | Phe | Ser | Thr | Thr | Ala | Asp | Gly | Asp | Ala | Gly | |
| 930 | | | | | 935 | | | | | 940 | | | | | 945 | |

| GGC | AGC | GGT | ATA | GAC | CCC | GCC | GGC | AGG | CGT | CCC | GGC | AAA | AAC | AAC | CGC | 3356 |
|---|---|---|---|---|---|---|---|---|---|---|---|---|---|---|---|---|
| Gly | Ser | Gly | Ile | Asp | Pro | Ala | Gly | Arg | Arg | Pro | Gly | Lys | Asn | Asn | Arg | |
| | | | | 950 | | | | | 955 | | | | | 960 | | |

| TGC | TTC | TCC | AAA | AAA | GGG | GTG | CGC | ACC | CTG | CTG | ATG | AAC | GAT | TTG | GAC | 3404 |

```
Cys  Phe  Ser  Lys  Lys  Gly  Val  Arg  Thr  Leu  Leu  Met  Asn  Asp  Leu  Asp
               965                      970                      975

AGC  TTG  GAT  ATT  ACC  GGC  CCG  ATG  TGC  GGT  ATC  AAA  CGC  TTA  AGC  TGG        3452
Ser  Leu  Asp  Ile  Thr  Gly  Pro  Met  Cys  Gly  Ile  Lys  Arg  Leu  Ser  Trp
               980                      985                      990

CGC  GAA  GTC  TTC  TTC  TGACCGGCCT  GCGCGGCCGG  TTTTTCCGCA  AATGCCGTCC             3507
Arg  Glu  Val  Phe  Phe
     995

GAAAGGCCTT  CGGACGGCAT  TTTTTTGCGT  TTTTCGGGAG  GGGGGCGGCA  AATGAAACG                3566
```

( 2 ) INFORMATION FOR SEQ ID NO:7:

( i ) SEQUENCE CHARACTERISTICS:
        ( A ) LENGTH: 998 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met  Ala  Gln  Thr  His  Gln  Tyr  Ala  Ile  Ile  Met  Asn  Glu  Arg  Asn  Gln
 1                  5                      10                      15

Pro  Glu  Val  Lys  Gln  Asn  Val  Pro  Ser  Ile  Lys  Asp  Lys  Asp  Arg
               20                       25                      30

Arg  Arg  Glu  Tyr  Thr  Tyr  Tyr  Thr  His  Arg  Thr  Gly  Ala  Gly  Ser  Val
               35                       40                      45

Ser  Phe  Asn  Asn  Asn  Asp  Thr  Leu  Val  Ser  Gln  Gln  Ser  Gly  Thr  Ala
      50                       55                       60

Val  Phe  Gly  Thr  Ala  Thr  Tyr  Leu  Pro  Pro  Tyr  Gly  Lys  Val  Ser  Gly
 65                       70                      75                       80

Phe  Asp  Ala  Val  Ala  Leu  Lys  Glu  Arg  Asn  Asn  Ala  Val  Asp  Trp  Ile
                    85                       90                      95

Arg  Thr  Thr  Arg  Ile  Ala  Leu  Ala  Gly  Tyr  Ser  Tyr  Ile  Asp  Val  Ile
                100                     105                     110

Cys  Arg  Ser  Tyr  Thr  Gly  Cys  Pro  Lys  Leu  Val  Tyr  Lys  Thr  Arg  Phe
           115                     120                     125

Thr  Phe  Gly  Gln  Gln  Gly  Leu  Lys  Arg  Lys  Ala  Gly  Ser  Lys  Leu  Asp
     130                     135                     140

Ile  Tyr  Glu  Asp  Lys  Ser  Arg  Glu  Asn  Ser  Pro  Ile  Tyr  Lys  Leu  Ser
145                     150                     155                     160

Asp  Tyr  Pro  Trp  Leu  Gly  Val  Ser  Phe  Asn  Leu  Gly  Ser  Glu  Asn  Thr
               165                     170                     175

Val  Gln  Asn  Ser  Lys  Leu  Phe  Asn  Lys  Leu  Ile  Ser  Ser  Phe  Arg  Glu
               180                     185                     190

Gly  Asn  Asn  Asn  Gln  Thr  Ile  Val  Ser  Thr  Thr  Glu  Gly  Asn  Pro  Ile
          195                     200                     205

Ser  Leu  Gly  Asp  Arg  Gln  Arg  Glu  His  Thr  Ala  Val  Ala  Tyr  Tyr  Leu
     210                     215                     220

Asn  Ala  Lys  Leu  His  Leu  Leu  Asp  Lys  Lys  Gly  Ile  Glu  Asp  Ile  Ala
225                     230                     235                     240

Gln  Gly  Lys  Ile  Val  Asp  Leu  Gly  Ile  Leu  Lys  Pro  His  Val  Glu  Thr
               245                     250                     255

Thr  Gly  Arg  Ser  Leu  Leu  Asp  Phe  Trp  Ala  Arg  Trp  Asp  Ile  Lys  Asp
           260                     265                     270

Thr  Gly  Gln  Ile  Pro  Val  Lys  Leu  Gly  Leu  Pro  Gln  Val  Lys  Ala  Gly
           275                     280                     285

Arg  Cys  Thr  Asn  Lys  Pro  Asn  Pro  Asn  Asn  Asn  Thr  Lys  Ala  Pro  Ser
```

-continued

|     | 290 |     |     |     | 295 |     |     |     | 300 |     |     |     |     |
|-----|-----|-----|-----|-----|-----|-----|-----|-----|-----|-----|-----|-----|-----|
| Pro | Ala | Leu | Thr | Ala | Pro | Ala | Leu | Trp | Phe | Gly | Pro | Gly | Gln | Asp | Gly |
| 305 |     |     |     |     | 310 |     |     |     | 315 |     |     |     |     | 320 |
| Lys | Ala | Glu | Met | Tyr | Ser | Ala | Ser | Val | Ser | Thr | Tyr | Pro | Asp | Ser | Ser |
|     |     |     |     | 325 |     |     |     |     | 330 |     |     |     |     | 335 |
| Ser | Ser | Arg | Ile | Phe | Leu | Gln | Glu | Leu | Lys | Thr | Gln | Thr | Glu | Pro | Gly |
|     |     |     |     | 340 |     |     |     |     | 345 |     |     |     |     | 350 |
| Lys | Pro | Gly | Arg | Tyr | Ser | Leu | Lys | Ser | Leu | Asn | Asp | Gly | Glu | Ile | Lys |
|     |     |     |     | 355 |     |     |     |     | 360 |     |     |     |     | 365 |
| Ser | Arg | Gln | Pro | Ser | Phe | Asn | Gly | Arg | Gln | Thr | Ile | Ile | Arg | Leu | Asp |
|     | 370 |     |     |     |     | 375 |     |     |     |     | 380 |     |     |     |     |
| Asp | Gly | Val | His | Leu | Ile | Lys | Leu | Asn | Gly | Ser | Lys | Asp | Glu | Val | Ala |
| 385 |     |     |     |     | 390 |     |     |     |     | 395 |     |     |     |     | 400 |
| Ala | Phe | Val | Asn | Leu | Asn | Gly | Asn | Asn | Thr | Gly | Lys | Asn | Asp | Thr | Phe |
|     |     |     |     | 405 |     |     |     |     | 410 |     |     |     |     | 415 |     |
| Gly | Ile | Val | Lys | Glu | Ala | Asn | Val | Asn | Leu | Asp | Ala | Asp | Glu | Trp | Lys |
|     |     |     | 420 |     |     |     |     | 425 |     |     |     |     | 430 |     |     |
| Lys | Val | Leu | Leu | Pro | Trp | Thr | Val | Arg | Gly | Pro | Asp | Asn | Asp | Asn | Lys |
|     |     | 435 |     |     |     |     | 440 |     |     |     |     | 445 |     |     |     |
| Phe | Lys | Ser | Ile | Asn | Gln | Lys | Pro | Glu | Lys | Tyr | Ser | Gln | Arg | Tyr | Arg |
|     | 450 |     |     |     |     | 455 |     |     |     |     | 460 |     |     |     |     |
| Ile | Arg | Asp | Asn | Asn | Gly | Asn | Arg | Asp | Leu | Gly | Asp | Ile | Val | Asn | Ser |
| 465 |     |     |     |     | 470 |     |     |     |     | 475 |     |     |     |     | 480 |
| Pro | Ile | Val | Ala | Val | Gly | Gly | Tyr | Leu | Ala | Thr | Ala | Ala | Asn | Asp | Gly |
|     |     |     |     | 485 |     |     |     |     | 490 |     |     |     |     | 495 |     |
| Met | Val | His | Ile | Phe | Lys | Lys | Asn | Gly | Gly | Ser | Asp | Glu | Arg | Ser | Tyr |
|     |     |     | 500 |     |     |     |     | 505 |     |     |     |     | 510 |     |     |
| Asn | Leu | Lys | Leu | Ser | Tyr | Ile | Pro | Gly | Thr | Met | Pro | Arg | Lys | Asp | Ile |
|     |     | 515 |     |     |     |     | 520 |     |     |     |     | 525 |     |     |     |
| Gln | Ser | Gln | Glu | Ser | Thr | Leu | Ala | Lys | Glu | Leu | Arg | Ala | Phe | Ala | Glu |
|     | 530 |     |     |     |     | 535 |     |     |     |     | 540 |     |     |     |     |
| Lys | Gly | Tyr | Val | Gly | Asp | Arg | Tyr | Gly | Val | Asp | Gly | Gly | Phe | Val | Leu |
| 545 |     |     |     |     | 550 |     |     |     |     | 555 |     |     |     |     | 560 |
| Arg | Gln | Val | Glu | Leu | Ser | Gly | Gln | Lys | His | Val | Phe | Met | Phe | Gly | Ala |
|     |     |     |     | 565 |     |     |     |     | 570 |     |     |     |     | 575 |     |
| Met | Gly | Phe | Gly | Gly | Arg | Gly | Ala | Tyr | Ala | Leu | Asp | Leu | Ser | Lys | Ile |
|     |     |     | 580 |     |     |     |     | 585 |     |     |     |     | 590 |     |     |
| Asn | Gly | Asn | Tyr | Pro | Ala | Ala | Ala | Pro | Leu | Phe | Asp | Val | Lys | Asp | Gly |
|     |     | 595 |     |     |     |     | 600 |     |     |     |     | 605 |     |     |     |
| Asp | Asn | Asn | Gly | Lys | Asn | Arg | Val | Lys | Val | Glu | Leu | Gly | Tyr | Thr | Val |
|     | 610 |     |     |     |     | 615 |     |     |     |     | 620 |     |     |     |     |
| Gly | Thr | Pro | Gln | Ile | Gly | Lys | Ile | Arg | Asn | Gly | Lys | Tyr | Ala | Ala | Phe |
| 625 |     |     |     |     | 630 |     |     |     |     | 635 |     |     |     |     | 640 |
| Leu | Ala | Ser | Gly | Tyr | Ala | Ala | Lys | Lys | Ile | Asp | Asp | Ser | Thr | Asn | Lys |
|     |     |     |     | 645 |     |     |     |     | 650 |     |     |     |     | 655 |     |
| Thr | Ala | Leu | Tyr | Val | Tyr | Asp | Leu | Lys | Asp | Thr | Leu | Gly | Thr | Pro | Ile |
|     |     |     | 660 |     |     |     |     | 665 |     |     |     |     | 670 |     |     |
| Ala | Lys | Ile | Glu | Val | Lys | Asp | Gly | Lys | Gly | Leu | Ser | Ser | Pro | Thr |
|     |     | 675 |     |     |     |     | 680 |     |     |     |     | 685 |     |     |     |
| Leu | Val | Asp | Lys | Asp | Leu | Asp | Gly | Thr | Val | Asp | Ile | Ala | Tyr | Ala | Gly |
|     | 690 |     |     |     |     | 695 |     |     |     |     | 700 |     |     |     |     |
| Asp | Arg | Gly | Gly | Asn | Met | Tyr | Arg | Phe | Asp | Leu | Ser | Asn | Ser | Asp | Ser |
| 705 |     |     |     |     | 710 |     |     |     |     | 715 |     |     |     |     | 720 |

| | | | | | | | | | | | | | | |
|---|---|---|---|---|---|---|---|---|---|---|---|---|---|---|
| Ser | Lys | Trp | Ser | Ala<br>725 | Lys | Val | Ile | Phe | Glu<br>730 | Gly | Asp | Lys | Pro | Ile Thr<br>735 |
| Ser | Ala | Pro | Ala<br>740 | Val | Ser | Arg | Leu | Ala<br>745 | Asp | Lys | Arg | Val | Val<br>750 | Ile Phe |
| Gly | Thr | Gly<br>755 | Ser | Asp | Leu | Thr | Glu<br>760 | Asp | Asp | Val | Leu | Asn<br>765 | Thr | Gly Glu |
| Gln | Tyr<br>770 | Ile | Tyr | Gly | Ile | Phe<br>775 | Asp | Asp | Asp | Lys | Gly<br>780 | Thr | Val | Lys Val |
| Thr<br>785 | Val | Gln | Asn | Gly | Thr<br>790 | Ala | Gly | Gly | Leu | Leu<br>795 | Glu | Gln | His | Leu Thr<br>800 |
| Gln | Glu | Asn | Lys | Thr<br>805 | Leu | Phe | Leu | Asn | Lys<br>810 | Arg | Ser | Asp | Gly<br>815 | Ser Gly |
| Ser | Lys | Gly | Trp<br>820 | Ala | Val | Lys | Leu | Arg<br>825 | Glu | Gly | Glu | Arg | Val<br>830 | Thr Val |
| Lys | Pro | Thr<br>835 | Val | Val | Leu | Arg | Thr<br>840 | Ala | Phe | Val | Thr | Ile<br>845 | Arg | Lys Tyr |
| Asn | Asp<br>850 | Gly | Gly | Cys | Gly | Ala<br>855 | Glu | Thr | Ala | Ile | Leu<br>860 | Gly | Ile | Asn Thr |
| Ala<br>865 | Asp | Gly | Gly | Ala | Leu<br>870 | Thr | Pro | Arg | Ser | Ala<br>875 | Arg | Pro | Ile | Val Pro<br>880 |
| Asp | His | Asn | Ser | Val<br>885 | Ala | Gln | Tyr | Ser | Gly<br>890 | His | Lys | Thr | Thr | Ser Lys<br>895 |
| Gly | Lys | Ser | Ile<br>900 | Pro | Ile | Gly | Cys | Met<br>905 | Asp | Lys | Asp | Gly | Lys<br>910 | Thr Val |
| Cys | Pro | Asn<br>915 | Gly | Tyr | Val | Tyr | Asp<br>920 | Lys | Pro | Val | Asn | Val<br>925 | Arg | Tyr Leu |
| Asp | Glu<br>930 | Thr | Glu | Thr | Asp | Gly<br>935 | Phe | Ser | Thr | Thr | Ala<br>940 | Asp | Gly | Asp Ala |
| Gly<br>945 | Gly | Ser | Gly | Ile | Asp<br>950 | Pro | Ala | Gly | Arg | Arg<br>955 | Pro | Gly | Lys | Asn Asn<br>960 |
| Arg | Cys | Phe | Ser | Lys<br>965 | Lys | Gly | Val | Arg | Thr<br>970 | Leu | Leu | Met | Asn | Asp Leu<br>975 |
| Asp | Ser | Leu | Asp<br>980 | Ile | Thr | Gly | Pro | Met<br>985 | Cys | Gly | Ile | Lys | Arg<br>990 | Leu Ser |
| Trp | Arg | Glu | Val<br>995 | Phe | Phe | | | | | | | | | |

( 2 ) INFORMATION FOR SEQ ID NO:8:

( i ) SEQUENCE CHARACTERISTICS:
        ( A ) LENGTH: 101 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:8:

```
CATACCGCGC TTTATGCCGC CATCTTGATG TTTTCCCATA CCGGCGGGGG GGGGGGGCGA    60
TGGCGCAAAC CCATCAATAC GCTATTATCA TGAACGAGCG A                       101
```

( 2 ) INFORMATION FOR SEQ ID NO:9:

( i ) SEQUENCE CHARACTERISTICS:
        ( A ) LENGTH: 100 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:9:

CATACCGCGC TTTATGCCGC CATCTTGATG TTTTCCCATA CCGGCGGGGG GGGGGGCGAT 60

GGCGCAAACC CATCAATACG CTATTATCAT GAACGAGCGA 100

( 2 ) INFORMATION FOR SEQ ID NO:10:

( i ) SEQUENCE CHARACTERISTICS:
        ( A ) LENGTH: 102 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..102

( x i ) SEQUENCE DESCRIPTION: SEQ ID NO:10:

```
CAT  ACC  GCG  CTT  TAT  GCC  GCC  ATC  TTG  ATG  TTT  TCC  CAT  ACC  GGC  GGG      48
His  Thr  Ala  Leu  Tyr  Ala  Ala  Ile  Leu  Met  Phe  Ser  His  Thr  Gly  Gly
 1                    5                        10                       15

GGG  GGG  GGG  GCG  CAG  GCG  CAA  ACC  CGT  AAA  TAC  GCT  ATT  ATC  ATG  AAC      96
Gly  Gly  Gly  Ala  Gln  Ala  Gln  Thr  Arg  Lys  Tyr  Ala  Ile  Ile  Met  Asn
                20                       25                       30

GAG  CGA                                                                            102
Glu  Arg
```

( 2 ) INFORMATION FOR SEQ ID NO:11:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
His  Thr  Ala  Leu  Tyr  Ala  Ala  Ile  Leu  Met  Phe  Ser  His  Thr  Gly  Gly
 1                    5                        10                       15

Gly  Gly  Gly  Ala  Gln  Ala  Gln  Thr  Arg  Lys  Tyr  Ala  Ile  Ile  Met  Asn
                20                       25                       30

Glu  Arg
```

( 2 ) INFORMATION FOR SEQ ID NO:12:

( i ) SEQUENCE CHARACTERISTICS:
        ( A ) LENGTH: 101 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:12:

CATACCGCGC TTTATGCCGC CATCTTGATG TTTTCCCATA CCGGCGGGGG GGGGGGCGC 60

AGGCGCAAAC CCGTAAATAC GCTATTATCA TGAACGAGCG A 101

( 2 ) INFORMATION FOR SEQ ID NO:13:

( i ) SEQUENCE CHARACTERISTICS:
        ( A ) LENGTH: 102 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..102

( x i ) SEQUENCE DESCRIPTION: SEQ ID NO:13:

| CAT | ACC | GCG | CTT | TAT | GCC | GCC | ATC | TTG | ATG | TTT | TCC | CAT | ACC | GGC | GGG | 48 |
| His | Thr | Ala | Leu | Tyr | Ala | Ala | Ile | Leu | Met | Phe | Ser | His | Thr | Gly | Gly | |
| 1 | | | | 5 | | | | | 10 | | | | | 15 | | |

| GGG | GGG | GGG | GCG | ATG | GCG | CAA | ACC | CAT | CAA | TAC | GCT | ATT | ATC | ATG | AAC | 96 |
| Gly | Gly | Gly | Ala | Met | Ala | Gln | Thr | His | Gln | Tyr | Ala | Ile | Ile | Met | Asn | |
| | | | 20 | | | | | 25 | | | | | 30 | | | |

GAG CGA                                                                                                                                                                   102
Glu Arg ( 2 ) INFORMATION FOR SEQ ID NO:14:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

| His | Thr | Ala | Leu | Tyr | Ala | Ala | Ile | Leu | Met | Phe | Ser | His | Thr | Gly | Gly |
| 1 | | | | 5 | | | | | 10 | | | | | 15 | |

| Gly | Gly | Gly | Ala | Met | Ala | Gln | Thr | His | Gln | Tyr | Ala | Ile | Ile | Met | Asn |
| | | | 20 | | | | | 25 | | | | | 30 | | |

Glu Arg ( 2 ) INFORMATION FOR SEQ ID NO:15:

( i ) SEQUENCE CHARACTERISTICS:
        ( A ) LENGTH: 101 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:15:

CATACCGCGC TTTATGCCGC CATCTTGATG TTTTCCCATA CCGGCGGGGG GGGGGGGCGA       60

TGGCGCAAAC CCATCAATAC GCTATTATCA TGAACGAGCG A                          101

( 2 ) INFORMATION FOR SEQ ID NO:16:

( i ) SEQUENCE CHARACTERISTICS:
        ( A ) LENGTH: 100 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:16:

CATACCGCGC TTTATGCCGC CATCTTGATG TTTTCCCATA CCGGCGGGGG GGGGGGCGAT       60

GGCGCAAACC CATCAATACG CTATTATCAT GAACGAGCGA                            100

( 2 ) INFORMATION FOR SEQ ID NO:17:

( i ) SEQUENCE CHARACTERISTICS:
        ( A ) LENGTH: 102 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..102

( x i ) SEQUENCE DESCRIPTION: SEQ ID NO:17:

| CAT | ACC | GCG | CTT | TAT | GCC | GCC | ATC | TTG | ATG | TTT | TCC | CAT | ACC | GGC | GGG | 48 |
| His | Thr | Ala | Leu | Tyr | Ala | Ala | Ile | Leu | Met | Phe | Ser | His | Thr | Gly | Gly | |

```
              1                   5                    10                   15
GGG  GGG  GGG  GCG  ATG  GCG  CAA  ACG  TAT  AAA  TAC  GCT  ATT  GTG  ATG  AAC    96
Gly  Gly  Gly  Ala  Met  Ala  Gln  Thr  Tyr  Lys  Tyr  Ala  Ile  Val  Met  Asn
                         20                       25                   30

GAG  CGA                                                                         102
Glu  Arg
```

( 2 ) INFORMATION FOR SEQ ID NO:18:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
His  Thr  Ala  Leu  Tyr  Ala  Ala  Ile  Leu  Met  Phe  Ser  His  Thr  Gly  Gly
 1                    5                        10                       15

Gly  Gly  Gly  Ala  Met  Ala  Gln  Thr  Tyr  Lys  Tyr  Ala  Ile  Val  Met  Asn
                         20                       25                   30

Glu  Arg
```

( 2 ) INFORMATION FOR SEQ ID NO:19:

( i ) SEQUENCE CHARACTERISTICS:
        ( A ) LENGTH: 103 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:19:

```
CATACCGCGC  TTTATGCCGC  CATCTTGATG  TTTTCCCATA  CCGGCGGGGG  GGGGGGGGGC    60

GATGGCGCAA  ACGTATAAAT  ACGCTATTGT  GATGAACGAG  CGA                      103
```

( 2 ) INFORMATION FOR SEQ ID NO:20:

( i ) SEQUENCE CHARACTERISTICS:
        ( A ) LENGTH: 104 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:20:

```
CATACCGCGC  TTTATGCCGC  CATCTTGATG  TTTTCCCATA  CCGGCGGGGG  GGGGGCAGG     60

CGCAGGCGCA  AACGTATAAA  TACGCTATTG  TGATGAACGA  GCGA                     104
```

( 2 ) INFORMATION FOR SEQ ID NO:21:

( i ) SEQUENCE CHARACTERISTICS:
        ( A ) LENGTH: 101 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:21:

```
CATACCGCGC  TTTATGCCGC  CATCTTGATG  TTTTCCCATA  CCGGCGGGGG  GGGGGGGCGA    60

TGGCGCAAAC  CCATCAATAC  GCTATTATCA  TGAACGAGCG  A                        101
```

( 2 ) INFORMATION FOR SEQ ID NO:22:

( i ) SEQUENCE CHARACTERISTICS:
        ( A ) LENGTH: 100 base pairs
        ( B ) TYPE: nucleic acid

```
        ( C ) STRANDEDNESS: double
        ( D ) TOPOLOGY: linear ( x i ) SEQUENCE DESCRIPTION: SEQ ID NO:22:

CATACCGCGC  TTTATGCCGC  CATCTTGATG  TTTTCCCATA  CCGGCGGGGG  GGGGGGCGAT        60

GGCGCAAACC  CATCAATACG  CTATTATCAT  GAACGAGCGA                              100

( 2 ) INFORMATION FOR SEQ ID NO:23:

( i ) SEQUENCE CHARACTERISTICS:
        ( A ) LENGTH: 102 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..102

( x i ) SEQUENCE DESCRIPTION: SEQ ID NO:23:

CAT  ACC  GCG  CTT  TAT  GCC  GCC  ATC  TTG  ATG  TTT  TCC  CAT  ACC  GGC  GGG      48
His  Thr  Ala  Leu  Tyr  Ala  Ala  Ile  Leu  Met  Phe  Ser  His  Thr  Gly  Gly
 1                    5                         10                        15

GGG  GGG  GGG  GCG  ATG  GCG  CAA  ACC  CAT  CAA  TAC  GCT  ATT  ATC  ATG  AAC      96
Gly  Gly  Gly  Ala  Met  Ala  Gln  Thr  His  Gln  Tyr  Ala  Ile  Ile  Met  Asn
                20                        25                        30

GAG  CGA                                                                           102
Glu  Arg ( 2 ) INFORMATION FOR SEQ ID NO:24:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

His  Thr  Ala  Leu  Tyr  Ala  Ala  Ile  Leu  Met  Phe  Ser  His  Thr  Gly  Gly
 1                    5                         10                        15

Gly  Gly  Gly  Ala  Met  Ala  Gln  Thr  His  Gln  Tyr  Ala  Ile  Ile  Met  Asn
                20                        25                        30

Glu  Arg ( 2 ) INFORMATION FOR SEQ ID NO:25:

( i ) SEQUENCE CHARACTERISTICS:
        ( A ) LENGTH: 101 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:25:

CATACCGCGC  TTTATGCCGC  CATCTTGATG  TTTTCCCATA  CCGGCGGGGG  GGGGGGCGA         60

TGGCGCAAAC  CCATCAATAC  GCTATTATCA  TGAACGAGCG  A                           101

( 2 ) INFORMATION FOR SEQ ID NO:26:

( i ) SEQUENCE CHARACTERISTICS:
        ( A ) LENGTH: 100 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:26:
```

( 2 ) INFORMATION FOR SEQ ID NO:27:

( i ) SEQUENCE CHARACTERISTICS:
        ( A ) LENGTH: 99 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..99

( x i ) SEQUENCE DESCRIPTION: SEQ ID NO:27:

```
CAT ACC GCG CTT TAT GCC GCC ATC TTG ATG TTT TCC CAT ACC GGC GGG     48
His Thr Ala Leu Tyr Ala Ala Ile Leu Met Phe Ser His Thr Gly Gly
 1               5                  10                  15

GGG GGG GCG ATG GCG CAA ACC CAT CAA TAC GCT ATT ATC ATG AAC GAG     96
Gly Gly Ala Met Ala Gln Thr His Gln Tyr Ala Ile Ile Met Asn Glu
             20                  25                  30

CGA                                                                 99
Arg
```

( 2 ) INFORMATION FOR SEQ ID NO:28:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

```
His Thr Ala Leu Tyr Ala Ala Ile Leu Met Phe Ser His Thr Gly Gly
 1               5                  10                  15

Gly Gly Ala Met Ala Gln Thr His Gln Tyr Ala Ile Ile Met Asn Glu
             20                  25                  30

Arg
```

( 2 ) INFORMATION FOR SEQ ID NO:29:

( i ) SEQUENCE CHARACTERISTICS:
        ( A ) LENGTH: 739 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:29:

```
CCGCTGTATG TGTATGATTT GGAAAACACC AGTGGTAGTC TGATTAAAAA AATCGAAGCA     60
CCCGGCGGCA AAGGCGGGCT TTCGTCCCCC ACGCTGGTGG ATAAAGATTT GGACGGCACG    120
GTCGATATCG CCTATGCCGG CGACCGGGGC GGCAATATGT ACCGCTTTGA TTTGAGCAAT    180
TCCGATTCTA GTAAATGGTC TGCAAAGGTT ATTTTCGAAG GCGACAAGCC GATTACCTCC    240
GCGCCCGCCG TTTCCCGACT GGCAGACAAA CGCGTGGTTA TCTTCGGCAC GGGCAGCGAT    300
TTGAGTGAAC AGGATGTACT GGATACGGAC AAACAATATA TTTACGGTAT CTTTGACGAC    360
GATAAGTCGA CGGTTAATGT AAAGGTAACA AACGGCACGG GAGGCGGGCT GCTCGAGCAA    420
GTGCTTAAAG AGGAAAGTAA AACCTTATTC CTGAGCAATA ATAAGGCATC CGGCGGATCG    480
```

CATACCGCGC TTTATGCCGC CATCTTGATG TTTTCCCATA CCGGCGGGGG GGGGGGCGAT 60
GGCGCAAACC CATCAATACG CTATTATCAT GAACGAGCGA 100

```
GCCGATAAAG  GGTGGGTAGT  GAAATTGAGG  GAAGGAGAAC  GCGTTACCGT  CAAACCGACC      540

GTGGTATTGC  GTACCGCCTT  TGTCACCATC  CGCAAATATA  CGGATACGGA  CAAATGTGGC      600

GCGCAAACCG  CCATTTTGGG  CATCAATACC  GCCGACGGCG  GCGCATTGAC  TCCGAGAAGC      660

GCGCGCCCGA  TTGTGCCGGA  TCACAATTCG  GTTGCGCAAT  ATTCCGGCCA  TCAGAAAATG      720

AACGGCAAGT  CCATCCCGG                                                       739
```

( 2 ) INFORMATION FOR SEQ ID NO:30:

( i ) SEQUENCE CHARACTERISTICS:
        ( A ) LENGTH: 739 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..738

( x i ) SEQUENCE DESCRIPTION: SEQ ID NO:30:

```
CCG  CTG  TAT  GTG  TAT  GAT  TTG  GAA  AAC  ACC  AGT  GGT  AGT  CTG  ATT  AAA       48
Pro  Leu  Tyr  Val  Tyr  Asp  Leu  Glu  Asn  Thr  Ser  Gly  Ser  Leu  Ile  Lys
 1                  5                        10                       15

AAA  ATC  GAA  GCA  CCC  GGC  GGC  AAA  GGC  GGG  CTT  TCG  TCC  CCC  ACG  CTG       96
Lys  Ile  Glu  Ala  Pro  Gly  Gly  Lys  Gly  Gly  Leu  Ser  Ser  Pro  Thr  Leu
                20                        25                       30

GTG  GAT  AAA  GAT  TTG  GAC  GGC  ACG  GTC  GAT  ATC  GCC  TAT  GCC  GGC  GAC      144
Val  Asp  Lys  Asp  Leu  Asp  Gly  Thr  Val  Asp  Ile  Ala  Tyr  Ala  Gly  Asp
           35                        40                       45

CGG  GGC  GGC  AAT  ATG  TAC  CGC  TTT  GAT  TTG  AGC  AAT  TCC  GAT  TCT  AGT      192
Arg  Gly  Gly  Asn  Met  Tyr  Arg  Phe  Asp  Leu  Ser  Asn  Ser  Asp  Ser  Ser
      50                        55                       60

AAA  TGG  TCT  GCA  AAG  GTT  ATT  TTC  GAA  GGC  GAC  AAG  CCG  ATT  ACC  TCC      240
Lys  Trp  Ser  Ala  Lys  Val  Ile  Phe  Glu  Gly  Asp  Lys  Pro  Ile  Thr  Ser
 65                       70                       75                       80

GCG  CCC  GCC  GTT  TCC  CGA  CTG  GCA  GAC  AAA  CGC  GTG  GTT  ATC  TTC  GGC      288
Ala  Pro  Ala  Val  Ser  Arg  Leu  Ala  Asp  Lys  Arg  Val  Val  Ile  Phe  Gly
                     85                       90                       95

ACG  GGC  AGC  GAT  TTG  AGT  GAA  CAG  GAT  GTA  CTG  GAT  ACG  GAC  AAA  CAA      336
Thr  Gly  Ser  Asp  Leu  Ser  Glu  Gln  Asp  Val  Leu  Asp  Thr  Asp  Lys  Gln
               100                       105                      110

TAT  ATT  TAC  GGT  ATC  TTT  GAC  GAC  GAT  AAG  TCG  ACG  GTT  AAT  GTA  AAG      384
Tyr  Ile  Tyr  Gly  Ile  Phe  Asp  Asp  Asp  Lys  Ser  Thr  Val  Asn  Val  Lys
          115                       120                      125

GTA  ACA  AAC  GGC  ACG  GGA  GGC  GGG  CTC  CTC  GAG  CAA  GTG  CTT  AAA  GAG      432
Val  Thr  Asn  Gly  Thr  Gly  Gly  Gly  Leu  Leu  Glu  Gln  Val  Leu  Lys  Glu
     130                      135                      140

GAA  AGT  AAA  ACC  TTA  TTC  CTG  AGC  AAT  AAT  AAG  GCA  TCC  GGC  GGA  TCG      480
Glu  Ser  Lys  Thr  Leu  Phe  Leu  Ser  Asn  Asn  Lys  Ala  Ser  Gly  Gly  Ser
145                       150                      155                      160

GCC  GAT  AAA  GGG  TGG  GTA  GTG  AAA  TTG  AGG  GAA  GGA  GAA  CGC  GTT  ACC      528
Ala  Asp  Lys  Gly  Trp  Val  Val  Lys  Leu  Arg  Glu  Gly  Glu  Arg  Val  Thr
                     165                      170                      175

GTC  AAA  CCG  ACC  GTG  GTA  TTG  CGT  ACC  GCC  TTT  GTC  ACC  ATC  CGC  AAA      576
Val  Lys  Pro  Thr  Val  Val  Leu  Arg  Thr  Ala  Phe  Val  Thr  Ile  Arg  Lys
               180                      185                      190

TAT  ACG  GAT  ACG  GAC  AAA  TGT  GGC  GCG  CAA  ACC  GCC  ATT  TTG  GGC  ATC      624
Tyr  Thr  Asp  Thr  Asp  Lys  Cys  Gly  Ala  Gln  Thr  Ala  Ile  Leu  Gly  Ile
          195                      200                      205

AAT  ACC  GCC  GAC  GGC  GGC  GCA  TTG  ACT  CCG  AGA  AGC  GCG  CGC  CCG  ATT      672
```

| | | | | | | | | | | | | | | |
|---|---|---|---|---|---|---|---|---|---|---|---|---|---|---|
| Asn | Thr | Ala | Asp | Gly | Gly | Ala | Leu | Thr | Pro | Arg | Ser | Ala | Arg | Pro | Ile |
| | 210 | | | | 215 | | | | | 220 | | | | | |

| GTG | CCG | GAT | CAC | AAT | TCG | GTT | GCG | CAA | TAT | TCC | GGC | CAT | CAG | AAA | ATG | 720 |
|---|---|---|---|---|---|---|---|---|---|---|---|---|---|---|---|---|
| Val | Pro | Asp | His | Asn | Ser | Val | Ala | Gln | Tyr | Ser | Gly | His | Gln | Lys | Met | |
| 225 | | | | | 230 | | | | | 235 | | | | | 240 | |

| AAC | GGC | AAG | TCC | ATC | CCG | G | | | | | | | | | | 739 |
|---|---|---|---|---|---|---|---|---|---|---|---|---|---|---|---|---|
| Asn | Gly | Lys | Ser | Ile | Pro | | | | | | | | | | | |
| | | | | 245 | | | | | | | | | | | | |

( 2 ) INFORMATION FOR SEQ ID NO:31:

( i ) SEQUENCE CHARACTERISTICS:
        ( A ) LENGTH: 246 amino acids
        ( B ) TYPE: amino acid
        ( D ) TOPOLOGY: linear ( i i ) MOLECULE TYPE: protein ( x i ) SEQUENCE DESCRIPTION: SEQ ID NO:31:

| Pro | Leu | Tyr | Val | Tyr | Asp | Leu | Glu | Asn | Thr | Ser | Gly | Ser | Leu | Ile | Lys |
|---|---|---|---|---|---|---|---|---|---|---|---|---|---|---|---|
| 1 | | | | 5 | | | | | 10 | | | | | 15 | |
| Lys | Ile | Glu | Ala | Pro | Gly | Gly | Lys | Gly | Gly | Leu | Ser | Ser | Pro | Thr | Leu |
| | | | 20 | | | | | 25 | | | | | 30 | | |
| Val | Asp | Lys | Asp | Leu | Asp | Gly | Thr | Val | Asp | Ile | Ala | Tyr | Ala | Gly | Asp |
| | | | 35 | | | | 40 | | | | | 45 | | | |
| Arg | Gly | Gly | Asn | Met | Tyr | Arg | Phe | Asp | Leu | Ser | Asn | Ser | Asp | Ser | Ser |
| | 50 | | | | | 55 | | | | | 60 | | | | |
| Lys | Trp | Ser | Ala | Lys | Val | Ile | Phe | Glu | Gly | Asp | Lys | Pro | Ile | Thr | Ser |
| 65 | | | | | 70 | | | | | 75 | | | | | 80 |
| Ala | Pro | Ala | Val | Ser | Arg | Leu | Ala | Asp | Lys | Arg | Val | Val | Ile | Phe | Gly |
| | | | | 85 | | | | | 90 | | | | | 95 | |
| Thr | Gly | Ser | Asp | Leu | Ser | Glu | Gln | Asp | Val | Leu | Asp | Thr | Asp | Lys | Gln |
| | | | 100 | | | | | 105 | | | | | 110 | | |
| Tyr | Ile | Tyr | Gly | Ile | Phe | Asp | Asp | Asp | Lys | Ser | Thr | Val | Asn | Val | Lys |
| | | | 115 | | | | 120 | | | | | 125 | | | |
| Val | Thr | Asn | Gly | Thr | Gly | Gly | Leu | Leu | Glu | Gln | Val | Leu | Lys | Glu |
| | 130 | | | | | 135 | | | | | 140 | | | | |
| Glu | Ser | Lys | Thr | Leu | Phe | Leu | Ser | Asn | Asn | Lys | Ala | Ser | Gly | Gly | Ser |
| 145 | | | | | 150 | | | | | 155 | | | | | 160 |
| Ala | Asp | Lys | Gly | Trp | Val | Val | Lys | Leu | Arg | Glu | Gly | Glu | Arg | Val | Thr |
| | | | | 165 | | | | | 170 | | | | | 175 | |
| Val | Lys | Pro | Thr | Val | Val | Leu | Arg | Thr | Ala | Phe | Val | Thr | Ile | Arg | Lys |
| | | | 180 | | | | | 185 | | | | | 190 | | |
| Tyr | Thr | Asp | Thr | Asp | Lys | Cys | Gly | Ala | Gln | Thr | Ala | Ile | Leu | Gly | Ile |
| | | | 195 | | | | | 200 | | | | | 205 | | |
| Asn | Thr | Ala | Asp | Gly | Gly | Ala | Leu | Thr | Pro | Arg | Ser | Ala | Arg | Pro | Ile |
| | 210 | | | | | 215 | | | | | 220 | | | | |
| Val | Pro | Asp | His | Asn | Ser | Val | Ala | Gln | Tyr | Ser | Gly | His | Gln | Lys | Met |
| 225 | | | | | 230 | | | | | 235 | | | | | 240 |
| Asn | Gly | Lys | Ser | Ile | Pro | | | | | | | | | | |
| | | | | 245 | | | | | | | | | | | |

( 2 ) INFORMATION FOR SEQ ID NO:32:

( i ) SEQUENCE CHARACTERISTICS:
        ( A ) LENGTH: 733 base pairs
        ( B ) TYPE: nucleic acid
        ( C ) STRANDEDNESS: double
        ( D ) TOPOLOGY: linear 5,834,591

93

94

-continued ( i x ) FEATURE:
    ( A ) NAME/KEY: CDS
    ( B ) LOCATION: 1..732

( x i ) SEQUENCE DESCRIPTION: SEQ ID NO:32:

| GCG | CTG | TAT | GTA | TAT | GAT | TTG | AAA | GAC | ACC | TTA | GGT | ACG | CCG | ATT | GCA | 48 |
|---|---|---|---|---|---|---|---|---|---|---|---|---|---|---|---|---|
| Ala | Leu | Tyr | Val | Tyr | Asp | Leu | Lys | Asp | Thr | Leu | Gly | Thr | Pro | Ile | Ala | |
| 1 | | | | 5 | | | | | 10 | | | | | 15 | | |

| AAA | ATC | GAA | GTG | AAG | GAC | GGC | AAA | GGC | GGG | CTT | TCG | TCC | CCC | ACG | CTG | 96 |
|---|---|---|---|---|---|---|---|---|---|---|---|---|---|---|---|---|
| Lys | Ile | Glu | Val | Lys | Asp | Gly | Lys | Gly | Gly | Leu | Ser | Ser | Pro | Thr | Leu | |
| | | | 20 | | | | | 25 | | | | | 30 | | | |

| GTG | GAT | AAA | GAT | TTG | GAC | GGC | ACG | GTC | GAT | ATC | GCC | TAT | GCC | GGC | GAC | 144 |
|---|---|---|---|---|---|---|---|---|---|---|---|---|---|---|---|---|
| Val | Asp | Lys | Asp | Leu | Asp | Gly | Thr | Val | Asp | Ile | Ala | Tyr | Ala | Gly | Asp | |
| | | 35 | | | | | 40 | | | | | 45 | | | | |

| CGG | GGC | GGC | AAT | ATG | TAC | CGC | TTT | GAT | TTG | AGC | AAT | TCC | GAT | TCT | AGT | 192 |
|---|---|---|---|---|---|---|---|---|---|---|---|---|---|---|---|---|
| Arg | Gly | Gly | Asn | Met | Tyr | Arg | Phe | Asp | Leu | Ser | Asn | Ser | Asp | Ser | Ser | |
| | 50 | | | | | 55 | | | | | 60 | | | | | |

| AAA | TGG | TCT | GCA | AAG | GTT | ATT | TTC | GAA | GGC | GAC | AAG | CCG | ATT | ACC | TCC | 240 |
|---|---|---|---|---|---|---|---|---|---|---|---|---|---|---|---|---|
| Lys | Trp | Ser | Ala | Lys | Val | Ile | Phe | Glu | Gly | Asp | Lys | Pro | Ile | Thr | Ser | |
| 65 | | | | | 70 | | | | | 75 | | | | | 80 | |

| GCG | CCC | GCC | GTT | TCC | CGA | CTG | GCA | GAC | AAA | CGC | GTC | GTC | ATC | TTC | GGT | 288 |
|---|---|---|---|---|---|---|---|---|---|---|---|---|---|---|---|---|
| Ala | Pro | Ala | Val | Ser | Arg | Leu | Ala | Asp | Lys | Arg | Val | Val | Ile | Phe | Gly | |
| | | | | 85 | | | | | 90 | | | | | 95 | | |

| ACG | GGC | AGC | GAT | TTG | ACC | GAA | GAT | GAT | GTA | CTG | AAT | ACG | GGC | GAA | CAA | 336 |
|---|---|---|---|---|---|---|---|---|---|---|---|---|---|---|---|---|
| Thr | Gly | Ser | Asp | Leu | Thr | Glu | Asp | Asp | Val | Leu | Asn | Thr | Gly | Glu | Gln | |
| | | | 100 | | | | | 105 | | | | | 110 | | | |

| TAT | ATT | TAC | GGT | ATC | TTT | GAC | GAC | GAT | AAG | GGG | ACG | GTT | AAG | GTA | ACG | 384 |
|---|---|---|---|---|---|---|---|---|---|---|---|---|---|---|---|---|
| Tyr | Ile | Tyr | Gly | Ile | Phe | Asp | Asp | Asp | Lys | Gly | Thr | Val | Lys | Val | Thr | |
| | | 115 | | | | | 120 | | | | | 125 | | | | |

| GTA | CAA | AAC | GGC | ACG | GCA | GGC | GGG | CTG | CTC | GAG | CAA | CAC | CTT | ACT | CAG | 432 |
|---|---|---|---|---|---|---|---|---|---|---|---|---|---|---|---|---|
| Val | Gln | Asn | Gly | Thr | Ala | Gly | Gly | Leu | Leu | Glu | Gln | His | Leu | Thr | Gln | |
| | 130 | | | | | 135 | | | | | 140 | | | | | |

| GAA | AAT | AAA | ACA | TTA | TTC | CTG | AAC | AAG | AGA | TCC | GAC | GGT | TCG | GGC | AGC | 480 |
|---|---|---|---|---|---|---|---|---|---|---|---|---|---|---|---|---|
| Glu | Asn | Lys | Thr | Leu | Phe | Leu | Asn | Lys | Arg | Ser | Asp | Gly | Ser | Gly | Ser | |
| 145 | | | | | 150 | | | | | 155 | | | | | 160 | |

| AAG | GGC | TGG | GCG | GTG | AAA | TTG | AGG | GAA | GGA | GAA | CGC | GTT | ACC | GTC | AAA | 528 |
|---|---|---|---|---|---|---|---|---|---|---|---|---|---|---|---|---|
| Lys | Gly | Trp | Ala | Val | Lys | Leu | Arg | Glu | Gly | Glu | Arg | Val | Thr | Val | Lys | |
| | | | | 165 | | | | | 170 | | | | | 175 | | |

| CCG | ACC | GTG | GTA | TTG | CGT | ACC | GCC | TTC | GTA | ACC | ATC | CGC | AAA | TAT | AAC | 576 |
|---|---|---|---|---|---|---|---|---|---|---|---|---|---|---|---|---|
| Pro | Thr | Val | Val | Leu | Arg | Thr | Ala | Phe | Val | Thr | Ile | Arg | Lys | Tyr | Asn | |
| | | | 180 | | | | | 185 | | | | | 190 | | | |

| GAC | GGC | GGC | TGC | GGC | GCG | GAA | ACC | GCC | ATT | TTG | GGC | ATC | AAT | ACC | GCC | 624 |
|---|---|---|---|---|---|---|---|---|---|---|---|---|---|---|---|---|
| Asp | Gly | Gly | Cys | Gly | Ala | Glu | Thr | Ala | Ile | Leu | Gly | Ile | Asn | Thr | Ala | |
| | | 195 | | | | | 200 | | | | | 205 | | | | |

| GAC | GGC | GGC | GCA | TTG | ACT | CCG | AGA | AGC | GCG | CGC | CCG | ATT | GTG | CCG | GAT | 672 |
|---|---|---|---|---|---|---|---|---|---|---|---|---|---|---|---|---|
| Asp | Gly | Gly | Ala | Leu | Thr | Pro | Arg | Ser | Ala | Arg | Pro | Ile | Val | Pro | Asp | |
| | | 210 | | | | | 215 | | | | | 220 | | | | |

| CAC | AAT | TCG | GTT | GCG | CAA | TAT | TCC | GGC | CAT | AAG | ACA | ACC | TCC | AAA | GGC | 720 |
|---|---|---|---|---|---|---|---|---|---|---|---|---|---|---|---|---|
| His | Asn | Ser | Val | Ala | Gln | Tyr | Ser | Gly | His | Lys | Thr | Thr | Ser | Lys | Gly | |
| 225 | | | | | 230 | | | | | 235 | | | | | 240 | |

| AAA | TCC | ATC | CCA | T | | | | | | | | | | | | 733 |
|---|---|---|---|---|---|---|---|---|---|---|---|---|---|---|---|---|
| Lys | Ser | Ile | Pro | | | | | | | | | | | | | |

( 2 ) INFORMATION FOR SEQ ID NO:33:

( i ) SEQUENCE CHARACTERISTICS:
        ( A ) LENGTH: 244 amino acids
        ( B ) TYPE: amino acid
        ( D ) TOPOLOGY: linear ( i i ) MOLECULE TYPE: protein ( x i ) SEQUENCE DESCRIPTION: SEQ ID NO:33:

| | | | | | | | | | | | | | | |
|---|---|---|---|---|---|---|---|---|---|---|---|---|---|---|
| Ala | Leu | Tyr | Val | Tyr | Asp | Leu | Lys | Asp | Thr | Leu | Gly | Thr | Pro | Ile | Ala |
| 1 | | | | 5 | | | | | 10 | | | | | 15 | |
| Lys | Ile | Glu | Val | Lys | Asp | Gly | Lys | Gly | Leu | Ser | Ser | Pro | Thr | Leu |
| | | | 20 | | | | | 25 | | | | 30 | | |
| Val | Asp | Lys | Asp | Leu | Asp | Gly | Thr | Val | Asp | Ile | Ala | Tyr | Ala | Gly | Asp |
| | | 35 | | | | | 40 | | | | | 45 | | | |
| Arg | Gly | Gly | Asn | Met | Tyr | Arg | Phe | Asp | Leu | Ser | Asn | Ser | Asp | Ser | Ser |
| | 50 | | | | | 55 | | | | | 60 | | | | |
| Lys | Trp | Ser | Ala | Lys | Val | Ile | Phe | Glu | Gly | Asp | Lys | Pro | Ile | Thr | Ser |
| 65 | | | | | 70 | | | | | 75 | | | | | 80 |
| Ala | Pro | Ala | Val | Ser | Arg | Leu | Ala | Asp | Lys | Arg | Val | Val | Ile | Phe | Gly |
| | | | | 85 | | | | | 90 | | | | | 95 | |
| Thr | Gly | Ser | Asp | Leu | Thr | Glu | Asp | Asp | Val | Leu | Asn | Thr | Gly | Glu | Gln |
| | | | 100 | | | | | 105 | | | | | 110 | | |
| Tyr | Ile | Tyr | Gly | Ile | Phe | Asp | Asp | Lys | Gly | Thr | Val | Lys | Val | Thr |
| | | 115 | | | | | 120 | | | | | 125 | | | |
| Val | Gln | Asn | Gly | Thr | Ala | Gly | Gly | Leu | Leu | Glu | Gln | His | Leu | Thr | Gln |
| | | 130 | | | | | 135 | | | | | 140 | | | |
| Glu | Asn | Lys | Thr | Leu | Phe | Leu | Asn | Lys | Arg | Ser | Asp | Gly | Ser | Gly | Ser |
| 145 | | | | | 150 | | | | | 155 | | | | | 160 |
| Lys | Gly | Trp | Ala | Val | Lys | Leu | Arg | Glu | Gly | Glu | Arg | Val | Thr | Val | Lys |
| | | | | 165 | | | | | 170 | | | | | 175 | |
| Pro | Thr | Val | Val | Leu | Arg | Thr | Ala | Phe | Val | Thr | Ile | Arg | Lys | Tyr | Asn |
| | | | 180 | | | | | 185 | | | | | 190 | | |
| Asp | Gly | Gly | Cys | Gly | Ala | Glu | Thr | Ala | Ile | Leu | Gly | Ile | Asn | Thr | Ala |
| | | 195 | | | | | 200 | | | | | 205 | | | |
| Asp | Gly | Gly | Ala | Leu | Thr | Pro | Arg | Ser | Ala | Arg | Pro | Ile | Val | Pro | Asp |
| | 210 | | | | | 215 | | | | | 220 | | | | |
| His | Asn | Ser | Val | Ala | Gln | Tyr | Ser | Gly | His | Lys | Thr | Thr | Ser | Lys | Gly |
| 225 | | | | | 230 | | | | | 235 | | | | | 240 |
| Lys | Ser | Ile | Pro |

( 2 ) INFORMATION FOR SEQ ID NO:34:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

GGCGCAGGCG CA                              12

( 2 ) INFORMATION FOR SEQ ID NO:35:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

GGCGCAGGCG CAGGCGCA                      18

( 2 ) INFORMATION FOR SEQ ID NO:36:

( i ) SEQUENCE CHARACTERISTICS:
        ( A ) LENGTH: 16 base pairs
        ( B ) TYPE: nucleic acid ( C ) STRANDEDNESS: single
( D ) TOPOLOGY: linear ( x i ) SEQUENCE DESCRIPTION: SEQ ID NO:36:

GGCAGGCGCA GGCGCA 16

( 2 ) INFORMATION FOR SEQ ID NO:37:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:37:

GCCTTTTTGA AGGGTATTCA T 21

( 2 ) INFORMATION FOR SEQ ID NO:38:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( x i ) SEQUENCE DESCRIPTION: SEQ ID NO:38:

GGCTAGGTGG CATATGAAAG ATACCGG 27

( 2 ) INFORMATION FOR SEQ ID NO:39:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:39:

TTTGCAATCG GGGATCCTCA GGTGTCTTTC 30

( 2 ) INFORMATION FOR SEQ ID NO:40:

( i ) SEQUENCE CHARACTERISTICS:
( A ) LENGTH: 200 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 33..155

( x i ) SEQUENCE DESCRIPTION: SEQ ID NO:40:

| CGTCCCGCGA | AGGCAAACTT | AAGGAATAAA | AT | ATG | AAT | AAA | ACT | TTG | AAA | CGG | 53 |
| | | | | Met | Asn | Lys | Thr | Leu | Lys | Arg | |
| | | | | 1 | | | | 5 | | | |

| CAG | GTT | TTC | CGC | CAT | ACC | GCG | CTT | TAT | GCC | GCC | ATC | TTG | ATG | TTT | TCC | 101 |
| Gln | Val | Phe | Arg | His | Thr | Ala | Leu | Tyr | Ala | Ala | Ile | Leu | Met | Phe | Ser | |
| | 10 | | | | | 15 | | | | | 20 | | | | | |

| CAT | ACC | GGC | GGG | GGG | GGG | CGA | TGG | CGC | AAA | CCC | ATC | AAT | ACG | CTA | 149 |
| His | Thr | Gly | Gly | Gly | Gly | Gly | Arg | Trp | Arg | Lys | Pro | Ile | Asn | Thr | Leu | |
| | 25 | | | | | 30 | | | | | 35 | | | | | |

| TTA | TCA | TGAACGAGCG | AAACCAGCCC | GAGGTAAAGC | AGAATGTGCC | ATCTT | 200 |
| Leu | Ser | | | | | | |
| 40 | | | | | | | |

(2) INFORMATION FOR SEQ ID NO:41:

(i) SEQUENCE CHARACTERISTICS:
(A) LENGTH: 41 amino acids
(B) TYPE: amino acid
(D) TOPOLOGY: linear (ii) MOLECULE TYPE: protein (xi) SEQUENCE DESCRIPTION: SEQ ID NO:41:

| Met | Asn | Lys | Thr | Leu | Lys | Arg | Gln | Val | Phe | Arg | His | Thr | Ala | Leu | Tyr |
|---|---|---|---|---|---|---|---|---|---|---|---|---|---|---|---|
| 1 | | | | 5 | | | | | 10 | | | | | 15 | |

| Ala | Ala | Ile | Leu | Met | Phe | Ser | His | Thr | Gly | Gly | Gly | Gly | Gly | Arg | Trp |
|---|---|---|---|---|---|---|---|---|---|---|---|---|---|---|---|
| | | | | 20 | | | | 25 | | | | | 30 | | |

| Arg | Lys | Pro | Ile | Asn | Thr | Leu | Leu | Ser |
|---|---|---|---|---|---|---|---|---|
| | | | 35 | | | | 40 | |

(2) INFORMATION FOR SEQ ID NO:42:

(i) SEQUENCE CHARACTERISTICS:
(A) LENGTH: 200 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 125..200

(xi) SEQUENCE DESCRIPTION: SEQ ID NO:42:

CGTCCCGCGA AGGCAAACTT AAGGAATAAA ATATGAATAA AACTTTGAAA CGGCAGGTTT    60

TCCGCCATAC CGCGCTTTAT GCCGCCATCT TGATGTTTTC CCATACCGGC GGGGGGGGGG    120

| GGCG | ATG | GCG | CAA | ACC | CAT | CAA | TAC | GCT | ATT | ATC | ATG | AAC | GAG | CGA | AAC | 169 |
|---|---|---|---|---|---|---|---|---|---|---|---|---|---|---|---|---|
| | Met | Ala | Gln | Thr | His | Gln | Tyr | Ala | Ile | Ile | Met | Asn | Glu | Arg | Asn | |
| | 1 | | | | 5 | | | | | 10 | | | | | 15 | |

| CAG | CCC | GAG | GTA | AAG | CAG | AAT | GTG | CCA | TCT | T | 200 |
|---|---|---|---|---|---|---|---|---|---|---|---|
| Gln | Pro | Glu | Val | Lys | Gln | Asn | Val | Pro | Ser | | |
| | | | 20 | | | | | 25 | | | |

(2) INFORMATION FOR SEQ ID NO:43:

(i) SEQUENCE CHARACTERISTICS:
(A) LENGTH: 25 amino acids
(B) TYPE: amino acid
(D) TOPOLOGY: linear (ii) MOLECULE TYPE: protein (xi) SEQUENCE DESCRIPTION: SEQ ID NO:43:

| Met | Ala | Gln | Thr | His | Gln | Tyr | Ala | Ile | Ile | Met | Asn | Glu | Arg | Asn | Gln |
|---|---|---|---|---|---|---|---|---|---|---|---|---|---|---|---|
| 1 | | | | 5 | | | | | 10 | | | | | 15 | |

| Pro | Glu | Val | Lys | Gln | Asn | Val | Pro | Ser |
|---|---|---|---|---|---|---|---|---|
| | | | 20 | | | | 25 | |

POLYPEPTIDES AND ANTIBODIES USEFUL FOR THE DIAGNOSIS AND TREATMENT OF PATHOGENIC NEISSERIA AND OTHER MICROORGANISMS HAVING TYPE 4 PILIN

CROSS-REFERENCE TO RELATED APPLICATIONS

This application is a continuation, of application Ser. No. 07/829,465, filed Jan. 31, 1992 now abandoned, which application is a continuation-in-part of U.S. Ser. No. 07/648, 781 filed 31 Jan. 1991, which is incorporated by reference herein in its entirety.

This invention was made with Government support under Grant No. GM 44655 awarded by the National Institutes of Health. The Government has certain rights in the invention.

TECHNICAL FIELD

The invention relates to materials and methodologies for managing the spread of infections caused by microorganisms having type 4 pilin, for example, Neisseria. More specifically, it relates to polypeptides and antibodies useful in vaccines for the treatment of pathologic infections caused by these microorganisms. It also relates to polynucleotides useful for the recombinant production of these polypeptides. In addition, it relates to polypeptides, antibodies, and polynucleotides used for the detection of these strains.

BACKGROUND ART

Type 4 pilins are expressed by several bacterial genuses, including Neisseria, Moraxella, Bacteroides, and Pseudomonas. Species within these genuses which have pathogenic members that express type 4 pilins are, for example, *N. gonorrhoeae, N. meningitidis, M. bovis, B. nodosus*, and *P. aeruginosa*. In addition, the Tcp pilin of *V. cholerae* is highly homologous to the type 4 pilins of other genuses.

The only known reservoir of the neisseriae is man. The genus includes two gram-negative species of pyogenic cocci that are pathogenic for man: the meningococcus (*Neisseria meningitidis*) and the gonococcus (*Neisseria gonorrheae*).

*N. Meningitidis* causes a variety of infections, most notably, meningitis and bacteremia. Meningococci can be divided into serologic groups on the basis of agglutination reactions with immune serum. The present classification includes groups A through Z. Clinically significant new groups encompass Y and W 135. The major groups are remarkably heterogeneous, but subclassification with additional serologic markers has been possible. Noncapsular antigens have provided the basis for dividing strains of groups into distinct types.

Meningococci cause either epidemic or sporadic disease, and historically, there has been a cyclic variation in the prevalence of meningococcal infection with peaks of increased frequency occurring every 8 to 12 years and lasting 4 to 6 years. The attack rate of meningococcal disease is highest for children between 6 months and 1 year. In the first half of this century, most epidemics of meningococcal disease in the United States were caused by group A organisms. In the past two decades, first group B then group C meningococci were responsible for outbreaks in both the military and civilian populations. Currently, group B is responsible for 50 to 55 percent of reported cases.

Gonorrhea, which is caused by *N. gonorrhea*, is an infection of columnar and transitional epithelium. This disease is the most common reportable communicable disease in the United States, and also has world-wide prevalence.

Although treatment of disease caused by gonococci and meningococci are often treated with antibiotics, these microorganisms often develop antibiotic resistance. Thus, prevention with vaccines is a preferable mode to contain the spread of infection. However, for a variety of reasons, including antigenic variation, the development of vaccines has been greatly hampered. For example, a vaccine which prevents gonorrhea is still lacking. In addition, although 56% of the causes of meningococcal disease are caused by serogroup B, an effective vaccine against this serogroup is also lacking.

*N. gonorrheae* and *N. meningitidis* are organisms completely adapted to the human host, having no other ecological niche. They have acquired a large arsenal of strategies to overcome the human host defense system.

The first step in infection with pathological forms of these Neisseria is adherence to target cells. It is thought that the pili of these microorganisms are a major virulence factor. For example, it is known that in the case of *N. gonorrheae*, piliated ($P^+$) variants attach much better to susceptible cells than non-piliated (P−) variants (Swanson, 1973; Pearce and Buchanan, 1978). Moreover, P+ variants, unlike P− variants, are able to establish an infection in human volunteers (Kellog et al, 1968).

Although the pilus protein elicits an immune response, so many antigenic variants exist and continue to develop that vaccines against the pilus protein are not highly effective.

Pilin is the major subunit of the pilus. Expression of pilin is controlled at the pilE locus.

BRIEF DESCRIPTION OF THE INVENTION

We have isolated and characterized a novel protein of pathogenic forms of Neisseria, PilC, that may be is associated with the pili of gonococci and meningococci. We have also isolated and characterized genes which encode PilC, i.e., the pilC loci.

Portions of the DNA sequences of the pilC genes are useful as probes to diagnose the presence of the relevant Neisseria in samples. These DNAs also make available polypeptide sequences of immunoreactive epitopes encoded within the loci, thus permitting the production of polypeptides which are useful as standards or reagents in diagnostic tests and/or as components of vaccines for microorganisms with type 4 pilin and containing one or more epitopes that are immunologically identifiable with an epitope encoded in pilC of Neisseria. Antibodies, both monoclonal and purified polyclonal, directed against PilC epitopes are also useful for diagnostic tests and as therapeutic agents for passive immunization. In addition, by utilizing probes derived from the DNA sequences, it is possible to isolate and sequence portions of the pilC loci from species and strains of interest.

Accordingly, one embodiment of the invention is a recombinant polynucleotide encoding a polypeptide comprised of an immunoreactive epitope of a protein encoded in pilC of Neisseria.

Another embodiment of the invention is a recombinant expression system comprising a polynucleotide encoding a polypeptide comprised of an immunoreactive epitope of a protein encoded in pilC of Neisseria, wherein the polynucleotide is operably linked to a control sequence compatible with a desired host.

Yet another embodiment of the invention is purified polypeptide comprised of an immunoreactive epitope of a protein encoded in pilC of Neisseria.

Another embodiment of the invention is a recombinant polypeptide comprised of an immunoreactive epitope of a protein encoded in pilC of Neisseria.

Still another embodiment of the invention is a vaccine composition for the treatment of Neisseria infection, comprised of a pharmaceutically acceptable excipient and of an effective amount of a recombinant polypeptide, wherein the polypeptide is comprised of an immunoreactive epitope of a protein encoded in pilC of Neisseria.

Yet another embodiment of the invention is a composition comprised of purified polyclonal anti-PilC antibodies, wherein the PilC is of Neisseria.

An additional embodiment of the invention is a composition comprised of a monoclonal antibody directed against an immunoreactive epitope encoded in pilC of Neisseria.

Another embodiment of the invention is a method for producing antibodies to PilC of Neisseria comprising administering to an individual a composition comprised of an isolated immunogenic polypeptide containing a PilC epitope in an amount sufficient to produce an immune response.

Yet another embodiment of the invention is an oligomer capable of hybridizing to a sequence in pilC of Neisseria, wherein the oligomer is comprised of a pilC sequence complementary to at least about 6 contiguous nucleotides of pilC.

Still another embodiment of the invention is a process for detecting a pilC sequence in an analyte strand, wherein the pilC sequence comprises a selected target region, the process comprising:

(a) providing a sample comprised of an analyte strand suspected of containing a selected target pilC sequence;

(b) providing an oligomer capable of hybridizing to the target pilC sequence, wherein the oligomer is comprised of a pilC targeting sequence complementary to at least about 6 contiguous nucleotides of pilC;

(c) incubating the sample of (a) with the oligomer of (b) under conditions which allow specific hybrid duplexes to form between the targeting sequence and the target sequence; and (d) detecting hybrids formed between the target sequence, if any, and the oligomer.

Yet another embodiment of the invention is a recombinant polynucleotide comprising a DNA sequence of at least 8 contiguous nucleotides from pilC, wherein the pilC sequence is selected from the group of sequences shown in FIG. 3, FIG. 6, and FIG. 7.

Another embodiment of the invention is a method of treating an individual for a Neisseria infection comprising administering to the individual antibodies produced according to claim 31, wherein the antibodies are administered in an amount effective to prevent the pathology of the infection.

BRIEF DESCRIPTION OF THE DRAWINGS

FIG. 2 (SEQ ID NO:40 through SEQ ID NO:43) shows the nucleotide sequence and the deduced amino acid sequence of the 5'-end of pilC1.

FIGS. 3A and 3B (SEQ ID NO:1) show the out of frame nucleotide sequence of the sense strand of the pilC1 gene.

FIGS. 4A through 4D (SEQ ID NO:2 and SEQ ID NO: 3) show the in frame nucleotide sequence of the sense strand of the pilC1 gene and the amino acids encoded therein.

FIGS. 5A through 5D (SEQ ID NO: 4 through SEQ ID NO: 7 show nucleotide sequence of the sense strand of the pilC1 gene, and the effect of frame shift on the putative gene products encoded therein.

FIG. 6 (SEQ ID NO:8 through SEQ ID NO:28) shows the nucleotide sequences of PCR amplified fragments demonstrating a variation in the length of the G tract and sequence differences in the 5' region of the pilC genes.

FIG. 7 (SEQ ID NO:29) shows the DNA sequence of the 3'-end of the pilC2 fragment.

FIG. 8 (SEQ ID NO:30 and SEQ ID NO:31) shows the pilC2 fragment sequence, and the putative amino acids encoded therein.

FIGS. 9A and 9B (SEQ ID NO: 30 through SEQ ID NO: 33) show a comparison of the analogous portions of pilC2 (top) and pilC1 (bottom) DNA sequences, and the putative amino acids encoded therein.

MODES FOR CARRYING OUT THE INVENTION

Figure 1A:
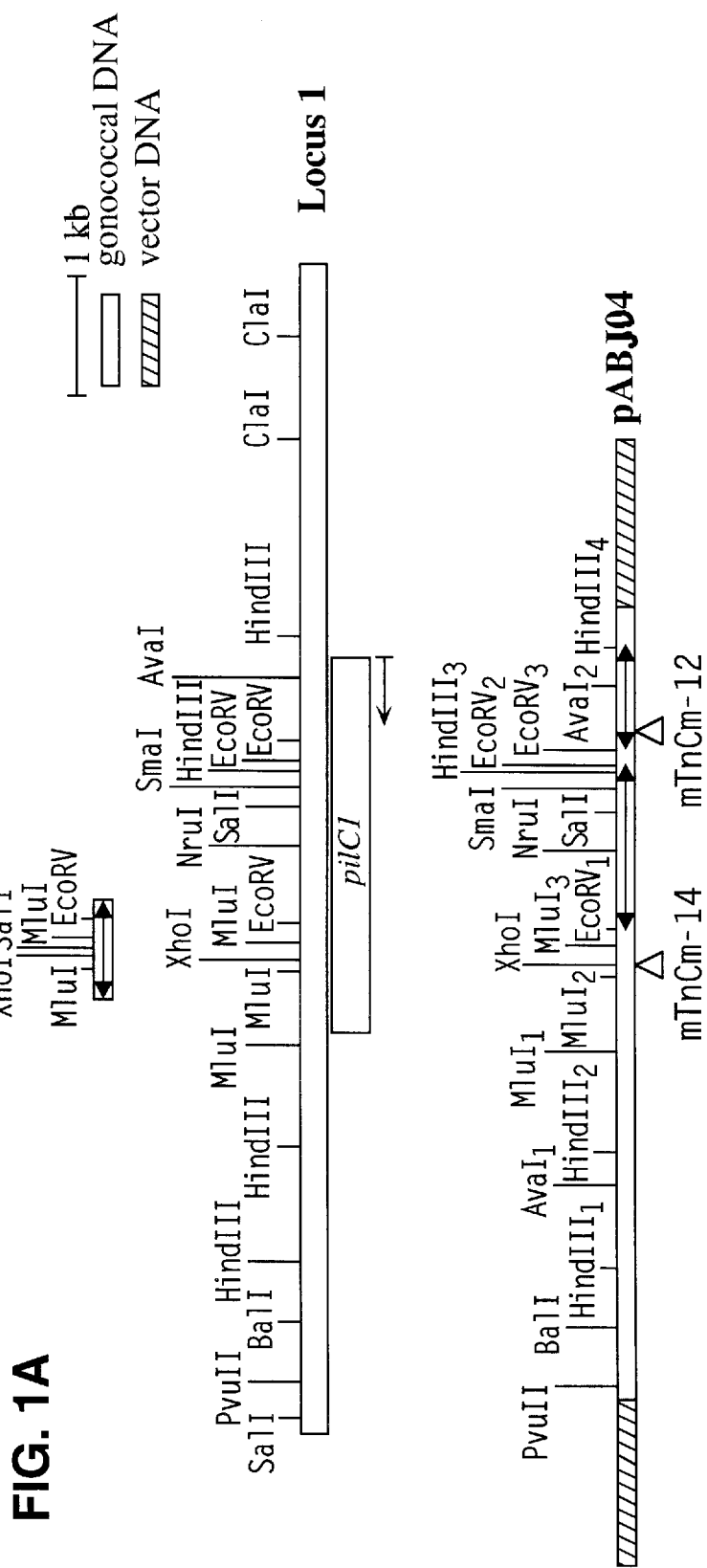
FIGS. 1A and 1B is a genetic and physical map of pilC locus 1, showing the restriction enzyme sites.

The present invention provides polypeptides, antibodies, and polynucleotides which are useful for the detection and treatment of pathogenic microorganisms having type 4 pilin, for example, Neisseria, Moraxella, Bacteroides, and Pseudomonas.

We have discovered a polypeptide, PilC, which is present in *N. gonorrheae*. This polypeptide is a 110 kd protein that is closely associated with the pili of the microorganism. Most strains of *N. gonorrheae* carry two copies of the corresponding genes which encode the polypeptide(s); these genes have been denoted pilC. Expression from the pilC loci is regulated by frequent frameshift mutations within a run of G residues in the region encoding the signal peptide. The two pilC genes of *N. gonorrheae* are not identical. Hence, alternate expression from either the pilC1 or the pilC2 loci gives rise to two different forms of PilC. Among nonpiliated (P⁻) descendants from P⁺ clones, clones were found that expressed pilin but not PilC. All P⁺ revertants from such PilC⁻ non-piliated clones have regained expression of PilC. Hence, phase variation of gonococcal pili can be caused by frameshift mutations in pilC. Transposon inactivation of the expressed pilC2 copy resulted in a nonpiliated, pilin producing revertible phenotype. It appears, therefore, that PilC is required for assembly of pilin subunits into a polymerized pilus fiber in *N. gonorrheae*.

We have cloned and isolated gene, pilC1, from *N. gonorrheae*. In addition, by comparison of this gene sequence with a related sequence, we have cloned a fragment of the pilC2 gene. Moreover, using polynucleotide probes derived from isolated pilC1 and PCR amplification, we have detected two possible variants of a pilC gene in *N. meningitidis*. The sequences of pilC reported herein appear to be novel, in that there are no reported counterparts in Genbank, and no significant homologies were found with any available sequences in that data base.

The useful materials and processes of the present invention are made possible by the provision of the sequences of the pilC genes from *N. gonorrheae* and from *N. meningitidis*. Information present in the sequences of the pilC genes allows for the design of polypeptides which may be useful as vaccines for treatment of pathogenic Neisseria, as diagnostic tools for the detection of these microorganisms, and as agents for the preparation of antibodies to PilC. In addition, this information allows for the design of polynucleotides for the recombinant production of the polypeptides derived from PilC, and for the design of oligomers which are useful as probes and primers for the detection and amplification of target regions of pilC.

The practice of the present invention will employ, unless otherwise indicated, conventional techniques of molecular biology, microbiology, recombinant DNA, and immunology, which are within the skill of the art. Such techniques are explained fully in the literature. See e.g., Maniatis, Fitsch & Sambrook, MOLECULAR CLONING; A LABORATORY MANUAL, Second Edition (1989); DNA CLONING, VOLUMES I AND II (D. N Glover ed. 1985); OLIGONUCLEOTIDE SYNTHESIS (M. J. Gait ed, 1984); NUCLEIC ACID HYBRIDIZATION (B. D. Hames & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS IN ENZYMOLOGY (Academic Press, Inc.); GENE TRANSFER VECTORS FOR MAMMALIAN CELLS (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker, eds. (1987), IMMUNOCHEMICAL METHODS IN CELL AND MOLECULAR BIOLOGY (Academic Press, London), Scopes, (1987), PROTEIN PURIFICATION: PRINCIPLES AND PRACTICE, Second Edition (Springer-Verlag, N.Y.), and HANDBOOK OF EXPERIMENTAL IMMUNOLOGY, VOLUMES I–IV (D. M. Weir and C. C. Blackwell eds 1986). All patents, patent applications, and publications mentioned herein, both supra and infra, are hereby incorporated herein by reference.

As used herein, a polynucleotide "derived from" a designated sequence refers to a polynucleotide sequence which is comprised of a sequence of approximately at least about 6 nucleotides, preferably at least about 8 nucleotides, more preferably at least about 10–12 nucleotides, and even more preferably at least about 15–20 nucleotides corresponding to a region of the designated nucleotide sequence. "Corresponding" means homologous to or complementary to the designated sequence. Regions from which typical polynucleotide sequences may be "derived" include but are not limited to, for example, regions encoding specific epitopes, as well as non-transcribed and/or non-translated regions.

The derived polynucleotide is not necessarily physically derived from the nucleotide sequence shown, but may be generated in any manner, including for example, chemical synthesis or DNA replication or reverse transcription or transcription. In addition, combinations of regions corresponding to that of the designated sequence may be modified in ways known in the art to be consistent with an intended use.

Similarly, a polypeptide or amino acid sequence "derived from" a designated nucleic acid sequence refers to a polypeptide having an amino acid sequence identical to that of a polypeptide encoded in the sequence, or a portion thereof wherein the portion consists of at least 3–5 amino acids, and more preferably at least 8–10 amino acids, and even more preferably at least 11–15 amino acids, or which is immunologically identifiable with a polypeptide encoded in the sequence. This terminology also includes a polypeptide expressed from a designated nucleic acid sequence.

A recombinant or derived polypeptide is not necessarily translated from a designated nucleic acid sequence. It may be generated in any manner, including for example, chemical synthesis, or expression of a recombinant expression system, or isolation from a microorganism. A recombinant or derived polypeptide may include one or more analogs of amino acids or unnatural amino acids in its sequence. Methods of inserting analogs of amino acids into a sequence are known in the art. It also may include one or more labels, which are known to those of skill in the art.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, (3) does not occur in nature, or (4) is not in the form of a library.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

The term "purified polynucleotide" refers to a polynucleotide which is essentially free, i.e., contains less than about 50%, preferably less than about 70%, and even more preferably less than about 90% of polypeptides with which the polynucleotide is naturally associated. Techniques for purifying polynucleotides from bacteria are known in the art, and include for example, disruption of the bacteria with a chaotropic agent, differential extraction and separation of the polynucleotide(s) and polypeptides by ion-exchange chromatography, affinity chromatography, and sedimentation according to density.

The term "purified polypeptide" refers to a polypeptide or fragment thereof which is essentially free, i.e., contains less than about 50%, preferably less than about 70%, and even more preferably less than about 90%, of cellular components with which the polypeptide is naturally associated. Techniques for purifying polypeptides are known in the art, and examples of these techniques are discussed infra.

"Recombinant host cells", "host cells", "cells", "cell lines", "cell cultures", and other such terms denoting microorganisms or higher eukaryotic cell lines cultured as unicellular entities refer to cells which can be, or have been, used as recipients for recombinant vector or other transfer DNA, and include the progeny of the original cell which has been transfected. It is understood that the progeny of a single parental cell may not necessarily be completely identical in morphology or in genomic or total DNA complement as the original parent, due to natural, accidental, or deliberate mutation.

A "replicon" is any genetic element, e.g., a plasmid, a chromosome, a virus, a cosmid, etc. that behaves as an autonomous unit of polynucleotide replication within a cell; i.e., capable of replication under its own control.

A "vector" is a replicon in which another polynucleotide segment is attached, so as to bring about the replication and/or expression of the attached segment.

"Control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers. The term "control sequences" is intended to include, at a minimum, all components whose presence is necessary for expression, and may also include additional components whose presence is advantageous, for example, leader sequences.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide; this region may represent a portion of a coding sequence or a total coding sequence.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, and recombinant polynucleotide sequences.

"Immunologically identifiable with/as" refers to the presence of epitope(s) and polypeptides(s) which are also present in the designated polypeptide(s). Immunological identity may be determined by antibody binding and/or competition in binding; these techniques are known to those of average skill in the art, and are also illustrated infra.

As used herein, "epitope" refers to an antigenic determinant of a polypeptide. An epitope could comprise 3 amino acids in a spatial conformation which is unique to the epitope. Generally an epitope consists of at least 5 such amino acids, and more usually, consists of at least 8–10 such amino acids. Methods of determining the spatial conformation of amino acids are known in the art, and include, for example, x-ray crystallography and 2-dimensional nuclear magnetic resonance.

A polypeptide is "immunoreactive" when it is "immunologically reactive" with an antibody, i.e., when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The techniques for determining whether a polypeptide is immunologically reactive with an antibody are known in the art. An "immunoreactive" polypeptide may also be "immunogenic". As used herein, the term "immunogenic polypeptide" is a polypeptide that elicits a cellular and/or humoral immune response, whether alone or linked to a carrier in the presence or absence of an adjuvant.

As used herein, the term "antibody" refers to a polypeptide or group of polypeptides which are comprised of at least one antibody combining site. An "antibody combining site" or "binding domain" is formed from the folding of variable domains of an antibody molecule(s) to form three-dimensional binding spaces with an internal surface shape and charge distribution complementary to the features of an epitope of an antigen, which allows an immunological reaction with the antigen. An antibody combining site may be formed from a heavy and/or a light chain domain (VH and VL, respectively), which form hypervariable loops which contribute to antigen binding. The term "antibody" includes, for example, vertebrate antibodies, hybrid antibodies, chimeric antibodies, altered antibodies, univalent antibodies, the Fab proteins, and single domain antibodies.

As used herein, a "single domain antibody" (dAb) is an antibody which is comprised of an VH domain, which reacts immunologically with a designated antigen. A dAB does not contain a VL domain, but may contain other antigen binding domains known to exist in antibodies, for example, the kappa and lambda domains. Methods for preparing dABs are known in the art. See, for example, Ward et al. (1989).

Antibodies may also be comprised of VH and VL domains, as well as other known antigen binding domains. Examples of these types of antibodies and methods for their preparation are known in the art (see, e.g., U.S. Pat. No. 4,816,467, which is incorporated herein by reference), and include the following. For example, "vertebrate antibodies" refers to antibodies which are tetramers or aggregates thereof, comprising light and heavy chains which are usually aggregated in a "Y" configuration and which may or may not have covalent linkages between the chains. In vertebrate antibodies, the amino acid sequences of all the chains of a particular antibody are homologous with the chains found in one antibody produced by the lymphocyte which produces that antibody in situ, or in vitro (for example, in hybridomas). Vertebrate antibodies typically include native antibodies, for example, purified polyclonal antibodies and monoclonal antibodies. Examples of the methods for the preparation of these antibodies are described infra.

"Hybrid antibodies" are antibodies wherein one pair of heavy and light chains is homologous to those in a first antibody, while the other pair of heavy and light chains is homologous to those in a different second antibody. Typically, each of these two pairs will bind different epitopes, particularly on different antigens. This results in the property of "divalence", i.e., the ability to bind two antigens simultaneously. Such hybrids may also be formed using chimeric chains, as set forth below.

"Chimeric antibodies", are antibodies in which the heavy and/or light chains are fusion proteins. Typically the constant domain of the chains is from one particular species and/or class, and the variable domains are from a different species and/or class. Also included is any antibody in which either or both of the heavy or light chains are composed of combinations of sequences mimicking the sequences in antibodies of different sources, whether these sources be differing classes, or different species of origin, and whether or not the fusion point is at the variable/constant boundary. Thus, it is possible to produce antibodies in which neither the constant nor the variable region mimic known antibody sequences. It then becomes possible, for example, to construct antibodies whose variable region has a higher specific affinity for a particular antigen, or whose constant region can elicit enhanced complement fixation, or to make other improvements in properties possessed by a particular constant region.

Another example is "altered antibodies", which refers to antibodies in which the naturally occurring amino acid sequence in a vertebrate antibody has been varied. Utilizing recombinant DNA techniques, antibodies can be redesigned to obtain desired characteristics. The possible variations are many, and range from the changing of one or more amino acids to the complete redesign of a region, for example, the constant region. Changes in the constant region, in general, to attain desired cellular process characteristics, e.g., changes in complement fixation, interaction with membranes, and other effector functions. Changes in the variable region may be made to alter antigen binding characteristics. The antibody may also be engineered to aid the specific delivery of a molecule or substance to a specific cell or tissue site. The desired alterations may be made by known techniques in molecular biology, e.g., recombinant techniques, site directed mutagenesis, etc.

Yet another example are "univalent antibodies", which are aggregates comprised of a heavy chain/light chain dimer bound to the Fc (i.e., constant) region of a second heavy chain. This type of antibody escapes antigenic modulation. See, e.g., Glennie et al. (1982).

Included also within the definition of antibodies are "Fab" fragments of antibodies. The "Fab" region refers to those portions of the heavy and light chains which are roughly equivalent, or analogous, to the sequences which comprise the branch portion of the heavy and light chains, and which have been shown to exhibit immunological binding to a specified antigen, but which lack the effector Fc portion. "Fab" includes aggregates of one heavy and one light chain (commonly known as Fab'), as well as tetramers containing the 2H and 2L chains (referred to as $F(ab)_2$), which are capable of selectively reacting with a designated antigen or antigen family. "Fab" antibodies may be divided into subsets analogous to those described above, i.e., "vertebrate Fab", "hybrid Fab", "chimeric Fab", and "altered Fab". Methods of producing "Fab" fragments of antibodies are known within the art and include, for example, proteolysis, and synthesis by recombinant techniques.

The term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host genome.

"Treatment" as used herein refers to prophylaxis and/or therapy.

By "immunogenic" is meant an agent used to stimulate the immune system of a living organism, so that one or more functions of the immune system are increased and directed towards the immunogenic agent. Immunogenic agents include vaccines. Immunogenic agents can be used in the production of antibodies, both isolated polyclonal antibodies and monoclonal antibodies, using techniques known in the art.

By vaccine is meant an agent used to stimulate the immune system of a living organism so that protection against or amelioration of future harm is provided. Immunization refers to the process of inducing an increased level of antibodies and/or cellular immune response in which T-lymphocytes respond by killing the pathogen and/or activate other cells involved in the immune response pathway. The antibodies produced as a result of immunization may belong to any of the immunological classes, such as immunoglobulins A, D, E, G or M.

An "individual", as used herein, refers to vertebrates, particularly members of the mammalian species, and includes but is not limited to domestic animals, sports animals, and primates, including humans.

As used herein, the "sense strand" of a nucleic acid contains the sequence that has sequence homology to that of mRNA. The "anti-sense strand" contains a sequence which is complementary to that of the "sense strand".

As used herein, the term "probe" refers to a polynucleotide which forms a hybrid structure with a sequence in a target region, due to complementarity of at least one sequence in the probe with a sequence in the target region. The polynucleotide regions of probes may be composed of DNA, and/or RNA, and/or synthetic nucleotide analogs.

As used herein, the term "target region" refers to a region of the nucleic acid which is to be amplified and/or detected. The term "target sequence refers to a sequence with which a probe or primer will form a stable hybrid under desired conditions.

The term "primer" as used herein refers to an oligomer which is capable of acting as a point of initiation of synthesis of a polynucleotide strand when placed under appropriate conditions. The primer will be completely or substantially complementary to a region of the polynucleotide strand to be copied. Thus, under conditions conducive to hybridization, the primer will anneal to the complementary region of the analyte strand. Upon addition of suitable reactants, (e.g., a polymerase, nucleotide triphosphates, and the like), the primer is extended by the polymerizing agent to form a copy of the analyte strand. The primer may be single-stranded, or alternatively may be partially or fully double-stranded.

The terms "analyte polynucleotide" and "analyte strand" refer to a single- or double-stranded nucleic acid molecule which is suspected of containing a target sequence, and which may be present in a biological sample.

As used herein, a "biological sample" refers to a sample of tissue or fluid isolated from an individual, including but not limited to, for example, plasma, serum, spinal fluid, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components).

As used herein, the term "oligomer" refers to primers and to probes. The term oligomer does not connote the size of the molecule. However, typically oligomers are no greater than 1000 nucleotides, more typically are no greater than 500 nucleotides, even more typically are no greater than 250 nucleotides; they may be no greater than 100 nucleotides, and may be no greater than 75 nucleotides, and also may be no greater than 50 nucleotides in length.

The term "coupled" as used herein refers to attachment by covalent bonds or by strong non-covalent interactions (e.g., hydrophobic interactions, hydrogen bonds, etc.). Covalent bonds may be, for example, ester, ether, phosphoester, amide, peptide, imide, carbon-sulfur bonds, carbon-phosphorus bonds, and the like.

The term "support" refers to any solid or semi-solid surface to which a desired polypeptide or polynucleotide may be anchored. Suitable supports include glass, plastic, metal, polymer gels, and the like, and may take the form of beads, wells, dipsticks, membranes, and the like.

The term "label" as used herein refers to any atom or moiety which can be used to provide a detectable (preferably quantifiable) signal, and which can be attached to a polynucleotide or polypeptide.

The term "type 4 pilin" as used herein refer to pilins that contain a conserved amino terminal hydrophobic domain beginning with an amino-terminal phenylalanine that is methylated upon processing and secretion of the pilin. Another characteristic feature of type 4 pilins is that in the propilin form they contain similar six- or seven-amino acid long leader peptides, which are much shorter than typical signal sequences. Type 4 pilins are expressed by several bacterial genuses, including Neisseria, Moraxella, Bacteroides, and Pseudomonas. Species within these genuses which express type 4 pilins are, for example, *N. gonorrhoeae, N. meningitidis, M. bovis, B. nodosus*, and *P. aeruginosa*. As used herein, the term "type 4 pilin" also includes the Tcp pilin of Vibrio, (for example, V. cholerae), that is highly homologous to the type 4 pilins of other genuses. Tcp pilin contains the characteristic amino-terminal hydrophobic domain as well as having a modified N-terminal amino acid that in this case may be a modified methionine because the Tcp pilin gene encodes a methionine residue at the position where all the others encode a phenylalanine. Precursor TcpA contains a much longer leader sequence than typical type 4 propilins but retains homology in the region surrounding the processing site.

The term "pilC" as used herein refers to a gene encoding a polypeptide involved in the assembly of type 4 pilin, which may also be required for attachment of the pilin, and that is comprised of an epitope that is immunologically identifiable with an epitope in PilC of *N. gonorrhae* or *N. meningitidis*. Included within this term is any homologous region from Vibrio, tcpC.

As used herein the term "PilC" refers to a polypeptide encoded within pilC, and includes TcpC of Vibrio.

The description of the method to retrieve the DNA sequences is mostly of historical interest. The resultant sequences (and their complements) are provided herein, and the sequences, or any portion thereof, could be prepared using synthetic methods, or by a combination of synthetic methods with retrieval of partial sequences using methods similar to those described herein.

The description infra, of "walking" the genome by isolating overlapping DNA sequences from the *N. gonorrheae* lambda gt-11 library and from an EMBL3 library provides one method by which DNAs corresponding to the pilC genomes from, inter alia, *N. gonorrheae* and *N. meningitidis*, respectively, may be isolated. However, given the information provided herein, other methods for isolating pilC DNAs from these species, as well as from species of other genuses which have type 4 pilin are obvious to one of skill in the art.

Characterization of the genes of the pilC loci has provided information on the polypeptides encoded therein, and on the control of their expression. Even though Type 4 pili have been extensively studied in several laboratories, little is known about their assembly. The presence of a specific assembly machinery for this class of pili is evident from the fact that the pilin gene of *B. nodosus* and *M. bovis* can be properly processed and assembled into a pilus in *P. aeruginosa* but not in *E. coli* (Ellerman et al., 1986; Mattick et al., 1987; Beard et al., 1990). Furthermore, the recent genetic characterization of TCP pili of Vibrio cholerae has revealed that a number of closely linked genes are required for pilin processing and assembly into a structure (Taylor et al., 1988). The TCP pilin does not carry an N-methylphenylalanine but its primary sequence is highly homologous to the Type 4 class of pilins.

The *N. gonorrhoeae* pilus facilitates adherence of the bacterium to a number of eukaryotic cell types (Watt et al., 1980) and is thought to play a role in bacterial interaction with neutrophils (Fischer and Rest, 1988). The pilin is encoded from one or two pilE loci (Meyer et al., 1984; Swanson et al., 1986) which most likely each form a monocistronic operon. Hence, there have been no suggestions that genes closely linked to pilE are involved in pilus assembly. A dispersed location of genes involved in gonococcal pilus assembly as well as the rapid occurrence of nonpiliated variants generated via recombination with pilin sequences from silent loci, pilS, have made it extremely difficult to identify putative assembly genes for gonococcal pili.

The PilC protein described herein is a protein encoded within a pilC or equivalent (for example, tcpC) locus or gene. In *N. gonorrhoeae* MS11 and most other gonococcal strains the PilC protein is expressed in small amounts. It is the only protein that is enriched in highly purified preparations of MS11 pili. PilC was not released from a nonpilated MS11 (P$^-$n) variant using the same procedure suggesting that this protein interacts with the polymerized pilus fiber.

DNA sequence analysis of the cloned pilC1 gene revealed one long open reading frame that was out of frame with its putative AUG initiation codon and 5' end encoding the signal peptide. Minute amounts of PilC were expressed in *E. coli* from pABJ04. Gel purified PilC from MS11 contained a lysine residue in position four, whereas pilC1 had a glutamine codon at this position. A lysine codon was, however, found at position four in a number of PCR amplified 5' pilC fragments suggesting that these fragments represent the 5' end of pilC2, which then must be ON in MS11. The finding that a miniTnCm insertion in pilC2 abolished PilC expression, whereas insertional inactivation of pilC1 did not abolish PilC expression further argues that pilC1 is translationally out of frame and pilC2 translationally in frame in the MS11 variant we are studying.

PCR amplified fragments of pilC1 and pilC2 in MS11 differed in the number of G residues found in the G tract. Only 11 or 12 Gs were found in pilC1 clones (which would both generate an OFF phenotype) while 12 or 13 Gs were found among pilC2 specific clones. Since pilC2 is the expressed gene in the MS11 variant under study, we believe that this variant carries 13 Gs in pilC2 and 12 Gs in pilC1. The frequency of frameshift mutations in each locus is not known. However, the lack of 13 Gs among pilC1 specific fragments and the lack of 14 Gs among pilC2 specific fragments suggests that a deletion of one G residue occurs at a higher frequency than the insertion of one G residue. We had expected to find amplified fragments from *N. gonorrhoeae* containing 10 G residues in the G tract, but found none in the 48 clones sequenced. If only one G is added or deleted in each mutational event, the frequency of G tracts with 10 residues should be low if G tracts normally are 12 or 13 bp long.

Frameshifting in pilC1 also occurred in *E. coli*. In this case, however, two variants with 10 residues were found out of 12 clones sequenced. It may therefore be that there is a selection against in frame variants with 10 Gs in *N. gonor-* rhoeae. A change from five glycines to four in the signal peptide may for example have an effect on the physical properties of the precursor form of PilC such that the signal peptide is not cleaved off. *E. coli* strain AA10 is recA. Therefore, frameshift mutations in the G tract of pilC occurs independent of the RecA protein.

Translational frameshifting has been shown to regulate phase and antigenic variation of the gonococcal opacity protein PII that is encoded by a number of opa loci showing sequence variations. In this system a number of pentameric CTCTT repeats are present in the region encoding the signal peptide (Stern et al. 1986). Variation in the number of repeats is independent of recA in *N. gonorrhoeae* as well as in *E. coli* (Murphy et al., 1989). Variation in the expression of lipopolysaccharide epitopes in *Haemophilus influenzae* was recently explained by translational frameshifting created by alterations in the number of CAAT repeats occurring in the 5' end of licA (Weiser et al., 1989). In Bordetella pertussis frameshift mutations in the regulatory vir locus occur in a run of C residues positioned internally in the gene (Stibitz et al., 1989). The C tract was in this case varying from 6 (in frame) to 7 residues (out of frame). It is not known if this frameshift mutation is programed or not. The pilin gene of *Bordetella pertussis* was recently shown to be preceded by a stretch of Cs. Frequent mutations affecting the length of this C tract influenced the transcriptional activity of the pilin gene (Willems et al., 1990).

Variation in the number of the CTCTT repeats in opa genes was recently suggested to be due to recombination-independent slipped strand mispairing (Murphy et al., 1989). Mispairing is thought to occur between strands subjected to local denaturation and should preferentially occur during replication. A number of unusual DNA structures (cruciform, Z form, H form) have been shown to form in vitro within a variety of specific DNA sequences. Under normal conditions the B form is the most favorable thermodynamically (Frank-Kamenetskii and Vologodskii, 1984). Transition to alternative conformations requires specific external conditions, supercoiling being the most physiologic. Single stranded $(dG)_n$ and $(dC)_n$ strands renature more slowly than complementary strands with arbitrary sequences, and methylation experiments suggest that a poly dG chain may form a hairpin-like structure stabilized by G—G bp (Panyutin et al., 1990).

Four variant sequences differing outside the G tract were obtained by PCR amplification of the 5' end of pilC from four *N. gonorrhoeae* strains. The region 5' of the G tract was invariant, as was the 3' end of the amplified region. All variation was confined to a region located 3' of the G tract. At least some of these sequence variations can be explained by mismatch pairing events. Thus, the addition of four nucleotides distal to the G tract in variant sequence 4 is possible to explain by a two step mispairing event occurring within variant sequence 2. Slip strand mispairing between the two CA residues in -GGCGCAGGCGCA-(SEQ ID NO:36) would yield -GGCGCAGGCGCAGGCGCA-(SEQ ID NO:35). A second mispairing event occurring between the two C-residues at positions 3 and 5 gives rise to the sequence -GGCAGGCGCAGGCGCA-(SEQ ID NO:36) present in variant 4. It may therefore be that a sequence close to a poly(G) tract is prone to slipped strand mispairing.

Gonococcal pilus phase variation is associated with an altered nucleotide sequence of pilE via recombinations with silent pilS sequences (Haas and Meyer, 1986, Swanson et al., 1986). An irreversible switch OFF in pilus expression results from deletions of the 5' coding and control regions of the pilE locus (Swanson et al., 1985). Reversible gonococcal pilus phase variation is associated with nucleotide changes in pilE resulting in an altered pilin product. It has been suggested that the pilins of these variants are assembly defective (Bergstrom et al., 1986; Swanson et al., 1986; Hill et al., 1990). Here we present evidence that switch OFF and ON of PilC expression causes pilus expression to phase vary. Five out of five P⁻, pilin producing descendants from MS11$_{mk}$ (P⁺, PilC⁺) that expressed pilin did not express PilC. All tested P⁺ revertants from the five P⁻, PilC⁻ variants had regained expression of PilC. The pilin of one nonpiliated PilC OFF-switcher (variant 8) differed by eight amino acids from that of the parent. The fact that one piliated PilC⁺ backswitcher (8:1) expressed a pilin identical in sequence to the nonpiliated variant (8) strongly suggests that the regained expression of pili is due to an ON-switch in PilC expression. The above results also imply that the nonpiliated phenotype of variant 8 is not due to the alterations in the pilin relative to the parental strain but to an OFF-switch of PilC. The finding that mTnCm insertions resulted in P⁺ colonies when inserted into pilC1 and P⁻ colonies when inserted into the actively expressing pilC2 locus offers further evidence that PilC is essential for the biogenesis of gonococcal pili. P⁻, pilC2::mTnCm-12 insertion mutants reverted to P⁺ colony morphology at a low frequency. These revertants most likely represent frameshifting mutants in pilC1 resulting in expression of PilC from this locus. A double mutant in pilC1 and pilC2 was stably nonpiliated, expressed pilin, but expressed amounts of pilin that did not express any pili when examined by transmission electron microscopy. It is therefore believed that out of frame mutations of both pilC1 and pilC2 will abolish pili formation.

At this stage we cannot exclude the possibility that some PilC⁻ variants from MSII$_{mk}$(P⁺, PilC⁻) are generated by transformation of pilC1 sequences and homologous recombination with pilC2 thus generating variants with two pilC1 5' ends at both pilC loci. PilC⁺ revertants from PilC⁻ clones must, however, all be due to frameshift mutations in either pilC1 or pilC2.

We propose that PilC forms an outer membrane pore or assembly center enabling the pilin subunits to be assembled and translocated across the outer membrane analogous to the proposed function of the high molecular weight proteins required for the assembly of enterobacterial pili (the latter of which is discussed in Norgren et al., 1987). Alternatively, PilC may act as an initiator for polymerization. In the latter case PilC would be expected to be located at the tip of the polymerized pilus.

It is possible that the alternate expression of PilC from two structurally different pilC loci is yet another example of antigenic variation in *Neisseria gonorrhoeae*. It is, however, possible that this variation could have functional implications as well. Each class of *E. coli* pili utilizes a different outer membrane pore/assembly protein. Hence, pilin subunits and/or periplasmic chaperone complexes may specifically interact with an exposed region of the protein allowing polymerization of pilus subunit proteins. The repertoire of antigenic variants of gonococcal pilins is vast (Hagblom et al., 1985). It may be that only certain pilin variants are assembled via PilC1 and PilC2 respectively. Alternatively, if PilC acts as an initiator it could also possess other properties such as being involved in Pilus mediated attachment.

In one embodiment of the invention, immunogenically active polypeptides encoded within pilC are prepared. The availability of pilC DNA sequences, either those isolated by utilizing the DNA sequences described in the Examples, or nucleotide sequences derived therefrom (including segments and modifications of the sequence), permits the construction of expression vectors encoding immunologically reactive regions of the polypeptide encoded in either strand. Immunological reactivity may be determined by immunoassay using antibodies raised to PilC. Fragments encoding the desired polypeptides are derived from the DNA clones using conventional restriction digestion or by synthetic methods, and are ligated into vectors which may, for example, contain portions of fusion sequences such as beta-galactosidase or superoxide dismutase (SOD), preferably SOD. Methods and vectors which are useful for the production of polypeptides which contain fusion sequences of SOD are described in European Patent Office Publication number 0196056, published Oct. 1, 1986. Any desired portion of the pilC DNA containing an open reading frame, in either sense strand, can be obtained as a recombinant polypeptide, such as a mature or fusion protein; alternatively, a polypeptide encoded in the DNA can be provided by chemical synthesis.

The DNA encoding the desired polypeptide, whether in fused or mature form, and whether or not containing a signal sequence to permit secretion, may be ligated into expression vectors suitable for any convenient host. Both eukaryotic and prokaryotic host systems are presently used in forming recombinant polypeptides, and a summary of some of the more common control systems and host cell lines is given infra. The polypeptide is then isolated from lysed cells or from the culture medium and purified to the extent needed for its intended use. Purification may be by techniques known in the art, for example, differential extraction, salt fractionation, chromatography on ion exchange resins, affinity chromatography, centrifugation, and the like. See, for example, Methods in Enzymology for a variety of methods for purifying proteins. Such polypeptides can be used as diagnostics, or those which give rise to neutralizing antibodies may be formulated into vaccines. Antibodies raised against these polypeptides can also be used as diagnostics, or for passive immunotherapy.

The PilC antigens may also be isolated from meningococci and from gonococci. The bacteria may be grown by conditions known in the art, some of which are described infra. In addition, a method for isolating PilC from gonococci is described infra.

In another embodiment of the invention, the immunoreactive polypeptides may be conjugated with carrier. An antigenic region of a polypeptide is generally relatively small—typically 8 to 10 amino acids or less in length. Fragments of as few as 5 amino acids may characterize an antigenic region. These segments may correspond to regions of PilC antigen. Accordingly, using the DNAs of pilC as a basis, DNAs encoding short segments of PilC polypeptides can be expressed recombinantly either as fusion proteins, or as isolated polypeptides. In addition, short amino acid sequences can be conveniently obtained by chemical synthesis. In instances wherein the synthesized polypeptide is correctly configured so as to provide the correct epitope, but is too small to be immunogenic, the polypeptide may be linked to a suitable carrier.

A number of techniques for obtaining such linkage are known in the art, including the formation of disulfide linkages using N-succinimidyl-3-(2-pyridyl-thio)propionate (SPDP) and succinimidyl 4-(N-maleimido-methyl) cyclohexane-1-carboxylate (SMCC) obtained from Pierce Company, Rockford, Ill., (if the peptide lacks a sulfhydryl group, this can be provided by addition of a cysteine residue.) These reagents create a disulfide linkage between themselves and peptide cysteine residues on one protein and an amide linkage through the epsilon-amino on a lysine, or other free amino group in the other. A variety of such disulfide/amide-forming agents are known. See, for example, Immun. Rev. (1982) 62:185. Other bifunctional coupling agents form a thioether rather than a disulfide linkage. Many of these thio-ether-forming agents are commercially available and include reactive esters of 6-maleimidocaproic acid, 2-bromoacetic acid, 2-iodoacetic acid, 4-(N-maleimido-methyl)cyclohexane-1-carboxylic acid, and the like. The carboxyl groups can be activated by combining them with succinimide or 1-hydroxyl-2-nitro-4-sulfonic acid, sodium salt. Additional methods of coupling antigens employs the rotavirus/"binding peptide" system described in EPO Pub. No. 259,149, the disclosure of which is incorporated herein by reference. The foregoing list is not meant to be exhaustive, and modifications of the named compounds can clearly be used.

Any carrier may be used which does not itself induce the production of antibodies harmful to the host. Suitable carriers are typically large, slowly metabolized macromolecules such as proteins; polysaccharides, such as latex functionalized sepharose, agarose, cellulose, cellulose beads and the like; polymeric amino acids, such as polyglutamic acid, polylysine, and the like; amino acid copolymers; and inactive virus particles or attenuated bacteria of other strains, for example, those of Salmonella. Especially useful protein substrates are serum albumins, keyhole limpet hemocyanin, immunoglobulin molecules, thyroglobulin, ovalbumin, tetanus toxoid, and other proteins well known to those skilled in the art.

In addition to full-length PilC proteins, polypeptides comprising truncated PilC amino acid sequences encoding at least one immunologically reactive epitope are useful immunological reagents. For example, polypeptides comprising such truncated sequences can be used as reagents in an immunoassay. These polypeptides also are candidate subunit antigens in compositions for antiserum production or vaccines. While these truncated sequences can be produced by various known treatments of native bacterial protein, it is generally preferred to make synthetic or recombinant polypeptides comprising a PilC sequence. Polypeptides comprising these truncated PilC sequences can be made up entirely of PilC sequences (one or more epitopes, either contiguous or noncontiguous), or PilC sequences and heterologous sequences in a fusion protein. Useful heterologous sequences include sequences that provide for secretion from a recombinant host, enhance the immunological reactivity of the PilC epitope(s), or facilitate the coupling of the polypeptide to an immunoassay support or a vaccine carrier. See, e.g., EPO Pub. No. 116,201; U.S. Pat. No. 4,722,840; EPO Pub. No. 259,149; U.S. Pat. No. 4,629,783, the disclosures of which are incorporated herein by reference.

The size of polypeptides comprising the truncated PilC sequences can vary widely, the minimum size being a sequence of sufficient size to provide an immunologically reactive PilC epitope, while the maximum size is not critical. For convenience, the maximum size usually is not substantially greater than that required to provide the desired PilC epitopes and function(s) of the heterologous sequence, if any. Typically, the truncated PilC amino acid sequence will range from about 5 to about 100 amino acids in length. More typically, however, the PilC sequence will be a maximum of about 50 amino acids in length, preferably a maximum of about 30 amino acids. It is usually desirable to select PilC sequences of at least about 10, 12 or 15 amino acids, up to a maximum of about 20 or 25 amino acids.

Truncated PilC amino acid sequences comprising epitopes can be identified in a number of ways. For example, the entire PilC protein sequence can be screened by preparing a series of short peptides that together span the entire protein sequence. By starting with, for example, 100mer polypeptides, it would be routine to test each polypeptide for the presence of epitope(s) showing a desired reactivity, and then testing progressively smaller and overlapping fragments from an identified 100mer to map the epitope of interest. Screening such peptides in an immunoassay is within the skill of the art. It is also known to carry out a computer analysis of a protein sequence to identify potential epitopes, and then prepare oligopeptides comprising the identified regions for screening.

In another embodiment of the invention, the immunogenicity of the epitopes of PilC may also be enhanced by preparing them in mammalian or yeast systems fused with or assembled with particle-forming proteins such as, for example, that associated with hepatitis B surface antigen. See, e.g., U.S. Pat. No. 4,722,840. Constructs wherein the PilC epitope is linked directly to the particle-forming protein coding sequences produce hybrids which are immunogenic with respect to the PilC epitope. In addition, all of the vectors prepared include epitopes specific to HBV, having various degrees of immunogenicity, such as, for example, the pre-S peptide. Thus, particles constructed from particle forming protein which include PilC sequences are immunogenic with respect to the microorganism encoding the PilC epitope (for example, Neisseria, Vibrio, Moraxella, Bacteroides, or Pseudomonas) and HBV.

Hepatitis surface antigen (HBSAg) has been shown to be formed and assembled into particles in S. cerevisiae (Valenzuela et al. (1982)), as well as in, for example, mammalian cells (Valenzuela, P., et al. (1984)). The formation of such particles has been shown to enhance the immunogenicity of the monomer subunit. The constructs may also include the immunodominant epitope of HBSAg, comprising the 55 amino acids of the presurface (pre-S) region. Neurath et al. (1984). Constructs of the pre-S-HBSAg particle expressible in yeast are disclosed in EPO 174,444, published Mar. 19, 1986; hybrids including heterologous viral sequences for yeast expression are disclosed in EPO 175,261, published Mar. 26, 1966. These constructs may also be expressed in mammalian cells such as Chinese hamster ovary (CHO) cells using an SV40-dihydrofolate reductase vector (Michelle et al. (1984)).

In addition, portions of the particle-forming protein coding sequence may be replaced with codons encoding a PilC epitope. In this replacement, regions which are not required to mediate the aggregation of the units to form immunogenic particles in yeast or mammals can be deleted, thus eliminating additional HBV antigenic sites from competition with the PilC epitope.

In another embodiment of the invention, the immunoreactive polypeptides encoded in pilC are prepared into vaccines. Vaccines may be prepared from one or more immunogenic polypeptides derived from pilC. If recombinant, these polypeptides may be expressed in various host cells (e.g., bacteria, yeast, insect, or mammalian cells), or alternatively may be isolated from the bacterial preparations. In addition to the above, it is also possible to prepare live vaccines of attenuated microorganisms which express one or more recombinant polypeptides derived from the pilC gene. Suitable attenuated microorganisms are known in the art and include, for example, viruses (e.g., vaccinia virus (see Brown et al. (1986)), as well as bacteria.

The preparation of vaccines which contain an immunogenic polypeptide(s) as active ingredients, is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosph oryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against an immunogenic polypeptide containing a PilC immunoreactive sequence resulting from administration of this polypeptide in vaccines which are also comprised of the various adjuvants.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1%–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%–95% of active ingredient, preferably 25%–70%.

The proteins may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be prophylactically and/or therapeutically effective. The quantity to be administered, which is generally in the range of 5 micrograms to 250 micrograms of antigen per dose, depends on the subject to be treated, capacity of the subject's immune system to synthesize antibodies, and the degree of protection desired. Precise amounts of active ingredient required to be administered may depend on the judgment of the practitioner and may be peculiar to each subject.

The vaccine may be given in a single dose schedule, or preferably in a multiple dose schedule. A multiple dose schedule is one in which a primary course of vaccination may be with 1–10 separate doses, followed by other doses given at subsequent time intervals required to maintain and or reenforce the immune response, for example, at 1–4 months for a second dose, and if needed, a subsequent dose(s) after several months. The dosage regimen will also, at least in part, be determined by the need of the individual and be dependent upon the judgment of the practitioner.

In addition, the vaccine containing the immunogenic antigen(s) derived from pilC may be administered in conjunction with other immunoregulatory agents, for example, immune globulins.

Another embodiment of the invention are antibodies which react immunologically with PilC epitopes. The immunogenic polypeptides prepared as described above are used to produce antibodies, including polyclonal and monoclonal. If polyclonal antibodies are desired, a selected mammal (e.g., mouse, rabbit, goat, horse, etc.) is immunized with an immunogenic polypeptide bearing a PilC epitope(s). Serum from the immunized animal is collected and treated according to known procedures. If serum containing polyclonal antibodies to a PilC epitope (i.e., an epitope encoded within pilC) contains antibodies to other antigens, the polyclonal antibodies can be purified by immunoaffinity chromatography. Techniques for producing and processing polyclonal antisera are known in the art, see for example, Mayer and Walker (1987).

Monoclonal antibodies directed against PilC epitopes can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al. (1980); Hammerling et al. (1981); Kennett et al. (1980); see also, U.S. Pat. Nos. 4,341,761; 4,399,121; 4,427,783; 4,444,887; 4,466,917; 4,472,500; 4,491,632; and 4,493,890. Panels of monoclonal antibodies produced against PilC epitopes can be screened for various properties; i.e., for isotype, epitope affinity, etc.

Antibodies, both monoclonal and polyclonal, which are directed against PilC epitopes are particularly useful in diagnosis, and those which are neutralizing are useful in passive immunotherapy. Methods for introducing antibodies into an individual to accomplish passive immunotherapy are known in the art. In addition, monoclonal antibodies, in particular, may be used to raise anti-idiotype antibodies.

Anti-idiotype antibodies are immunoglobulins which carry an "internal image" of the antigen of the infectious agent against which protection is desired. See, for example, Nisonoff, A., et al. (1981) and Dreesman et al. (1985). Techniques for raising anti-idiotype antibodies are known in the art. See, for example, Grzych (1985), MacNamara et al. (1984), and Uytdehaag et al. (1985). These anti-idiotype antibodies may also be useful for treatment, vaccination and/or diagnosis of the relevant microorganism encoding the antigen of interest, (for example, Neisseria, Pseudomonas, Moraxella, Bacteroides, or Vibrio) as well as for an elucidation of the immunogenic regions of PilC.

Another embodiment of the invention concerns immunoassays and diagnostic kits. The polypeptides which contain epitopes encoded in pilC which are immunoreactive with anti-PilC antibodies in biological samples are useful in immunoassays to detect presence of anti-PilC antibodies, or the presence of the relevant microorganism or its antigens in biological samples. Design of the immunoassays is subject to a great deal of variation, and many formats are known in the art. The immunoassay will utilize a polypeptide comprised of at least one epitope derived from PilC or encoded in pilC. In one embodiment, the immunoassay uses a combination of epitopes including the one derived from PilC or encoded in pilC. These epitopes may be derived from the same or from different polypeptides, and may be in separate recombinant or natural polypeptides, or together in the same recombinant polypeptides. An immunoassay may use, for example, a monoclonal antibody directed towards an epitope (s), a combination of monoclonal antibodies directed towards epitopes of one antigen, monoclonal antibodies directed towards epitopes of different antigens, polyclonal antibodies directed towards the same antigen, or polyclonal antibodies directed towards different antigens. Protocols may be based, for example, upon competition, or direct reaction, or sandwich type assays. Protocols may also, for example, use solid supports, or may be by immunoprecipitation. Most assays involve the use of labeled antibody or polypeptide; the labels may be, for example, enzymatic, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Typically, an immunoassay for an anti-PilC antibody(s) will involve selecting and preparing the test sample suspected of containing the antibodies, such as a biological sample, then incubating it with an immunoreactive (also called antigenic) polypeptide(s) containing at least one epitope encoded in pilC. The incubation is under conditions that allow antigen-antibody complexes to form. Suitable incubation conditions are well known in the art. Subsequent to the incubation, complexes which are formed which contain the immunoreactive polypeptide are detected. The immunoassay may be, without limitations, in a heterogenous or in a homogeneous format, and of a standard or competitive type.

In a heterogeneous format, the polypeptide is typically bound to a solid support to facilitate separation of the sample from the polypeptide after incubation. Examples of solid supports that can be used are nitro-cellulose (e.g., in membrane or microtiter well form), polyvinyl chloride (e.g., in sheets or microtiter wells), polystyrene latex (e.g., in beads or microtiter plates, polyvinylidine fluoride (known as Immulon), diazotized paper, nylon membranes, activated beads, and Protein A beads. For example, Dynatech Immulon[1] or Immulon[2] microtiter plates or 0.25 inch polystyrene beads (Precision Plastic Ball) can be used in the heterogeneous format. The solid support containing the antigenic polypeptide is typically washed after separating it from the test sample, and prior to detection of bound antibodies. Both standard and competitive formats are known in the art.

In a homogeneous format, the test sample is incubated with antigen in solution. For example, it may be under conditions that will precipitate any antigen-antibody complexes which are formed. Both standard and competitive formats for these assays are known in the art.

In a standard format, the amount of anti-PilC antibodies forming the antibody-antigen complex is directly monitored. This may be accomplished by determining whether labeled anti-xenogeneic (e.g., anti-human) antibodies which recognize an epitope on anti-PilC antibodies will bind due to complex formation. In a competitive format, the amount of anti-PilC antibodies in the sample is deduced by monitoring the competitive effect on the binding of a known amount of labeled antibody (or other competing ligand) in the complex.

Complexes formed comprising anti-PilC antibody (or, in the case of competitive assays, the amount of competing antibody) are detected by any of a number of known techniques, depending on the format. For example, unlabeled anti-PilC antibodies in the complex may be detected using a conjugate of antixenogeneic Ig complexed with a label, (e.g., an enzyme label).

In immunoassays where PilC polypeptides are the analyte, the test sample, which may be a biological sample, is incubated with anti-PilC antibodies under conditions that allow the formation of antigen-antibody complexes. Various formats can be employed. For example, a "sandwich assay" may be employed, where antibody bound to a solid support is incubated with the test sample; washed; incubated with a second, labeled antibody to the analyte, and the support is washed again. Analyte is detected by determining if the second antibody is bound to the support. In a competitive format, which can be either heterogeneous or homogeneous, a test sample is usually incubated with antibody and a labeled, competing antigen is also incubated, either sequentially or simultaneously. These and other formats are well known in the art.

The antigenic regions of the polypeptides encoded in pilC can be mapped and identified by screening the antigenicity of expression products of pilC DNAs which encode portions of the PilC. The expression products may be from a variety of expression systems, including, for example bacterial systems, yeast systems, insect systems, and eukaryotic cell systems. In addition, studies giving rise to an antigenicity index and hydrophobicity/hydrophilicity profile give rise to information concerning the probability of a region's antigenicity.

Efficient detection systems for infection with pathogenic microorganisms, (for example, Neisseria, Pseudomonas, Bacteroides, Moraxella, or Vibrio) may include the use of panels of epitopes. The epitopes in the panel may be constructed into one or multiple polypeptides. At least one of the epitopes will be encoded in pilC or derived from PilC. The assays for the varying epitopes may be sequential or simultaneous.

Kits suitable for immunodiagnosis and containing the appropriate labeled reagents are constructed by packaging the appropriate materials, including the polypeptides of the invention containing PilC epitopes (i.e., epitopes encoded within pilC) or antibodies directed against PilC epitopes in suitable containers. The kit may also contain other reagents, for example, buffer and standard, as well as other materials required for the conduct of the assay, as well as a suitable set of instructions for conducting the assay using the kit materials.

Another embodiment of the invention are oligomers. Using the disclosed portions of the pilC DNAs as a basis, oligomers of approximately 8 nucleotides or more can be prepared, either by excision from recombinant polynucleotides or by synthetic methods which are known in the art. These oligomers can serve as probes for the detection (including isolation and/or labeling) of polynucleotides which contain pilC sequences, and/or as primers for the transcription and/or replication of targeted pilC sequences. The oligomers contain a targeting polynucleotide sequence, which is comprised of nucleotides which are complementary to a target pilC nucleotide sequence; the sequence is of sufficient length and complementarity with the pilC sequence to form a duplex which has sufficient stability for the purpose intended. For example, if the purpose is the isolation, via immobilization, of an analyte containing a target pilC sequence, the oligomers would contain a polynucleotide region which is of sufficient length and complementarity to the targeted pilC sequence to afford sufficient duplex stability to immobilize the analyte on a solid surface, via its binding to the oligomers, under the isolation conditions. For example, also, if the oligomers are to serve as primers for the transcription and/or replication of target pilC sequences in an analyte polynucleotide, the oligomers would contain a polynucleotide region of sufficient length and complementarity to a region flanking the targeted pilC sequence to allow the polymerizing agent to continue replication from the primers which are in stable duplex form with the target sequence, under the polymerizing conditions. The oligomers may contain a minimum of about 4 contiguous nucleotides which are complementary to a targeted pilC sequence; usually the oligomers will contain a minimum of about 8 contiguous nucleotides which are complementary to the targeted pilC sequence, and preferably will contain a minimum of about 14 contiguous nucleotides which are complementary to the targeted pilC sequence.

The oligomer, however, need not consist only of the sequence which is complementary to the targeted pilC sequence. It may contain in addition, nucleotide sequences or other moieties which are suitable for the purposes for which the oligomers are used. For example, if the oligomers are used as primers for the amplification of targeted pilC sequences via the polymerase chain reaction (PCR), they may contain sequences which, when in duplex, form restriction enzyme sites which facilitate the cloning of the amplified sequences. Other types of moieties or sequences which are useful of which the oligomers may be comprised or coupled to, are those which are known in the art to be suitable for a variety of purposes, including the labeling of nucleotide probes.

In the basic nucleic acid hybridization assay, single-stranded analyte nucleic acid (either DNA or RNA) is hybridized to a nucleic acid probe, and resulting duplexes are detected. The probes for pilC sequences (natural or derived) are a length which allows the detection of these sequences by hybridization. While 6–8 nucleotides may be a workable length, sequences of 10–12 nucleotides are preferred, and about 20 nucleotides or more appears optimal. Preferably, these sequences will derive from regions which lack heterogeneity. These probes can be prepared using routine methods, including automated oligonucleotide synthetic methods. For use as probes, complete complementarity is desirable, although it may be unnecessary as the length of the fragment is increased.

For use of such probes as agents to detect the presence of pilC sequences, the sample to be analyzed (which may be biological) may be treated, if desired, to extract the nucleic acids contained therein. The resulting nucleic acid from the sample may be subjected to gel electrophoresis or other size separation techniques; alternatively, the nucleic acid sample may be dot blotted without size separation. In order to form hybrid duplexes with the targeting sequence of the probe, the targeted region of the analyte nucleic acid must be in single-stranded form. The latter may occur naturally; alternatively, it may be accomplished by denaturation. Denaturation can be accomplished by various techniques known in the art. Subsequent to denaturation, the analyte nucleic acid and probe are incubated under conditions which promote stable hybrid formation of the target sequence in the probe with the putative targeted sequence in the analyte, and the resulting duplexes containing probe(s) are detected.

Detection of the resulting duplex, if any, is usually accomplished by the use of labeled probes; alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation or kinasing), biotin, fluorescent groups, chemiluminescent groups (e.g., doxetanes, particularly triggered dioxetands), enzymes, antibodies, and the like. Variations of this basic scheme are known in the art.

If the targeted pilC sequences are expected to be present at relatively low levels, amplification may be required for their detection. Such techniques are known in the art. For example, the Enzo Biochemical Corporation "Bio-Bridge" system uses terminal deoxynucleotide transferase to add unmodified 3'-poly-dT-tails to a DNA probe. The poly dT-tailed probe is hybridized to the target nucleotide sequence, and then to a biotin-modified poly-A. PCT application 84/03520 and EPA124221 describe a DNA hybridization assay in which: (1) analyte is annealed to a single-stranded DNA probe that is complementary to an enzyme-labeled oligonucleotide; and (2) the resulting tailed duplex is hybridized to an enzyme-labeled oligonucleotide. EPA 204510 describes a DNA hybridization assay in which analyte DNA is contacted with a probe that has a tail, such as a poly-dT tail, an amplifier strand that has a sequence that hybridizes to the tail of the probe, such as a poly-A sequence, and which is capable of binding a plurality of labeled strands. A particularly desirable technique may first involve amplification of the target pilC sequences. The target pilC sequences in sera may be amplified, for example, to approximately $10^6$ sequences/ml. This may be accomplished, for example, by the polymerase chain reactions (PCR) technique described by Saiki et al. (1986), by Mullis, U.S. Patent No. 4,683,195, and by Mullis et al. U.S. Pat. No. 4,683,202. Amplification may be prior to, or preferably subsequent to purification of the pilC target sequence. For example, amplification may be utilized in conjunction with the assay methods described in U.S. Pat. No. 4,868,105, or if even further amplification is desired, in conjunction with the hybridization system in EPO Publication No. 317,077.

Generally, in the PCR technique, short oligonucleotide primers are prepared which match opposite ends of a desired sequence. The sequence between the primers need not be known. A sample of polynucleotide is extracted and denatured, preferably by heat, and hybridized with oligomers which are oligonucleotide primers, which are present in molar excess. Polymerization is catalyzed by a template- and primer-dependent polymerase in the presence of deoxynucleotide triphosphates (dNTPs), and may also be in the presence of nucleotide analogs. This results in two "long products" which contain the respective primers at their 5'-termini, covalently linked to the newly synthesized complements of the original strands. The replicated DNA is again denatured, hybridized with oligonucleotide primers, returned to polymerizing conditions, and a second cycle of replication is initiated. The second cycle provides the two original strands, the two long products from cycle 1, and two "short products" replicated from the long products. The short products contain sequences (sense or antisense) derived from the target sequence, flanked at the 5'- and 3'-termini with primer sequences. On each additional cycle, the number of short products is replicated exponentially. Thus, this process causes amplification of a specific target sequence.

It will be understood that "primer", as used herein, may refer to more than one primer, particularly in the case where there is some ambiguity in the information regarding the terminal sequence(s) of the target region to be amplified. Hence, a "primer" includes a collection of primer oligonucleotides containing sequences representing the possible variations in the sequence or includes nucleotides which allow a typical base pairing. One of the primer oligomers in this collection will be homologous with the end of the target sequence.

The amplified sequence(s) may then be detected using a hybridization assay which utilize nucleic acid multimers which bind to single-stranded analyte nucleic acid, and which also bind to a multiplicity of single-stranded labeled oligonucleotides. A suitable solution phase sandwich assay which may be used with labeled polynucleotide probes, and the methods for the preparation of probes is described in EPO 225,807, published Jun. 16, 1987.

The probes can be packaged into diagnostic kits. Diagnostic kits include the probe DNA, which may be labeled; alternatively, the probe DNA may be unlabeled and the ingredients for labeling may be included in the kit in separate containers. The kit may also contain other suitably packaged reagents and materials needed for the particular hybridization protocol, for example, standards, buffers, as well as instructions for conducting the test using the kit ingredients.

The pilC DNA sequence information in the clones described in the Examples may be used to gain further information on the remaining sequence of the pilC gene from meningococci, for other possible alleles of pilC in Neisseria, as well as pilC in other relevant genuses and species. This information will aid in the characterization of the gene, and of its role in virulence of the pathogenic forms of microorganisms, including, for example, Neisseria, Pseudomonas, Bacteroides, Moraxella, and Vibrio. Moreover, this sequence information can lead to additional polynucleotide probes, polypeptides derived from pilC, multiple pilC loci, and antibodies directed against PilC epitopes which would be useful for the diagnosis and/or treatment of infections caused by the relevant pathogenic microorganisms.

The DNA sequence information in the above-mentioned clones is useful for the design of probes for the isolation of additional DNA sequences which are derived from as yet undefined regions of pilC. For example, labeled probes containing a sequence of approximately 8 or more nucleotides, and preferably 20 or more nucleotides, which are derived from regions close to the ends of the DNA sequences shown in the Examples. These probes may be used to isolate overlapping DNA sequences within or adjacent to pilC from DNA libraries created from genomes of species having type 4 pilins. The resulting overlapping DNAs may then be used to synthesize probes for identification of other overlapping fragments which do not necessarily overlap the DNAs whose sequences are given in the Examples. Thus, it is possible to sequence entire pilC genes utilizing the DNA sequences provided herein and the technique of isolation of overlapping DNAs derived from the pilC genes.

Methods for constructing DNA libraries are known in the art, and are discussed infra; for example, a method for the construction of pilC libraries in lambda-gt11 is discussed infra in Section IV.A. However, DNA libraries which are useful for screening with nucleic acid probes may also be constructed in other vectors known in the art, for example, lambda-gt10 (Huynh et al. (1985)). Another suitable vector for the creation of libraries may be EMBL3, which is a replacement vector which accepts inserts ranging from 9 to 23 kb in size. In general, methods for constructing DNA libraries is discussed in Maniatis et al, MOLECULAR CLONING, 2nd edition, (1989).

The sequence information derived from these overlapping pilC DNAs is useful for determining areas of homology and heterogeneity within the pilC gene(s), which could indicate the presence of different strains gonococci, meningococci, or other hitherto unrecognized pathogenic forms of Neisseria. It is also useful for the design of hybridization probes to detect PilC antigens or pilC nucleic acids in biological samples. Moreover, the overlapping DNAs may be used to create expression vectors for polypeptides derived from pilC gene(s).

The pilC DNA sequence information may also allow the construction of additional bacteriostatic agents for treatment of neisserial infections, in that they may block the expression of PilC and/or pilin assembly. For example, it may be used to derive antisense polynucleotides. Antisense polynucleotides molecules are comprised of a complementary nucleotide sequence which allows them to hybridize specifically to designated regions of genomes or RNAs. Antisense polynucleotides may include, for example, molecules that will block protein translation by binding to mRNA, or may be molecules which prevent replication of DNA by replicase. They may also include molecules which carry agents (non-covalently attached or covalently bound) which cause the mRNA or genomic DNA to be inactive by causing, for example, scissions in these molecules. Antisense molecules which are to hybridize to pilC derived polynucleotides may be designed based upon the sequence information of the pilC DNA sequences provided herein, including those which would be isolated from additional DNA libraries. The antibacterial agents based upon anti-sense polynucleotides for pilC may be designed to bind with high specificity, to be of increased solubility, to be stable, and to have low toxicity. Hence, they may be delivered in specialized systems, for example, liposomes, or by gene therapy. In addition, they may include analogs, attached proteins, substituted or altered bonding between bases, etc.

Other types of drugs may be based upon polynucleotides which "mimic" important control regions of the pilC gene, and which may be therapeutic due to their interactions with key components of the system responsible for expression of the gene.

In addition to the specific methods described in the Examples, general methods are known which may be used in the practice of the invention. For example, general techniques used in extracting the genome from bacteria, including Neisseria, preparing and probing a DNA library, sequencing clones, constructing expression vectors, transforming cells, performing immunological assays such as radioimmunoassays and ELISA assays, for growing cells in culture, and the like are known in the art and laboratory manuals are available describing these techniques. However, as a general guide, the following sets forth some sources currently available for such procedures, and for materials useful in carrying them out.

Both prokaryotic and eukaryotic host cells may be used for expression of desired coding sequences when appropriate control sequences which are compatible with the designated host are used. Among prokaryotic hosts, *E. coli* is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These markers may be used to obtain successful transformants by selection. Commonly used prokaryotic control sequences include the Beta-lactamase (penicillinase) and lactose promoter systems (Chang et al. (1977)), the tryptophan (trp) promoter system (Goeddel et al. (1980)) and the lambda-derived $P_L$ promoter and N gene ribosome binding site (Shimatake et al. (1981)) and the hybrid tac promoter (De Boer et al. (1983)) derived from sequences of the trp and lac UV5 promoters. The foregoing systems are particularly compatible with *E. coli*; if desired, other prokaryotic hosts such as strains of Bacillus or Pseudomonas may be used, with corresponding control sequences.

Eukaryotic hosts include yeast and mammalian cells in culture systems. *Saccharomyces cerevisiae* and *Saccharomyces carlsbergensis* are the most commonly used yeast hosts, and are convenient fungal hosts. Yeast compatible vectors carry markers which permit selection of successful transformants by conferring prototrophy to auxotrophic mutants or resistance to heavy metals on wild-type strains. Yeast compatible vectors may employ the 2 micron origin of replication (Broach et al. (1983)), the combination of CEN3 and ARS1 or other means for assuring replication, such as sequences which will result in incorporation of an appropriate fragment into the host cell genome. Control sequences for yeast vectors are known in the art and include promoters for the synthesis of glycolytic enzymes (Hess et al. (1968); Holland et al. (1978)), including the promoter for 3 phosphoglycerate kinase (Hitzeman (1980)). Terminators may also be included, such as those derived from the enolase gene (Holland (1981)). Particularly useful control systems are those which comprise the glyceraldehyde-3 phosphate dehydrogenase (GAPDH) promoter or alcohol dehydrogenase (ADH) regulatable promoter, terminators also derived from GAPDH, and if secretion is desired, leader sequence from yeast alpha factor. In addition, the transcriptional regulatory region and the transcriptional initiation region which are operably linked may be such that they are not naturally associated in the wild-type organism. These systems are described in detail in EPO 120,551, published Oct. 3, 1984; EPO 116,201, published Aug. 22, 1984; and EPO 164,556, published Dec. 18, 1985.

Mammalian cell lines available as hosts for expression are known in the art and include many immortalized cell lines available from the American Type Culture Collection (ATCC), including HeLa cells, Chinese hamster ovary (CHO) cells, baby hamster kidney (BHK) cells, and a number of other cell lines. Suitable promoters for mammalian cells are also known in the art and include viral promoters such as that from Simian Virus 40 (SV40) (Fiers (1978)), Rous sarcoma virus (RSV), adenovirus (ADV), and bovine papilloma virus (BPV). Mammalian cells may also require terminator sequences and poly A addition sequences; enhancer sequences which increase expression may also be included, and sequences which cause amplification of the gene may also be desirable. These sequences are known in the art.

Vectors suitable for replication in mammalian cells are known in the art, and may include viral replicons, or sequences which insure integration of the appropriate sequences encoding PilC epitopes into the host genome.

A vector which is used to express foreign DNA, and which may be used in vaccine preparation is Vaccinia virus.

In this case the heterologous DNA is inserted into the Vaccinia genome. Techniques for the insertion of foreign DNA into the vaccinia virus genome are known in the art, and utilize, for example, homologous recombination. The insertion of the heterologous DNA is generally into a gene which is non-essential in nature, for example, the thymidine kinase gene (tk), which also provides a selectable marker. Plasmid vectors that greatly facilitate the construction of recombinant viruses have been described (see, for example, Mackett et al. (1984), Chakrabarti et al. (1985); Moss (1987)). Expression of the polypeptide containing at least one immunoreactive PilC epitope then occurs in cells or individuals which are immunized with the live recombinant vaccinia virus.

Other systems for expression of desired polypeptides include insect cells and vectors suitable for use in these cells. These systems are known in the art, and include, for example, insect expression transfer vectors derived from the baculovirus *Autographa californica* nuclear polyhedrosis virus (AcNPV), which is a helper-independent, viral expression vector. Expression vectors derived from this system usually use the strong viral polyhedrin gene promoter to drive expression of heterologous genes. Currently the most commonly used transfer vector for introducing foreign genes into AcNPV is pAc373. Many other vectors, known to those of skill in the art, have also been designed for improved expression. These include, for example, pVL985 (which alters the polyhedrin start codon from ATG to ATT, and which introduces a BamHI cloning site 32 basepairs downstream from the ATT; See Luckow and Summers (1989)).

Methods for the introduction of heterologous DNA into the desired site in the baculovirus virus are known in the art. (See Summer and Smith, Texas Agricultural Experiment Station Bulletin No. 1555; Ju et al. (1987); Smith et al. (1983); and Luckow and Summers (1989)). For example, the insertion can be into a gene such as the polyhedrin gene, by homologous recombination; insertion can also be into a restriction enzyme site engineered into the desired baculovirus gene. The inserted sequences may be those which encode all or varying segments of the polyprotein, or other orfs which encode viral polypeptides. For example, the insert could encode the following numbers of amino acid segments from the polyprotein: amino acids 1–1078; amino acids 332–662; amino acids 406–662; amino acids 156–328, and amino acids 199–328.

The signals for posttranslational modifications, such as signal peptide cleavage, proteolytic cleavage, and phosphorylation, appear to be recognized by insect cells. The signals required for secretion and nuclear accumulation also appear to be conserved between the invertebrate cells and vertebrate cells. Examples of the signal sequences from vertebrate cells which are effective in invertebrate cells are known in the art, for example, the human interleukin 2 signal ($IL2_S$) which is a signal for transport out of the cell, is recognized and properly removed in insect cells.

Recombinant polynucleotides are inserted into host cells by transformation. Transformation may be by any known method for introducing polynucleotides into a host cell, including, for example packaging the polynucleotide in a virus and transducing a host cell with the virus, and by direct uptake of the polynucleotide. The transformation procedure used depends upon the host to be transformed. Bacterial transformation by direct uptake generally employs treatment with calcium or rubidium chloride (Cohen (1972); Maniatis (1989)). Yeast transformation by direct uptake may be carried out using the method of Hinnen et al. (1978). Mammalian transformations by direct uptake may be conducted using the calcium phosphate precipitation method of Graham and Van der Eb (1978), or the various known modifications thereof. Other methods for the introduction of recombinant polynucleotides into cells, particularly into mammalian cells, which are known in the art include dextran-mediated transfection, calcium phosphate mediated transfection, polybrene mediated transfection, protoplast fusion, electroporation, encapsulation of the polynucleotide (s) in liposomes, and direct microinjection of the polynucleotides into nuclei.

The recombinant polynucleotide may be in the form of a vector. Vector construction employs techniques which are known in the art. Site-specific DNA cleavage is performed by treating with suitable restriction enzymes under conditions which generally are specified by the manufacturer of these commercially available enzymes. In general, about 1 microgram of plasmid or DNA sequence is cleaved by 1 unit of enzyme in about 20 microliters buffer solution by incubation of 1–2 hr at 37° C. After incubation with the restriction enzyme, protein is removed by phenol/chloroform extraction and the DNA recovered by precipitation with ethanol. The cleaved fragments may be separated using polyacrylamide or agarose gel electrophoresis techniques, according to the general procedures found in Methods in Enzymology (1980) 65:499–560.

Sticky ended cleavage fragments may be blunt ended using *E. coli* DNA polymerase I (Klenow) in the presence of the appropriate deoxynucleotide triphosphates (dNTPs) present in the mixture. Treatment with S1 nuclease may also be used, resulting in the hydrolysis of any single stranded DNA portions.

Ligations are carried out using standard buffer and temperature conditions using T4 DNA ligase and ATP; sticky end ligations require less ATP and less ligase than blunt end ligations. When vector fragments are used as part of a ligation mixture, the vector fragment is often treated with bacterial alkaline phosphatase (BAP) or calf intestinal alkaline phosphatase to remove the 5'-phosphate and thus prevent religation of the vector; alternatively, restriction enzyme digestion of unwanted fragments can be used to prevent ligation.

Ligation mixtures are transformed into suitable cloning hosts, such as *E. coli*, and successful transformants selected by, for example, antibiotic resistance, and screened for the correct construction.

The desired recombinant DNA sequences may be synthesized by synthetic methods. Synthetic oligonucleotides may be prepared using an automated oligonucleotide synthesizer as described by Warner (1984). If desired the synthetic strands may be labeled with $^{32}P$ by treatment with polynucleotide kinase in the presence of $^{32}P$-ATP, using standard conditions for the reaction.

DNA sequences, including those isolated from DNA libraries, may be modified by known techniques, including, for example site directed mutagenesis, as described by Zoller (1982). Briefly, the DNA to be modified is packaged into phage as a single stranded sequence, and converted to a double stranded DNA with DNA polymerase using, as a primer, a synthetic oligonucleotide complementary to the portion of the DNA to be modified, and having the desired modification included in its own sequence. The resulting double stranded DNA is transformed into a phage supporting host bacterium. Cultures of the transformed bacteria, which contain replications of each strand of the phage, are plated in agar to obtain plaques. Theoretically, 50% of the new plaques contain phage having the mutated sequence, and the remaining 50% have the original sequence. Replicates of the plaques are hybridized to labeled synthetic probe at temperatures and conditions which permit hybridization with the correct strand, but not with the unmodified sequence. The sequences which have been identified by hybridization are recovered and cloned.

DNA libraries may be probed using the procedure of Grunstein and Hogness (1975). Briefly, in this procedure, the DNA to be probed is immobilized on nitro-cellulose filters, denatured, and prehybridized with a buffer containing 0–50% formamide, 0.75M NaCl, 75 mM Na citrate, 0.02% (wt/v) each of bovine serum albumin, polyvinyl pyrollidone, and Ficoll, 50 mM Na Phosphate (pH 6.5), 0.1% SDS, and 100 micrograms/ml carrier denatured DNA. The percentage of formamide in the buffer, as well as the time and temperature conditions of the prehybridization and subsequent hybridization steps depends on the stringency required. Oligomeric probes which require lower stringency conditions are generally used with low percentages of formamide, lower temperatures, and longer hybridization times. Probes containing more than 30 or 40 nucleotides such as those derived from cDNA or genomic sequences generally employ higher temperatures, e.g., about 40°–42° C., and a high percentage, e.g., 50%, formamide. Following prehybridization, $5'-^{32}p$-labeled oligonucleotide probe is added to the buffer, and the filters are incubated in this mixture under hybridization conditions. After washing, the treated filters are subjected to autoradiography to show the location of the hybridized probe; DNA in corresponding locations on the original agar plates is used as the source of the desired DNA.

For routine vector constructions, ligation mixtures are transformed into *E. coli* strain HB101 or other suitable host, and successful transformants selected by antibiotic resistance or other markers. Plasmids from the transformants are then prepared according to the method of Clewell et al. (1969), usually following chloramphenicol amplification (Clewell (1972)). The DNA is isolated and analyzed, usually by restriction enzyme analysis and/or sequencing. Sequencing may be by the dideoxy method of Sanger et al. (1977) as further described by Messing et al. (1981), or by the method of Maxam et al. (1980). Problems with band compression, which are sometimes observed in GC rich regions, were overcome by use of T-deazoguanosine according to Barr et al. (1986).

An enzyme-linked immunosorbent assay (ELISA) can be used to measure either antigen or antibody concentrations. This method depends upon conjugation of an enzyme to either an antigen or an antibody, and uses the bound enzyme activity as a quantitative label. To measure antibody, the known antigen is fixed to a solid phase (e.g., a microplate or plastic cup), incubated with test serum dilutions, washed, incubated with anti-immunoglobulin labeled with an enzyme, and washed again. Enzymes suitable for labeling are known in the art, and include, for example, horseradish peroxidase. Enzyme activity bound to the solid phase is measured by adding the specific substrate, and determining product formation or substrate utilization calorimetrically. The enzyme activity bound is a direct function of the amount of antibody bound.

To measure antigen, a known specific antibody is fixed to the solid phase, the test material containing antigen is added, after an incubation the solid phase is washed, and a second enzyme-labeled antibody is added. After washing, substrate is added, and enzyme activity is estimated calorimetrically, and related to antigen concentration.

EXAMPLES

Described below are examples of the present invention which are provided only for illustrative purposes, and not to limit the scope of the present invention. In light of the present disclosure, numerous embodiments within the scope of the claims will be apparent to those of ordinary skill in the art.

Example 1

Isolation of PilC

An outer membrane preparation from *N. gonorrhoeae* strain $MS11_{ms}(P^+)$ contains small amounts of a 110 kd protein, PilC. This protein was enriched during alternate cycles of crystallization and solubilization of pili, unlike other outer membrane proteins that decreased in abundance by this procedure.

The materials and methods used for the isolation procedure were the following.
Bacterial strains and growth conditions

*N. gonorrhoeae* $MS11_{ma}$ (Meyer et al., 1984) and $P^-$ and $P^-n$ variants of $MS11_{mk}$ (Swanson et al., 1986) were kindly obtained from Dr. M. So and from Dr. M. Koorney, respectively. The gonococcal isolates UM01 and KH4318 have previously been described (Norlander et al., 1981). *N. gonorrhoeae* strains 605344 and 605103 were obtained from Dr. D. Danielsson, Örebro, Sweden, and strain 765 was isolated at the Department of Bacteriology in Umea, Sweden. The commensal Neisseria species *N. lactamica* Nctc 10618 and *N. subflava* GN01 were obtained from Pharmacia, Uppsala, Sweden. These bacteria were grown at 37° C. in a 5% $CO_2$ atmosphere on Difco GCB agar containing Kellogg's supplement. Piliated ($P^+$) and nonpiliated ($P^-$) variants were distinguished by colony morphology and passed as single colonies. *E. coli* strain Y 1090 (obtained from Promega Biotech) was used for plaque screening, DH5 (Hanahan, 1985) for molecular cloning, AA10 recA (Stoker et al. 1984) for isolation of minicells and TG1 (Gill et al., 1986) for propagation of M13 clones.
Preparation of pili and outer membranes Pili were prepared essentially as described by Brinton et al. (1978). Gonococci ($P^+$Tr) from 80 GGB plates, grown for 18 h, were harvested in 0.05M Tris-HCl pH 8.0 and 0.15M NaCl, washed twice and resuspended in 40 ml 0.15M ethanolamine pH 10.5. Pili were sheared off in a Sorvall Omnimixer, setting 3 for 30 s. The cell debris was pelleted at 13,000 g for 30 min at 4° C. and the supernatant was dialyzed against 0.05M Tris-HCl pH 8.0 and 0.15M NaCl. The crystallized pili were pelleted at 13,000 g for 60 min., resuspended in 0.15M ethanolamine pH 10.5, and centrifuged at 23,000 g for 60 min. The supernatant was dialyzed as described above against 0.05M Tris-HCl pH 8.0 and 0.15M NaCl. Several cycles of crystallization and solubilization were performed to produce pili preparations with high purity. Outer membranes of *N. gonorrhoeae* were prepared by the sarkosyl method described by Norquist et al. (1978).

Example 2

Preparation of Purified Anti-PilC Antibodies

The 110 kd protein present in purified $MS11_{ms}$ pili preparations was eluted from SDS polyacrylamide gels and rabbit antibodies were generated against the gel purified protein. The antiserum cross reacted extensively with the pilin protein in immunoblots and was therefore absorbed with extracts of *Pseudomonas putida* expressing the pilin subunit of *N. gonorrhoeae* on plasmid pGC02.

Pili preparations of N. gonorrhoeae $MS11_{ma}(P^+)$ crystallized 5 times were separated on 10% SDS-poly-acrylamide gels using the buffer system of Laemmli (1970). These gels were stained in 0.25M KCl and 1 mM DTT for 5 min., the 110 kd protein band was sliced out, crushed and incubated in a buffer containing 0.05M Tris-HCl pH 7.9, 0.1 mM EDTA, 5 mM DTT and 0.15M NaCl at 4° C. overnight. Gel pieces were removed by centrifugation prior to immunization of rabbits.

The achieved 110 kd-antiserum was extensively absorbed with Pseudomonas putida 2440 (Bagdasarien et al. (1983), carrying a recombinant plasmid, pGCO2, constructed as follows. The 1.0 kb HpaI-EcoRI fragment of the pilus gene clone pNG1100 (Meyer et al. 1984) obtained from M. So was cloned into the HpaI and EcoRI sites of pMMB66 (F ürste et al., 1986). The pilE gene is then under control of the tac promoter and induction with 1 mM IPTO resulted in high levels of pilin produced in P. putida 2440, but no extracellular pili structures were observed. Dense sonicated cultures of P. putida 2440/pGC02 were mixed in a 1:1 ratio with the crude antiserum. About 15 cycles of 1 h incubation and 30 min centrifugation at 25,000 g in the presence of 1 mM PMSF (phenylmethylsulfonylfluoride) at 4° C. were performed.

The pili antiserum used in immunoblots was generated in a rabbit against highly purified pili preparations of N. gonorrhoeae MS11$_{ma}$.

In immunoblots 10 μg of boiled bacterial cells or the same amount of outer membranes were electrophoresed on 10% SDS-polyacrylamide gels. The proteins were transferred from the gel onto nitrocellulose sheets where their immunological cross-reaction with the 110 kd absorbed antiserum was tested using an immunoblotting protocol as described by Towbin et al. (1979).

Example 3

Specificity of Purified Anti-PilC Antibodies

The absorbed antiserum was used in immunoblots with whole cell extracts of a number of N. gonorrhoeae strains as well as commensal strains of Neisseria (FIG. 2A). All strains of N. gonorrhoeae, except strain 605103, contained one or two high molecular weight protein species reacting with the antiserum. Strain 605103, unlike the other strains tested, was nonpiliated and no piliated variants could be obtained suggesting that it is a P⁻n variant (Swanson et al., 1985). This was confirmed by Southern blot hybridization using an oligonucleotide probe corresponding to the 5' end of the pilE gene. No hybridization was obtained with this probe. The commensal N. lactamica Nctc10618, but not N. subflava GN01, contained a high molecular weight protein reacting with the 110 kd antiserum. Immunoblots against outer membrane preparations of P⁺ and P⁻n MS11$_{mk}$ showed the 110 kd protein to be present in the outer membrane in both of these MS11 variants.

Southern blot hybridization was accomplished as follows. Digested genomic DNA was separated on 0.7% agarose gels and transferred to nitrocellulose filters (Southern, 1975). After transfer and baking the filters were prehybridized in a mixture of 5× SSC, 0.1% SDS, 5 mM EDTA, 5× Denhardt's solution and 100 μg/ml of sonicated calf thymus DNA at 65° C. for 2–6 h. $^{32}$P-labeled probe (multiprime DNA labelling system, Amersham International) was added and hybridization was performed for 12–15 h at the same temperature. The filters were washed in 2× SSC with 0.1% SDS and in 0.2× SSC with 0.1% SDS for 2×15 min each, dried and exposed to Kodak XRP film at –80° C.

A 21-base-long oligonucleotide complementary to the signal peptide coding region of pilE (5'-GCCTTTTTGAAGGGTATTCAT-3') (SEQ ID NO:37) was $^{32}$ P-labeled with T4 polynucleotide kinase and used to probe ClaI-digested genomic DNA. The blot was prehybridized at 37° C. in a mixture containing 2× Denhardt's, 0.1% SDS, 2.5 mM EDTA, 5× SSC and 100 μg/ml sonicated calf thymus DNA, hybridized at 37° C. and washed in 2× SSC for 5 min. MS11$_{mk}$(P⁺) gave a 4 kb hybridization fragment, whereas MS11$_{mk}$(P⁻n) and 605103 gave no hybridization signal.

Example 4

Molecular cloning of the pilC1 gene encoding a 110 kd protein

Chromosomal DNA from N. gonorrhoeae MS11$_{mk}$(P⁺) was used to construct a λgt11 library. The library was screened with the absorbed 110 kd antiserum and one positive clone out of 10,000 plaques was found, containing an 800 bp insert. A lysogen of this positive λgt11 clone was examined in immunoblots and a fusion protein with an estimated size of 150 kd reacted with the antiserum (data not shown). The 800 bp insert was purified, labeled with $^{32}$P, and used as a probe to screen a plasmid library from N. gonorrhoeae MS11$_{ms}$. Six clones out of 10,000 hybridized with the probe. Restriction maps for these partially overlapping six clones are shown in FIGS. 1A–1B.

Figure 1B:
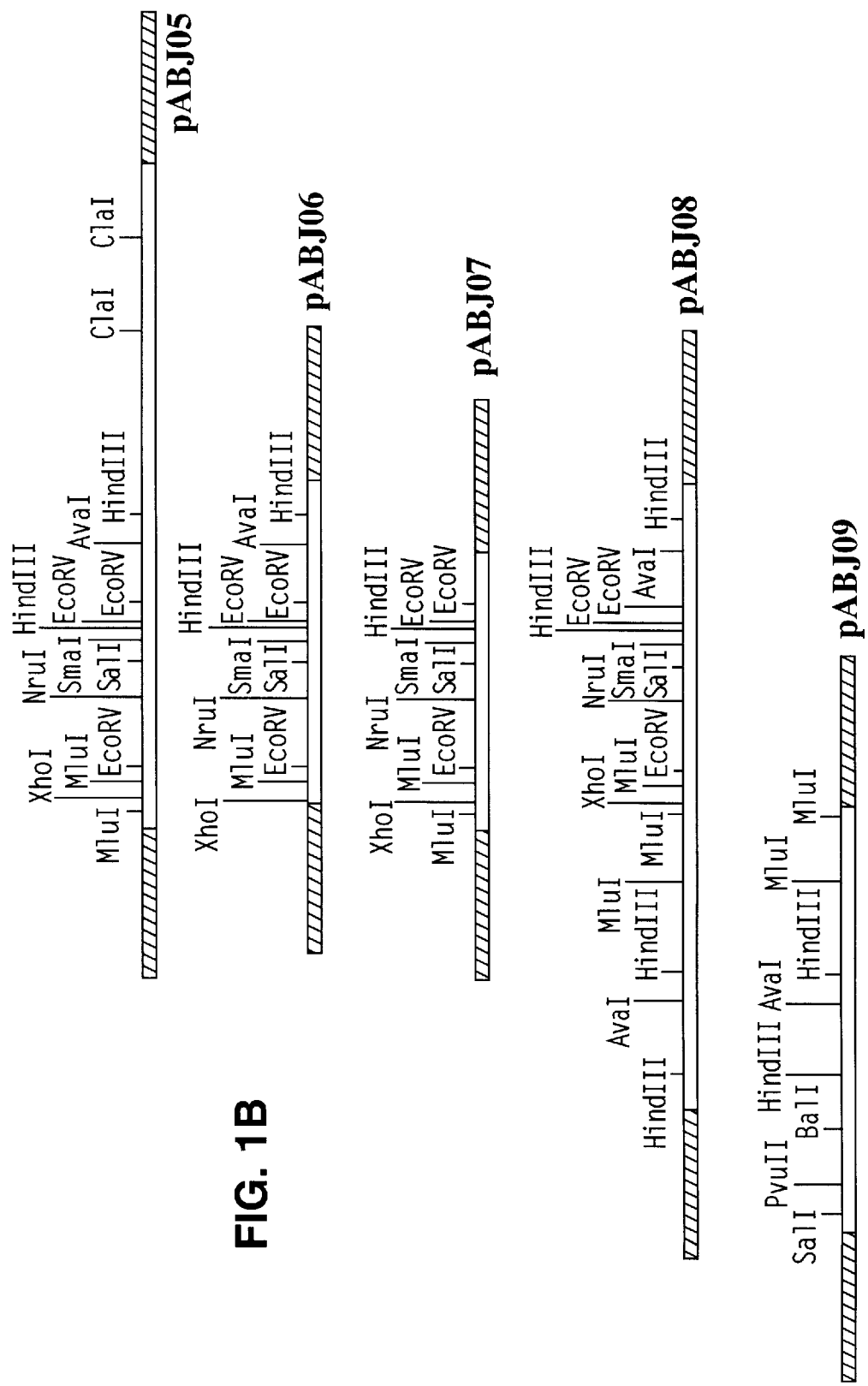

In FIGS. 1A and 1B, plasmids pABJ04–09, which all belong to locus 1, were isolated from a plasmid library using the 800 bp insert from λgt11 as a probe. The λgt11 insert (from locus 2) has an additional SalI site not found in the plasmid clones. The position of the pilC1 gene and direction of its transcription (indicated by an arrow) were determined in E. coli minicells. Three thickened lines, with an arrowhead at each end, indicate fragments used as probes in Southern hybridizations. I.e., the 800 bp insert from λgt11, the EcoRV$_1$-EcoRV$_2$ (1.3 kb) and the EcoRV$_3$-HindIII$_4$ (0.8 kb) fragments of pAGJ04. Triangles mark the location of two mTnCm insertions in pABJ04. The resulting plasmids, pABJ)4::mTnCm-12 and pABJ04::mTnCm-14 were used, were used to inactivate pilC1 and pilC2.

The six plasmid clones, pABJ04–09, were transformed into the minicell producing strain AA10 to monitor expression of plasmid encoded [$^{35}$S]methionine labeled proteins. The E. coli minicell strain AA10 was transformed with plasmid DNA (pABJ04–09) and chromosome deficient minicells from these strains were purified over sucrose gradients (Thompson and Achtman, 1978). The plasmid-encoded proteins were labeled in the presence of 80 μCi [$^{35}$S]methionine in minimal salts medium and 1% methionine assay medium (Difco). After lysis of the minicells in sample buffer (Laemmli, 1970) the proteins were electrophoresed on an SDS-polyacrylamide gel, the gel was dried and exposed to X-ray film (Kodak X-OmatAR).

Plasmid pABJ04 expressed minute amounts of three high molecular weight proteins, 113, 111 and 108 kd in size, as well as a number of lower molecular weight protein species not produced from the vector control. The three high molecular weight bands were missing in pABJ05 and pABJ06 but three novel lower molecular weight protein species had appeared, suggesting that pABJ05 and pABJ06 are deleted for the 3' end of a gene, denoted pilC1, and that this gene is responsible for all three high molecular weight species. This suggested that the distal end of the gene must be located between the MluI$_1$ and MulI$_2$ sites (FIGS. 1A and 1B). The observation that plasmid pABJ07 did not express any high molecular proteins tentatively located the 5' end of the gene to a region 0.5–1.2 kb to the right of the EcoRV$_3$ site. The size for a gene encoding a 110 kd protein is ~3 kb which is in agreement with these mapping data.

Example 5

Identification of a Second Gene Encoding PilC

The 800 bp insert in λgt11 contains a single SalI site not present in the region on pABJ04 which hybridized to this fragment, suggesting that there is more than one pilC locus in the genome of *N. gonorrhoeae* MS11. This was confirmed in Southern blot hybridizations in which three different pilC fragments were used to probe SmaI and ClaI digested genomic DNA. The 800 bp fragment from λgt11 hybridized in a Southern blot to two ClaI (18 and 8 kb) and SmaI (13 and 4.5 kb) fragments of DNA prepared from *N. gonorrhoeae* MS11$_{mk}$. Since the probe does not contain any internal ClaI or SmaI sites, there are presumably two copies of the 3' end of pilC in the MS11 genome. The 1.3 kb EcoRV$_1$-EcoRV$_2$ fragment of pABJ04 carries the central region of pilC1. This probe hybridized to the same two ClaI fragments and to four SmaI fragments, two of which are the same size as the two SmaI fragments identified with the 800 bp probe (13 kb and 4.5 kb). Hybridization with the 800 bp probe was more extensive to the 8 kb ClaI and the 4 kb SmaI fragment whereas the reverse was found with the 1.3 kb EcoRV$_1$-EcoRV$_2$ fragment from pABJ04 strongly suggesting that the two genomic copies of pilC show a significant sequence variation in the 3' as well as in the central region. A probe corresponding to the 5' region of pilC1 was also used in Southern hybridization experiments. This 0.8 kb HindIII$_4$-EcoRV$_3$ fragment hybridized to two ClaI (18 kb and 4 kb) and SmaI (25 kb and 7 kb) fragments with seemingly equal efficiency. The hybridization pattern was identical using DNA from MSII$_{ms}$. Taken together these hybridization data indicate that *N. gonorrhoeae* MS11 contains two complete copies of pilC. Furthermore the two genes appear to be more homologous in their 5' as compared to their central and 3' regions.

The results indicate that the 800 bp insert from λgt11 carries information from pilC2 whereas the clones pABJ04–09 must carry information from pilC1. Finally pilC2 must be located >2 kb from either end of pilC1. The DNA sequence of the 3'-end of the pilC2 fragment is shown in FIG. 7. The sequence showing the putative amino acids encoded therein are shown in FIG. 8. A comparison of the analogous portions of pilC2 (top) and pilC1 (bottom) DNA sequences, and the putative amino acids encoded therein are shown in FIGS. 9A and 9B.

The 800 bp fragment from pilC2 was also used to probe digested genomic DNA from *N. gonorrhoeae* strains UM01, 765 and 605103. The latter isolate does not express detectable levels of the 110 kd protein. Strain UM01, unlike MS11, contained only one ClaI fragment of 15 kb that hybridized to the probe (data not shown). Hence, this strain may contain only one copy of pilC. Strain 605103 and 765, on the other hand, each seem to contain two copies of pilC since two ClaI and two SmaI fragments hybridized to the 800 bp probe.

The commensal *N. lactamica* Nctc10618 DNA digested with ClaI and SmaI also hybridized with the 800 bp probe. Since only one band hybridized in each case this strain may contain only one copy of pilC. In contrast, *N. subflava* GN01 did not hybridize to the 800 bp pilC2 probe using the same stringency.

Example 6

Characterization of the pilC Genes
The pilC1 gene on pABJ04 is translationally out of frame The amino terminal sequence of gel purified 110 kd protein from strain MS11$_{ms}$ (P$^+$) was determined by sequential Edman degradation. For aminoterminal sequence determination automated Edman degradations (Edman and Bregg, 1967) were performed in an updated Beckman 890C spinning cup sequencing sequencer. The sequencing procedure and the method for analysis of the 3-phenyl-2-thiohydantoin derivatives been described (Engström et al., 1984). Considerable difficulties were encountered in the method probably due to blocking of the N-terminus. As a result, only the residues from position 4 to 10 were obtained (FIG. 2).

The 3.3 kb HindIII$_4$-MluI$_1$ fragment encompassing the entire pilC1 gene was sequenced on both strands using the dideoxy sequencing method adapted for single stranded DNA.

Purified DNA fragments from pABJ04 and PCR-amplified 5' end of pilC1 was subcloned into M13 vectors (Sanger et al., 1980: Yanish-Perroa et al., 1985) and sequenced using the chain termination method of Sanger et al. (1977). Primers used were the M13 17-mer universal primer and oligonucleotides synthesized at Symbicon, Ume a, Sweden or at the Department of Biochemistry, Washington University, St., Louis, Mo., USA.

The results of the sequencing showed that the pilC1 contained one single open reading frame of 997 codons (from left to right in FIG. 2) and starting at an AUG codon 195 bp from the HindIII$_4$ site. Codons 7–12 in this open reading frame corresponded to amino acids 5–10 in the sequence of the gel purified protein. The AUG codon in the beginning of the long open reading frame was not preceded by a typical Shine-Dalgarno sequence. Moreover, since the 110 kd protein is located in the outer membrane of *N. gonorrhoeae*, we expected the protein to be translated with a signal sequence. When examining the nucleotide sequence, an AUG codon was found in frame 1 that was preceded by a typical Shine-Dalgarno sequence (-AGGAA-). The sequence following this AUG codon would encode a typical signal peptide with basic amino acids in the amino terminal region and a hydrophobic central region. However, no signal peptidase cleavage site could be predicted following the rules of von Heijne (1983). A tract of 12G residues was found in the region encoding the putative signal peptide for PilC. Addition of one G residue or the loss of two would align the long open reading frame with the AUG codon in frame 1. The translated region in frame 2 contains a putative signal peptidase cleavage site between Ala and Gln. A cleavage at this site would align the determined amino acid sequence at positions 5–10 for the 110 kd protein with the deduced amino acid sequence. The data therefore suggested that the cloned pilC1 gene is out of frame due to frameshifting in the region encoding the signal peptide.

FIG. 2 shows the nucleotide sequence and the deduced amino acid sequence of the 5'-end of pilC. The aminoterminal sequence of gel purified PilC from MS11$_{ms}$(P$^+$) is shown in a box below frame 2, a 997 amino acid long open reading frame that would code for a protein about 110 kd in size. Frame 1 contains 41 amino acids and is preceded by a putative Shine-Dalgarno sequence (underlined). Two horizontal lines mark a stretch of 12 G residues. An addition of one G in this region would align the ATG (boxed) in frame 1 with frame 2. Numbers above the sequence show base positions relative to the HindIII$_4$ site (=0) located on pABJ04. The position of two 24 bp oligonucleotide primers (opposite stands) used for PCR amplification, are indicated above the sequence by hatched bars.

FIGS. 3A and 3B show the nucleotide sequence of the sense strand of the pilC1 gene.

FIGS. 4A through 4D show the shows the nucleotide sequence of the sense strand of the pilC1 gene and the amino acids encoded therein.

Genetic inactivation of pilC2 but not pilC1 abolishes expression of the 110 kd protein in MS11

Plasmid pABJ04 was mutagenized in *E. coli* by a transposon mini-Tn3 derivative, mTnCm. The shuttle mutagenesis system developed by Seifert et al., (1986) using a miniTn3 carrying the chloramphenicol resistance gene was kindly provided by Dr. M. So. Mutagenesis of pABJ04 with mTnCm and transformation of *N. gonorrhoeae* were performed as previously described (Seifert et al., 1990). MiniTnCm insertions at 30 different positions in pABJ04 were identified, two of which mapped within the PilC gene. Piliated *N. gonorrhoeae* MS11$_{mk}$ were transformed with 2 $\mu$g plasmid DNA, transformants were selected for on plates containing 10 $\mu$g/ml chloramphenicol for the single mutants and 30 $\mu$g/ml chloramphenicol for the double mutants.

Only two mTnCm insertions had occurred in pilC1 (FIG. 1A and 1B). Truncated protein species were seen in minicells with the mTnCm-14 insertion located 0.5 kb from the 3' end of pilC1 but not with the mTnCm-12 insertion located 0.5 kb from the 5' end of the gene. Both insertion mutants were used in a gene replacement experiment. Plasmids pABJ04::mTnCm-12 and pABJ04::mTnCm-14 were linearized with BamHI and transformed into *N. gonorrhoeae* MS11$_{mk}$(P$^+$) and transformants resistant to 10 $\mu$g/ml of chloramphenicol were selected. Forty-eight P$^+$ transformants (24 from each experiment) were assayed for the presence of PilC in immunoblots. All these transformants remained capable of expressing the PilC protein. Genomic DNA was prepared from seven of the chloramphenicol resistant transformants (five from pABJ04::mTnCm-12 and two from pABJ04::mTnCm-14), cleaved with ClaI and PvuII and used in Southern blot experiments using the EcoRV$_1$-EcoRV$_2$ fragment of pABJ04 as a probe. The 8 kb ClaI fragment was unaffected in the mutants whereas the 18 kb ClaI fragment had been replaced by a 20 kb fragment. PvuII cleaves within the 1.6 kb mTnCm element. The probe detected an 8 kb PvuII fragment in both parent and mutant DNA. In the mutants, a novel PvuII fragment appeared that was 6.2 kb in size in five transformants obtained with pABJ04::mTnCm-12 and 4.8 kb in size in two transformants with pABJ04::mTnCm-14. To confirm the insertion of mTnCm, a 250 bp EcoRI-HindIII fragment of the CAT GenBlock (Pharmacia, Sweden), containing the PvuII site, was used as a probe. It detected the larger of the two ClaI fragments as well as the 6.2 kb PvuII fragment. In addition, a 2 kb PvuII fragment not covered with the pilC probe was detected. These data demonstrate that we have obtained gene replacements in pilC1, whereas pilC2 was unaffected in all seven P$^+$, PilC$^+$ transformants. A rapid hybridization was done to screen the remaining 41 P$^+$ transformants. All but one had mTnCm inserted in pilC1. The remaining transformant had an intact locus 1 and 2 and must therefore contain mTnCm elsewhere in the gonococcal chromosome.

In the same transformation experiments, the frequency of P$^-$ colony variants was about five-fold higher as compared with that occurring normally in strain MS11$_{mk}$(P$^+$). Two P$^-$mTnCm-12 transformants isolated at 10 $\mu$g/ml of chloramphenicol were also analyzed by Southern blot hybridization using the EcoRV$_1$-EcoRv$_2$ fragment of pABJ04 and the EcoRI-HindIII fragment of the CAT GenBlock. Each of these mutants carried mTnCm in pilC2 as evidenced by a replacement of the 8 kb ClaI fragment by a fragment 9.5 kb in size that hybridizes to both probes. These pilC2::mTnCm insertion mutants did not express PilC as determined by immunoblot analysis.

A P$^+$, pilC1::mTnCm-12 mutant was retransformed with DNA prepared from a P$^-$, pilC2::mTnCm-12 mutant and colonies growing at 30 $\mu$g/ml of chloramphenicol were selected to obtain double mutants in pilC. All resistant transformants were P$^-$, and when analyzed by Southern blot hybridization all contained mTnCm in both pilC1 and pilC2. Electron microscopy revealed that the P$^+$, pilC1::mTnCm-12 mutant still expressed pili albeit at a slightly lower level than the MS11$_{mk}$(P$^+$) parental clone, whereas the P$^-$, pilC2::mTnCm-12 was completely bald as was the pilC1, pilC2 double mutant.

Immunoblot analyses were performed on the P$^+$pilC1::mTnCm-12 mutant, the P$^-$, pilC2::mTnCm-12 mutant and the P$^-$, pilC1::mTnCm-12, pilC2::mTnCm-12 double mutant, using PilC and pili antisera. Inactivation of pilC1 did not abolish expression of PilC or the pilin. Inactivation of pilC2 totally abolished expression of PilC but did not affect expression of pilin. The pilC1, pilC2 double mutant was PilC$^-$ but produced only low levels of pilin. Taken together these data imply that pilC2 but not pilC1 is expressing PilC in the MS11 variant under study. Moreover, inactivation of pilC2 but not pilC1 was associated with a loss of piliation.

P$^+$ revertants occurred spontaneously at a low frequency in the pilC2::mTnCm-12 mutants. These revertants expressed pili as determined by electron microscopy and also expressed PilC. It is likely that PilC expression is due to in-frame switching in pilC1.

FIGS. 5A through 5D show the nucleotide sequence of the sense strand of the pilC1 gene, and the effect of frame shift on the putative gene products encoded therein.

The pilC genes of *N. gonorrhoeae* vary in the length of the G tract

Polymerase chain reaction (PCR) with Taq polymerase was used to analyze the 5' region of pilC using two 24 base long synthetic oligonucleotides based on the sequence of pilC1 (FIG. 2). These oligonucleotides would generate an amplified fragment of 149 bases as judged from the sequence obtained from pABJ04.

Polymerase chain reaction was carried out in 100 $\mu$l containing 50 ng of genomic DNA or 5 ng of plasmid DNA. 1.0 $\mu$M of each oligonucleotide, 200 $\mu$M of each nucleotide, 0.001% gelatin, 1.5 mM MgCl$_2$. 10 mM Tris (pH 8.3), 50 mM KCl, 0.25 $\mu$l 1 mCi/ml [$^{32}$P]dATP and 2 U of Taq Polymerase (Perkin Elmer Cetus). The samples were passed through 25 cycles: 2 min at 50° C., 1 min at 94° C. and 3 min at 72° C. in a Thermal Cycler (Perkin Elmer Cetus). Aliquots of the DNA fragments were denatured at 95° C. for 2 min and electrophoresed on standard denaturing sequencing gels.

The amplified products from MS11$_{mk}$(P$^+$) DNA were 149 and 150 long respectively. In addition, two less abundant products of 151 and 148 bases were seen. The amplified products were electroeluted and cloned into M13mp18, and twenty phage clones were sequenced using a universal primer. Four different sequences were obtained (FIG. 6).

FIG. 6 shows the nucleotide sequence of PCR amplified fragments demonstrating a variation in the length of the G tract and sequence differences in the 5'-region of the pilC genes. The two oligonucleotide primers used for the PCR are shown in FIG. 2. Amplified DNA was cloned into M13mp8 and sequenced. Shown are the complete nucleotide sequence in between the two primers. In-frame sequences are translated and the G stretches are underlined. The putative cleavage sites are marked with arrows. Genomic DNA from *N. gonorrheae* strains MS11(P⁺.PilC⁺), UM01(P⁺.PilC⁺), 765 (P⁺.PilC⁺) and 605103 (P⁻n.PilC⁻), and purified DNA from pABJ04/AA10(recA) was used in the PCR.

Variant patterns 1a and 1b were identical to each other and to the cloned sequence on pABJ04 except for the presence of 11 instead of 12 G residues in the G tract of 1b. The G tract of sequence 2a was 13 residues long indicating that the sequence is in frame. In addition, this sequence differed from pilC1 by four basepair substitutions outside the G tract, including an AAA lysine codon four triplets downstream of the putative signal peptide processing site which is in agreement with the lysine residue found in the fourth position of the gel purified 110 kd PilC protein. Sequences 1a and 1b contained CAA, the codon for Gln, at the same position. Sequence 2b was identical to 2a except for the presence of 12 G residues in the G tract. These data are compatible with sequence 1 being from pilC1 and sequence 2 from pilC2 and further support that pilC2 must be the expressed locus in the MS11(P⁺) variant we are studying.

Strain UM01 apparently only contains one copy of pilC. DNA from this strain generated five amplified fragments ranging in size from 148 to 152 bp in the PCR reaction. The most abundant fragments were 149–151 bp long. Among ten M13 clones, three variant 1 sequences were found (a,b,c) that differed only in the number of G residues (11–13) in the G tract (FIG. 6) supporting the hybridization data that this strain contains only one pilC gene. Since a PilC protein is expressed from UM01 we suggest that the majority of cells has 13 Gs in the G tract.

Strain 765 contains two pilC loci, both of which seem to be translationally ON based on the presence of two high molecular weight proteins reacting with the absorbed PilC antiserum. A number of amplified fragments were seen after the PCR reaction ranging in size from 149 to 153 bases. Three variant sequences were found among nine clones (FIG. 6). The G tract was 13 residues long in variant 3a (in frame) and 14 (out of frame) in variant 3b whereas sequence variant 4 contained 11 G residues in the G tract. Variant sequence 4 contained four additional nucleotides (-CAGG-) distal to the G tract relative to variant sequences 1, 2 and 3, indicating that the amplified product with 11 Gs from this variant sequence is 152 long and out of frame. Two PCR amplified products 152 and 153 in length were obtained from strain 765 suggesting that in frame variants of sequence 4 might be present in the DNA prepared from this strain.

Strain 605103 carries two pilC copies, both of which seem to be translationally OFF. The amplified fragments were 148 and 149 bases in size. Out of eight M13 clones only variant 1a and 1b sequences were found, with 11 and 12 Gs in the G tract respectively. Consequently, we were unable to find an in frame sequence variant from this strain. We do not know if the 5' ends of the two pilC genes are identical in this strain or if one pilC gene differed from pilC1 in the region corresponding to the oligonucleotides used for amplification. In the latter case we would not expect to obtain any amplified products from the second copy.

The only in frame variant found in DNA amplified from *N. gonorrhoeae* carried 13 Gs in the G tract. To see if variants with 10 Gs arise in products expressed in *E. coli*, PCR amplified products were generated from pABJ04 purified from *E. coli* strain AA10, using the same two oligonucleotide primers as before. Out of 12 sequenced clones, two carried 10 Gs in the G tract (FIG. 6). The majority of clones (seven) carried 12 Gs as expected. It is likely that the PCR amplification products are not representative of the original DNA population. However, the distribution of variation in the G tract is consistent with a model in which only one G residue is gained or lost at one given event. Since AA10 is recA, frameshift mutations in the G tract in *E. coli* occur independently of the RecA protein.

*N. meningitidis* contains two pilC loci Southern blot hybridizations using MS11 pilC1⁻ specific probes identified multiple fragments when meningococcal genomic DNA is digested with a variety of restriction endonucleases. PCR amplification using two 24-base oligonucleotides from the 5' end of MS11 pilC1 as primers yields multiple fragments ranging in size from 148 to 151 bases. DNA sequencing of fragments cloned into phage M13 identifies two classes of sequences, as in *N. gonorrhoeae*, which differ outside the G-tract. Variation occurred within each class with respect to the number of G's in the G-tract. Therefore, *N. meningitidis* must carry two pilC loci, as does *N. gonorrhoeae*, which should also be under the control of translational frame shifting.

Both pilC loci are cloned from *N. meningitidis* by generating an EMBL3 library and screening this library with pilC1⁻ and pilC2⁻ specific DNA from *N. gonorrhoeae* strain MS11.

Genomic DNA from *N. meningitidis* is partially digested with Sau3A and fragments ranging from 9 to 20 kB are ligated into the lambda EMBL3 vector. Because of the packaging constraints of the phage, only those lambdas which contain DNA fragments of this size will be packaged (i.e., are viable). The library thus constructed can be screened with genomic oligonucleotide or cloned gene probes following selection in a lysogenic *E. coli* strain. (Frischart, A.M. et al (1983), J. Mol. Biol. 170:827). Preferably, full length clones are identified by screening for clones hybridizing to both the 5' and 3' ends of pilC. If full length clones cannot be obtained from the EMBL3 library, pilC specific probes may be used to screen a plasmid library from the same strains.

Translational fusion proteins with β-galactosidase may also be screened for in a λgt11 library, using β-galactosidase and PilC⁻ specific antisera in Western immunoblots. β-galactosidase-PilC1 and β-galactosidase-PilC2 fusion proteins are purified from the cytoplasm of recombinant *E. coli* and used to raise specific antisera.

Example 7

The immunobiological properties of PilC

PilC is located in the outer membrane of Neisseria. The immune response during natural infection can be assessed by screening convalescent sera for anti-PilC antibody. The presence of only two pilC loci suggests that PilC is only moderately variable, however. This together with its essential role in pilus biogenesis makes PilC attractive as a potential vaccine candidate.

Two types of PilC translational fusions using alkaline phosphatase and β-galactosidase are generated. In the first instance a secreted fusion protein is obtained that may associate with the outer membrane. In the second instance the fusion proteins may accumulate in the cytoplasm as inclusion bodies. The construction schemes for such fusion proteins uses techniques known in the art. TnphoA insertions on plasmid pABJ04 in *E. coli* are generated, and a PhoA⁺ phenotype is screened for as blue colonies on media containing the chromogenic substrate XP. If such clones have the phoA gene in frame with an in frame variant of pilC1 the fusion product should be able to cross the cytoplasmic membrane where it can be analyzed by Western immunoblots using an alkaline phosphatase specific antiserum and our PilC antiserum raised against gel-purified PilC2 from MS11 (P$^+$). LacZ::pilC fusions are generated by cloning different segments of pilC into a lacZ$^-$ containing vector used to generate translational fusions. Similar constructs are performed on each of the two pilC genes from N. meningitidis. Antisera are generated against fusion proteins after their purification using conventional protocols. These antisera are extensively adsorbed with extracts of E. coli expressing alkaline phosphatase and β-galactosidase, and used in Western immunoblots and ELISA assays against a panel of Neisseria gonorrhoeae and Neisseria meningitidis strains. Antisera raised against fusion proteins carrying the major portion of PilC are also analyzed in Western blots using E. coli expressing fusion proteins containing only smaller regions of PilC. The results of these studies should show which regions in PilC are immunodominant. The pilC1 and pilC2 genes are highly homologous in their 5' ends whereas the homology is considerably less pronounced in the central and 3' region.

In addition, the entire pilC2 gene from N. gonorrhoeae MS11(P$^+$) is cloned and sequenced. Algorithms are used to search for potential T-cell epitopes (amphipathic helical conformation) and β-cell epitopes. Polypeptides containing the predicted epitopes are tested to determine if they can prime mice for an enhanced immune response to PilC1 and PilC2.

Specific PilC antisera are used in immunoelectromicroscopy with piliated Neisseria cells as well as with purified pili to see if PilC is physically connected with the pilus fiber.

Neisseria is grown in the presence of different dilutions of PilC$^-$ specific antibodies. Bactericidal effect exerted by the antiserum, effects on piliation, and effects on bacterial attachment to corneal primary culture cells are monitored. Binding assays to epithelial cells are described in Tjia, K. F. et al. (1988), Graefe's Arch. Clin. Exp. Opthalmol. 226:341–345.

Example 8

Identification and characterization of genes located adjacent to pilC

The pilC1 and pilC2 loci are part of a larger duplication that extends both 5'- and 3'- of pilC. We know from our work with E. coli that strains may contain multiple gene clusters for the same class of pili. In one case we have shown that the only difference between two duplicated gene clusters (pap and prs) resides in the adhesion genes such that each cluster gives rise to serologically identical pili binding to different cell surface receptors.

mTncm mutagenesis in the region upstream and downstream of pilC1 is performed to generate allelic replacements in the pilC1 and pilC2 regions on the chromosome. Since the two regions are highly homologous we expect to obtain for each insertion allelic replacements in either region. Double mutants are generated as before by isolating DNA from mutants carrying insertions in the pilC2 region transforming P$^+$ variants carrying the same insertion in the pilC1 region and select for transformants resistant to 30 μg/ml of chloramphenicol. These double mutants are examined for piliation, pilins expression, and binding to corneal primary culture cells.

Example 9

Phase variation in gonococcal pili expression can be caused by frameshift mutations in pilC If PilC is required for pilus formation, we would expect some P$^-$ progeny arising from a P$^+$ clone to accumulate unassembled pilin in the absence of PilC. Nonpiliated (P$^-$) colonies were derived from MS11$_{mk}$(P$^+$), restreaked, and tested for the presence of PilC and pilin in immunoblots with the PilC and pili antisera. Five out of eight P$^-$ clones did not produce detectable levels of PilC, but expressed the pilin subunit. The remaining three P$^-$ clones expressed PilC but not pilin. The molecular mass of the pilin subunit was the same in the P$^-$, PilC$^-$ variants as in MS11$_{mk}$(P$^+$, PilC$^+$). However, the former in addition produced a protein reacting with the pili antiserum that was 16 kd in size. Since MS11$_{mk}$ only contains one expression site for pilin we believe that this protein species represents a proteolytic degradation product of the pilin and may be identical to the S-pilin previously described (Haas et al., 1987). Several independent P$^-$ clones were isolated from one P$^-$, PilC$^-$ clone. They all remained PilC$^-$ and retained expression of pilin. Piliated (P$^+$) revertants were also obtained from the same P$^-$, PilC$^-$ clone. These P$^+$ revertants occurred at about a tenfold lower frequency (10$^{-4}$) than P$^-$ derivatives from a P$^+$ clone. All P$^+$ revertants from a P$^-$, PilC$^-$ clone had regained expression of PilC. All but one expressed a pilin with the same molecular weight as the nonpiliated parent. However, the low molecular weight pilin degradation product was much less abundant in the P$^+$, PilC$^-$ revertants. It was possible to obtain P$^+$ revertants from other P$^-$, PilC$^-$ clones as well, all of which expressed PilC.

The pilE gene from one set of PilC switches was PCR amplified and sequenced directly. The P$^-$, PilC$^-$, pilin$^+$ variant 8 carried eight amino acid changes in the pilin relative to the parental clone MS11$_{mk}$. The pilin sequence of the P$^+$, PilC$^-$ backswitcher 8:1 was identical to variant 8. Thus, the backswitching from P$^-$ to P$^+$ colony morphology was not associated with any alteration in the pilus subunit protein implying that the change in colonial morphology was due to the switch in PilC expression.

Strain MS11$_{mk}$(P$^-$), variants 8(P$^-$) and 8:1 (P$^+$) were also examined by transmission electron microscopy. Electron microscopy was performed with a JEOL 100CX microscope with 200-mesh copper grids coated with thin films of 2% Formvar. The bacterial colonies were carefully overlaid with buffer [10 μM Tris-HCl (pH 7.5), 10 μM magnesium chloride] and the cells were allowed to sediment for 15 min on a grid. The grids were washed with water, negatively stained with 1% sodium silicotungstate (pH 7.0) and then washed again.

The electron micrographs showed that the MS11(P$^+$) parental cells were heavily piliated and pili were often seen to aggregate. In contrast most cells of variant 8(P$^-$) were nonpiliated. One or two pili were found on ~10% of these cells. All cells of variant 8:1 (P$^+$) were piliated, carrying ~10–40 fibers/cells. No aggregation of individual fibers was seen. These data confirm that the observed changes in colonial morphology reflect alterations in expression of pili. Therefore, phase variation of gonococcal pili may not only be caused by recombination events occurring in the pilE locus (Bergstrom et al, 1986; Swanson et al., 1986) but also by frameshift mutations in pilC.

Example 10

Immunogenicity of PilC

In order to predict a region of PilC which would have a high probability for antigenicity, residues 300 to 700 of the putative PilC1 protein encoded within pilC1 were analyzed for antigen index, hydrophilicity, and hydrophobicity using standard computer-modelling methods. The analysis indicated that the PilC1 polypeptide fragment containing residues 300 to 700 would have several regions with a high antigen index, high hydrophilicity, and a high likelihood for location in an external domain.

The immunogenicity of a recombinant polypeptide expressed from the DNA encoding amino acids 300 to 700 was examined. The region of DNA encoding amino acid residues 300 to 700 was amplified by polymerase chain reaction (PCR) using the following oligonucleotide primers.

5' GGC TAG GTG GCA TAT GAA AGA TAC CGG 3' (SEQ ID NO: 38)

and

5' TTT GCA ATC GGG GAT CCT* C*A*G GTG TCT TTC 3' (SEQ ID NO: 39)

These primers incorporate an NdeI and a BamHI restriction endonuclease site (indicated by the underlined nucleotides), respectively. A termination codon (indicated by the asterisks) was also incorporated. The PCR amplified DNA was then ligated into the vector pET3a (between the NdeI and BamHI sites). The recombinant vector pET3a is used in the inducible expression system described by Studier et al. (1990), using the protocol described therein. Strain BL21 (DE3) was transformed with the pET3a-pilC (300–700) vector, and the transformed strain used for the expression of the PilC (300–700) peptide.

The expression products after induction were analyzed by sodium dodecyl sulfate-polyacrylamide gel electrophoresis (PAGE) using an 8% acrylamide gel and the standard 25 mM Tris base/250 mM glycine/pH 8.3/0.1% sodium dodecyl sulfate (SDS) electrophoresis buffer. After electrophoresis, the gel was fixed and then stained with Coomassie Blue according to standard protocols, and the production of PilC(300–700) was confirmed by the detection of the presence in the gels of an abundant, appropriately-sized peptide of approximately 46kD.

In order to detect the immunogenicity of the PilC (300–700) product, the region of the SDS-PAGE gel containing the PilC(300–700) polypeptide was excised from parallel unstained lanes, homogenized, and the protein eluted into a buffer of 0.1% Triton X-100 in water by passive diffusion. Rabbits were given a priming intradermal injection of homogenized gel slices (containing approximately 500 μg PilC(300–700) protein), followed 3 weeks later by a subcutaneous boost (of approximately 500 μg of eluted protein). An initial test serum was then collected after an additional 14 days. All of the test animals yielded a specific high titer antibody response. The antibodies induced by PilC(300–700) were immunologically reactive not only with that polypeptide (i.e., PilCl(300–700)), but also with native PilC1 and native PilC2.

The results demonstrate, inter alia, the following. PilC contains antigenic epitopes that can elicit a strong immunogenic response. At least some of the immunogenic epitopes are shared (cross-reactive) between PilC1 and PilC2, despite differences in primary amino acid sequence. The technique of subcloning discrete portions of the PilC protein under control of an inducible promoter allows mapping of antigenic epitopes. Sufficient quantities of specific oligopeptides of known antigenicity can be produced for use in screening the in vivo immune response after exposure to the intact pathogen.

The following listed materials are on deposit under the terms of the Budapest Treaty with the American Type Culture Collection (ATCC), 12301 Parklawn Dr., Rockville, Md. 20852, and have been assigned the following Accession Numbers.

| Description | ATCC No. | Deposit Date |
| --- | --- | --- |
| pABJ03 in *E. coli* (DH5) | 68519 | Jan. 28, 1991 |
| pABJ04 in *E. coli* (DH5) | 68520 | Jan. 28, 1991 |

Upon allowance and issuance of this application as a United States Patent, all restriction on availability of these deposits will be irrevocably removed; and access to the designated deposits will be available during pendency of the above-named application to one determined by the Commissioner to be entitled thereto under 37 CFR 1.14 and 35 USC 1.22. Moreover, the designated deposits will be maintained for a period of thirty (30) years from the date of deposit, or for five (5) years after the last request for the deposit; or for the enforceable life of the U.S. patent, whichever is longer. The deposited materials mentioned herein are intended for convenience only, and are not required to practice the present invention in view of the descriptions herein, and in addition these materials are incorporated herein by reference.

INDUSTRIAL APPLICABILITY

The invention, in the various manifestations disclosed herein, has many industrial uses, some of which are the following. The pilC DNAs may be used for the design of probes for the detection of pilC nucleic acids in samples. The probes derived from the DNAs may be used to detect pilC nucleic acids in, for example, chemical synthetic reactions. The polynucleotide probes are also useful in detecting viral nucleic acids in humans, and thus, may serve as a basis for diagnosis of pathogenic microorganisms containing type 4 pilin, for example, gonococcal and/or meningococcal infections in humans.

In addition to the above, the DNAs provided herein provide information and a means for synthesizing polypeptides containing epitopes of PilC. These polypeptides are useful in detecting antibodies to PilC antigens. A series of immunoassays the relevant neisserial infection, based on recombinant polypeptides containing pilC epitopes are described herein, and will find commercial use in diagnosing diseases caused by these microorganisms. In addition, the polypeptides derived from the pilC DNAs disclosed herein will have utility as vaccines for treatment of infections caused by meningococci and gonococci.

The polypeptides derived from the pilC DNAs, besides the above stated uses, are also useful for raising anti-PilC antibodies. Thus, they may be used in vaccines against the relevant microorganisms. Moreover, the antibodies produced as a result of immunization with the polypeptides containing an immunoreactive PilC epitope are also useful as passive vaccines, or in the detection of the presence of PilC antigens in samples. Thus, they may be used to assay the production of polypeptides derived from PilC in chemical systems. The anti-PilC antibodies may also be used to monitor the efficacy of anti-neisserial agents in screening programs where these agents are tested in tissue culture systems. Another important use for anti-PilC antibodies is in affinity chromatography for the purification of PilC derived polypeptides. The purified PilC polypeptide preparations may be used in vaccines.

For convenience, the anti-PilC antibodies and polypeptides containing regions encoded in pilC, whether natural or recombinant, may be packaged into kits.

REFERENCES CITED HEREIN

Badgasarian, M. M., et al., *Gene* (1983) 26:273–282.
Beard, M. K. M., et al., *J. Bacteriol.* (1990) 172:2601–2607.
Bergstrom, S., et al., *Proc. Natl. Acad. Sci. USA* (1986) 83:3890–3894.
Brinton, C. C., et al., in Brooks, G. F., et al. (eds.) *Immunobiology of Neisseria gonorrhoeae* (1978), American Society for Microbiology, Washington, D.C., pp. 155–178.
Edman, P., and Bregg, G., *Eur. J. Biochem.* (1967) 1:80–91.
Elleman, T. C., and Hoyne, P. A., *J. Bacteriol.* (1984) 160:1184–1187.
Elleman, T. C., et al., *J. Bacteriol.* (1986) 168:574–580.
Engstrom, A., et al., *EMBO J.* (1984) 1:2065–2070.
Fast, R., et al., *Gene* (1989) 85:227–231.
Fischer, S. H., and Rest, R. F., *Infect. Immun.* (1988) 56:1574–1579.
Frank-Kamenetskii, M. D., and Vologodskii, A. V., *Nature* (1984) 304:481–482.
Furste, J. P., et al., *Gene* (1986) 48:119–131.
Gill, D. R., et al., *Mol. Gen. Genet.* (1986) 205:134–145.
Gotschlich, E. C., et al., *J. Exp. Med.* (1986) 164:868–881.
Haas, R., and Meyer, T., *Cell* (1986) 44:107–115.
Haas, R., et al., *Proc. Natl. Acad. Sci. USA* (1987) 84:9079–9083.
Hagblom, P., et al., *Nature* (1985) 315:156–158.
Hanahan, D., in Glover, D. M. (ed.), *DNA Cloning: A Practical Approach* (1985), Vol. I., pp. 109–129 (IRL Press, Oxford).
Hanson, M. S., and Brinton, C. C., *Nature* (1988) 322:265–268.
Hill, S. A., et al., *Mol. Microbiol.* (1990) 4:1341–1352.
Hultgren, S. J., et al., *Proc. Natl. Acad. Sci. USA* (1989) 86:4357–4361.
Kellogg, D. S., et al., *J. Bacteriol.* (1968) 96:596–605.
Laemmli, U. K., *Nature* (1970), 227:680–685.
Lindberg, F. P., et al., *Nature* (1987) 328:84–87.
Lindberg et al., *J. Bacteriol.* (1989) 171:6052–6058.
Marrs, C. F., et al., *J. Bacteriol.* (1985) 163:132–139.
Mattick, J. S., et al., *J. Bacteriol.* (1987) 169:33–41.
McKern, N. M., et al., *FEBS Lett.* (1983) 164:149–153.
Meyer, T., et al., *Cell* (1982) 30:45–52.
Meyer et al., *Proc. Natl. Acad. Sci. USA* (1984) 81:6110–6114.
Moch, T., et al., *Proc. Natl. Acad. Sci. USA* (1987) 84:3462–3466.
Mool, F. R., et al., *J. Bacteriol.* (1983) 154:41–49.
Murphy, G. L., et al., *Cell* (1989) 56:589–547.
Norgren, M., et al., *Mol. Microbiol.* (1987) 1:169–178.
Norlander, L., et al., *J. Bacteriol.* (1981) 145:788–795.
Norquist, A., et al., *FEMS Microbiol. Lett.* (1978) 4:71–75.
Orndorff, P. E., and Falkow, S., *J. Bacteriol.* (1984) 159:736–744.
Panyutin, I. G., et al., *Proc. Natl. Acad. Sci. USA* (1990) 87:867–870.
Pasloske, B. L., et al., *FEBS Lett.* (1985) 183:408–412.
Pearce, W. C., and Buchanan, T. M., *J. Clin. Invest.* (1978) 61:931–943.
Sanger, F., et al., *Proc. Natl. Acad. Sci. USA* (1977) 74:5463–5467.
Sanger, F., et al., *J. Mol. Biol.* (1980) 143:161–178.
Segal. E., et al., *Cell* (1985) 40:293–300.
Seifert, H. S., et al., *Proc. Natl. Acad. Sci. USA* (1986) 83:735–739.
Seifert, H. S., et al., *J. Bacteriol.* (1990) 172:40–46.
Shaw, C. E., and Taylor, R. K., *Infect. Immun.* (1990) 58:3042–3049.
Southern, E. M., *J. Mol. Biol.* (1975) 98:503–517.
Stern, A., et al., *Cell* (1986) 47:61–71.
Stibitz, S., et al., *Nature* (1989) 338:266–269.
Stoker, N. G., et al., in Hames, B. D., and Higgin, S. J. (eds.), *Transcription and Translation; A Practical Approach* (1984) (IRL Press, Oxford).
Studier et al., *Methods in Enzymology* (1990) 185:60–89.
Swanson, J., *J. Exp. Med.* (1973) 137:571–589.
Swanson, J., et al., *J. Exp. Med.* (1985) 162:729–744.
Swanson, J., et al., *Cell* (1986) 47:267–276.
Taha, M. K., et al., *EMBO J.* (1988) 7:4367–4378.
Taylor, T., et al., *Vaccine* (1988) 6:151–154.
Thompson, R., and Achtman, M., *Mol. Gen. Genet.* (1978) 165:295–304.
Towbin, H., et al., *Proc. Natl. Acad. Sci. USA* (1979) 76:4350–4354.
von Heinje, G., *Eur. J. Biochem.* (1983) 133:17–21.
Watt, P. J., and Ward, M. E., in Beachey, E. H. (ed.), *Bacterial Adherence* (1980) Series B, Vol. 6, pp. 253–288, Chapman & Hall, London.
Weiser, J. N., et al., *Cell* (1989) 59:657–665.
Willems, R., et al., *EMBO J.* (1990) 9:2803–2809.
Yanis-Perron, C., et al., *Gene* (1985) 33:103–119.
Broach (1981) in *Molecular Biology of the Yeast Saccharomyces*, Vol. 1, p.445, Cold Spring Harbor Press.
Broach et al., *Meth. Enz.* (1983) 101:307. Catty (1988), ANTIBODIES, Volume 1: A PRACTICAL APPROACH (IRL Press).
Chaney et al. (1986), *Cell and Molecular Genetics* 12:237.
Chakrabarti et al. (1985), *Mol. Cell Biol.* 5:3403.
Cohen (1972), *Proc. Natl. Acad. Sci. USA* 69:2110.
Glennie et al. (1982), *Nature* 295:712.
Grunstein and Hogness (1975), *Proc. Natl. Acad. Sci. USA* 73:3961.
Grych et al. (1985), *Nature* 316:74. Hammerling et al. (1981), MONOCLONAL ANTIBODIES AND T-CELL HYBRIDOMAS.
Hess et al. (1968), *J. Adv. Enzyme Reg* 7:149.
Hinnen et al. (1978), *Proc. Natl. Acad. Sci.* 75:1929.
Hitzeman et al. (1980), *J. Biol. Chem.* 255:2073.

Holland et al. (1978), *Biochemistry* 17:4900.

Holland (1981), *J. Biol. Chem.* 256:1385.

Holland and Holland (1980), *J. Biol. Chem.* 255:2596.

Hunyh, T. V. et al. (1985) in DNA CLONING TECHNIQUES; A PRACTICAL APPROACH (D. Glover, Ed., IRL Press, Oxford, U.K.) pp. 49–78.

Immun. Rev. (1982) 62:185.

Ito et al. (1984), *Agric. Biol. Chem.* 48:341.

Kennett et al. (1980) MONOCLONAL ANTIBODIES.

Laemmli (1970), *Nature* 227:680.

Luckow and Summers (1989), *Virology* 17:31.

Mackett et al. (1984), *J. Virol.* 49:857.

Maniatis, T., et al. (1982) MOLECULAR CLONING; A LABORATORY MANUAL (Cold Spring Harbor Press, Cold Spring Harbor, N.Y.).

Maniatis et al. (1989), MOLECULAR CLONING; A LABORATORY MANUAL, Second Edition (Cold Spring Harbor Press, Cold Spring Harbor, N.Y.).

Mayer and Walker, eds. (1987), IMMUNOCHEMICAL METHODS IN CELL AND MOLECULAR BIOLOGY (Academic Press, London).

Maxam et al. (1980), *Methods in Enzymology* 65:499.

MacNamara et al. (1984), *Science* 226:1325.

Messing et al. (1981), *Nucleic Acids Res.* 9:309.

Messing (1983), *Methods in Enzymology* 101:20–37.

METHODS IN ENZYMOLOGY (Academic Press).

Moss (1987) in GENE TRANSFER VECTORS FOR MAMMALIAN CELLS (Miller and Calos, eds., Cold Spring Harbor Laboratory, Cold Spring Harbor, N.Y.), p. 10.

Neurath et al. (1984), *Science* 224:392.

Saiki et al. (1986), *Nature* 324:163.

Saiki et al. (1988), *Science* 239:487.

Sanger et al. (1977), *Proc. Natl. Acad. Sci. USA* 74:5463.

Setlow, ed. (1988), GENETIC ENGINEERING. Vol. 10, p. 195–219 (Plenum Publishing Co., N.Y.

Schreier, M., et al. (1980) HYBRIDOMA TECHNIQUES

Scopes (1984), PROTEIN PURIFICATION, PRINCIPLES AND PRACTICE, Second Edition (Springer-Verlag, N.Y.).

Tsu and Herzenberg (1980), in SELECTED METHODS IN CELLULAR IMMUNOLOGY (W. H. Freeman and Co.) pp. 373–391.

Vytdehaag et al. (1985), *J. Immunol.* 134:1225.

Valenzuela, P., et al. (1982), *Nature* 298:344.

Valenzuela, P., et al. (1984), in HEPATITIS B (Millman, I., et al., ed, Plenum Press) pp. 225–236.

Warner (1984), *DNA* 3:401.

Wu and Grossman (1987), METHODS IN ENZYMOLOGY Vol. 154, RECOMBINANT DNA, Part E.

Wu (1987), METHODS IN ENZYMOLOGY Vol 155, RECOMBINANT DNA, part F.

Zoller (1982), *Nucleic Acids Res.* 10:6487.

---

We claim:

1. A purified polypeptide comprising an amino acid sequence of at least 15 contiguous amino acids encoded in a pilC gene of Neisseria, wherein the pilC gene of Neisseria is comprised of a nucleotide sequence depicted in a SEQ ID NO selected from the group consisting of SEQ ID NO:1, SEQ ID NOS.8–28, and SEQ ID NO:29, and wherein the purified polypeptide is immunologically identifiable with a polypeptide encoded in pilC of Neisseria.

2. A purified polypeptide according to claim 1, wherein the purified polypeptide comprises a truncated PilC1 sequence comprising amino acids from about amino acid 300 to about amino acid 700 of PilC 1.

3. A purified polypeptide produced by a cell transformed with a recombinant expression system, wherein the expression system comprises a polynucleotide encoding a polypeptide comprising an amino acid sequence of at least 15 contiguous amino acids encoded in a pilC gene of Neisseria, wherein the pilC gene of Neisseria is comprised of a nucleotide sequence depicted in a SEQ ID NO selected from the group consisting of SEQ ID NO:1, SEQ ID NOS.8–28, and SEQ ID NO:29, and wherein the purified polypeptide is immunologically identifiable with a polypeptide encoded in pilC of Neisseria, wherein the polynucleotide is operably linked to a control sequence compatible with a desired host.

4. A polypeptide according to claim 3, wherein the polypeptide comprises a truncated PilC1 sequence comprising amino acids from about amino acid 300 to about amino acid 700 of PilC1.

5. A polypeptide affixed to a solid substrate, wherein the polypeptide is the polypeptide of claim 1.

6. A polypeptide affixed to a solid substrate, wherein the polypeptide is the polypeptide of claim 2.

7. A polypeptide affixed to a solid substrate, wherein the polypeptide is the polypeptide of claim 3.

8. A polypeptide affixed to a solid substrate, wherein the polypeptide is the polypeptide of claim 4.

9. A composition comprised of a purified polypeptide, wherein the purified polypeptide is the polypeptide of claim 1.

10. A composition comprised of a purified polypeptide, wherein the purified polypeptide is the polypeptide of claim 2.

11. A composition comprised of a purified polypeptide, wherein the purified polypeptide is the polypeptide of claim 3.

12. A composition comprised of a purified polypeptide, wherein the purified polypeptide is the polypeptide of claim 4.

13. A composition comprised of a purified anti-PilC antibody wherein the PilC is from Neisseria and is encoded in a pilC gene of Neisseria, wherein the pilC gene of Neisseria is comprised of a nucleotide sequence depicted in a SEQ ID NO selected from the group consisting of SEQ ID NO:1, SEQ ID NOS:8–28, and SEQ ID NO:29.

14. A kit for analyzing samples for the presence of anti-PilC antibodies comprising:
(a) an antigen packaged in a suitable container, wherein the antigen is the polypeptide of claim 1; and
(b) instructions on the performance of the analysis which uses the antigen of (a).

15. A kit for analyzing samples for the presence of anti-PilC antibodies comprising:
(a) an antigen packaged in a suitable container, wherein the antigen is the polypeptide of claim 2; and
(b) instructions on the performance of the analysis which uses the antigen of (a).

16. A kit for analyzing samples for the presence of anti-PilC antibodies comprising:
(a) an antigen packaged in a suitable container, wherein the antigen is the polypeptide of claim 3; and
(b) instructions on the performance of the analysis which uses the antigen of (a).

17. A kit for analyzing samples for the presence of anti-PilC antibodies comprising:
(a) an antigen packaged in a suitable container, wherein the antigen is the polypeptide of claim 4; and
(b) instructions on the performance of the analysis which uses the antigen of (a).

18. A kit for analyzing samples for the presence of an antigen comprised of a polypeptide that is immunologically identifiable with a polypeptide encoded in a pilC gene of Neisseria, wherein a pilC gene of Neisseria is comprised of a nucleotide sequence depicted in a SEQ ID NO selected from the group consisting of SEQ ID NO:1, SEQ ID NOS:8–28, and SEQ ID NO:29 comprising:

(a) a composition comprised of antibodies directed against the antigen comprised of a polypeptide that is immunological identifiable with a polypeptide encoded in a pilC gene of Neisseria, wherein the composition is according to claim 13, and wherein the composition is packaged in a suitable container; and
(b) instructions for performing the analysis.

19. A method for producing antibodies to PilC of Neisseria comprising administering to an individual a composition comprised of an isolated immunogenic polypeptide comprising an amino acid sequence of at least 15 contiguous amino acids encoded in a pilC gene of Neisseria, wherein the pilC gene of Neisseria is comprised of a nucleotide sequence depicted in a SEQ ID NO selected from the group consisting of SEQ ID NO:1, SEQ ID NOS.8–28, and SEQ ID NO:29, and wherein the purified polypeptide is immunologically identifiable with a polypeptide encoded in pilC of Neisseria, and wherein the isolated immunogenic polypeptide is administered in an amount sufficient to produce an immune response to the immunogenic polypeptide.

20. A kit for analyzing samples for the presence of anti-PilC antibodies comprising:
(a) an antigen packaged in a suitable container, wherein the antigen is the polypeptide of claim 5; and
(b) instructions on the performance of the analysis which uses the antigen of (a).

21. A kit for analyzing samples for the presence of anti-PilC antibodies comprising:
(a) an antigen packaged in a suitable container, wherein the antigen is the polypeptide of claim 6; and
(b) instructions on the performance of the analysis which uses the antigen of (a).

22. A kit for analyzing samples for the presence of anti-PilC antibodies comprising:
(a) an antigen packaged in a suitable container, wherein the antigen is the polypeptide of claim 7; and
(b) instructions on the performance of the analysis which uses the antigen of (a).

23. A kit for analyzing samples for the presence of anti-PilC antibodies comprising:
(a) an antigen packaged in a suitable container, wherein the antigen is the polypeptide of claim 8; and
(b) instructions on the performance of the analysis which uses the antigen of (a).

24. A composition comprising a polypeptide of at least 15 contiguous amino acids encoded in a pilC gene of Neisseria, wherein the pilC gene of Neisseria is comprised of a nucleotide sequence depicted in a SEQ ID NO selected from the group consisting of SEQ ID NO:1, SEQ ID NOS.8–28, and SEQ ID NO:29, and wherein the purified polypeptide is immunologically identifiable with a polypeptide encoded in pilC of Neisseria, wherein the polypeptide of at least 15 contiguous amino acids is expressed in a non-*Neisseria gonorrheae* host cell.

25. A composition according to claim 24, wherein the polypeptide comprises a truncated PilC1 sequence comprising amino acids from about amino acid 300 to about amino acid 700 of PilC1.

26. A purified immunoreactive polypeptide comprised of a truncated PilC1 sequence comprising a linear sequence of amino acids from about 300 to about 700 of pilC1 of *Neisseria gonorrhoea* shown in SEQ ID NO:3 [FIG. 4].

27. A polypeptide according to claim 26, wherein the polypeptide is encoded in the polynucleotide sequence of SEQ ID NO:1 [FIG. 3].

28. A purified immunoreactive polypeptide comprised of a linear sequence of amino acids from about 300 to about 700 of pilC1 of *Neisseria gonorrhoea*, wherein pilC1 polypeptide is expressed from ATCC No. 68520.

29. A purified immunoreactive pilC2 polypeptide of *Neisseria gonorrhea*, wherein pilC2 is encoded in the polynucleotide sequence of SEQ ID NO:29 [FIG. 7].

30. A composition comprised of an isolated immunogenic polypeptide, wherein the polypeptide is comprised of an amino acid sequence of at least 15 contiguous amino acids encoded in a pilC gene of Neisseria wherein the pilC gene is comprised of a nucleotide sequence depicted in a SEQ ID NO selected from the group consisting of SEQ ID NO:1, SEQ ID NOS.8–28, and SEQ ID NO:29, and wherein the purified polypeptide is inmunnologically identifiable with a polypeptide encoded in pilC of Neisseria.

31. A composition comprised of an isolated immunogenic polypeptide, wherein the polypeptide is comprised of a truncated PilC1 amino acid sequence comprising from about amino acid 300 to about amino acid 700 of SEQ ID NO:3, and wherein the immunogenic polyeptide is immunologically identifiable with a polypeptide encoded in PilC1 gene of Neisseria.

32. A purified Neisseria polypeptide comprising an amino acid sequence encoded in a pilC gene of Neisseria, wherein Neisseria includes pilC genes comprised of a nucleotide sequence depicted in a SEQ ID NO selected from the group consisting of SEQ ID NO:1, SEQ ID NOS.8–28, and SEQ ID NO:29, and fragments of the Neisseria pilC polypeptide.

33. A polypeptide according to claim 32 wherein the polypeptide is a fusion polypeptide.

34. A method of preparing a purified polypeptide according to claim 3 comprising:
    incubating the cell containing a recombinant expression system encoding the polypeptide under conditions to allow expression of the polypeptide; and
    purifying the polypeptide.

35. An immunoassay for detection of anti-Neisseria antibodies comprising:
    (a) providing a sample suspected of containing anti-Neisseria antibodies;
    (b) providing an antigen comprised of a polypeptide according to claim 1;
    (c) incubating the sample of (a) with the antigen of (b) under conditions which allow the formation of antibody-antigen complexes; and
    (d) detecting the presence of antibody-antigen complexes formed in (c), if any.

36. An immunoassay for detection of anti-Neisseria antibodies comprising:
    (a) providing a sample suspected of containing anti-Neisseria antibodies;
    (b) providing an antigen comprised of a polypeptide according to claim 2;
    (c) incubating the sample of (a) with the antigen of (b) under conditions which allow the formation of antibody-antigen complexes; and
    (d) detecting the presence of antibody-antigen complexes formed in (c), if any.

37. An immunoassay for detection of anti-Neisseria antibodies comprising:
    (a) providing a sample suspected of containing anti-Neisseria antibodies;
    (b) providing an antigen comprised of a polypeptide according to claim 3;
    (c) incubating the sample of (a) with the antigen of (b) under conditions which allow the formation of antibody-antigen complexes; and
    (d) detecting the presence of antibody-antigen complexes formed in (c), if any.

38. An immunoassay for detection of anti-Neisseria antibodies comprising:
    (a) providing a sample suspected of containing anti-Neisseria antibodies;
    (b) providing an antigen comprised of a polypeptide according to claim 4;
    (c) incubating the sample of (a) with the antigen of (b) under conditions which allow the formation of antibody-antigen complexes; and
    (d) detecting the presence of antibody-antigen complexes formed in (c), if any.

39. An immunoassay for detection of anti-Neisseria antibodies comprising:
    (a) providing a sample suspected of containing anti-Neisseria antibodies;
    (b) providing an antigen comprised of a polypeptide according to claim 5;
    (c) incubating the sample of (a) with the antigen of (b) under conditions which allow the formation of antibody-antigen complexes; and
    (d) detecting the presence of antibody-antigen complexes formed in (c), if any.

40. An immunoassay for detection of anti-Neisseria antibodies comprising:
    (a) providing a sample suspected of containing anti-Neisseria antibodies;
    (b) providing an antigen comprised of a polypeptide according to claim 6;
    (c) incubating the sample of (a) with the antigen of (b) under conditions which allow the formation of antibody-antigen complexes; and
    (d) detecting the presence of antibody-antigen complexes formed in (c), if any.

41. An immunoassay for detection of anti-Neisseria antibodies comprising:
    (a) providing a sample suspected of containing anti-Neisseria antibodies;
    (b) providing an antigen comprised of a polypeptide according to claim 7;
    (c) incubating the sample of (a) with the antigen of (b) under conditions which allow the formation of antibody-antigen complexes; and
    (d) detecting the presence of antibody-antigen complexes formed in (c), if any.

42. An immunoassay for detection of anti-Neisseria antibodies comprising:
    (a) providing a sample suspected of containing anti-Neisseria antibodies;
    (b) providing an antigen comprised of a polypeptide according to claim 8;
    (c) incubating the sample of (a) with the antigen of (b) under conditions which allow the formation of antibody-antigen complexes; and
    (d) detecting the presence of antibody-antigen complexes formed in (c), if any.

43. An immunoassay for detection of anti-Neisseria antibodies comprising:
    (a) providing a sample suspected of containing anti-Neisseria antibodies;
    (b) providing an antigen comprised of a polypeptide according to claim 32;

(c) incubating the sample of (a) with the antigen of (b) under conditions which allow the formation of antibody-antigen complexes; and (d) detecting the presence of antibody-antigen complexes formed in (c), if any.

44. An immunoassay for detection of anti-Neisseria antibodies comprising:

(a) providing a sample suspected of containing anti-Neisseria antibodies;

(b) providing an antigen comprised of a polypeptide according to claim 33;

(c) incubating the sample of (a) with the antigen of (b) under conditions which allow the formation of antibody-antigen complexes; and (d) detecting the presence of antibody-antigen complexes formed in (c), if any.

* * * * *